United States Patent [19]
Hemstreet, III et al.

[11] Patent Number: 5,741,648
[45] Date of Patent: *Apr. 21, 1998

[54] CELL ANALYSIS METHOD USING QUANTITATIVE FLUORESCENCE IMAGE ANALYSIS

[75] Inventors: George P. Hemstreet, III; Robert E. Hurst; Rebecca B. Bonner, all of Oklahoma City; Jian Yu Rao, Edmond, all of Okla.

[73] Assignee: The Board of Regents of the University of Oklahoma, Norman, Okla.

[ * ] Notice: The term of this patent shall not extend beyond the expiration date of Pat. No. 5,733,721.

[21] Appl. No.: 605,342

[22] Filed: Feb. 9, 1996

Related U.S. Application Data

[63] Continuation of Ser. No. 984,191, Dec. 20, 1992.

[51] Int. Cl.$^6$ .......................... G01N 33/574; G01N 33/53
[52] U.S. Cl. ..................... 435/6; 435/7.21; 435/7.23; 436/63; 436/64; 436/813
[58] Field of Search ................................ 435/7.23, 7.21, 435/6; 436/63, 64, 813

[56] References Cited

U.S. PATENT DOCUMENTS

| | | | |
|---|---|---|---|
| 4,741,043 | 4/1988 | Bacus | 382/128 |
| 4,965,725 | 10/1990 | Rutenberg | 364/382 |
| 5,008,185 | 4/1991 | Bacus | 435/436 |

OTHER PUBLICATIONS

P. L. Jones et al., Quantitative Immunofluorescence, Anti--ras p21 Antibody Specificity, and Cellular Oncoprotein Levels, *Biochemical and Biophysical Research Communications*, vol. 167, No. 2, 1990, pp. 464–470.

G.P. Hemstreet et al., "Quantitative Fluorescence Image Analysis in Bladder Cancer Screening", *Journal of Occupational Medicine*, vol. 32. No. 9, Sep. 1990, pp. 822–828.

J.Y. Rao et al., "Cellular F-Actin Levels as a Marker for Cellular Transformation: Relationship to Cell Division and Differentiation", *Cancer Research*, 50, Apr. 1990, pp. 2215–2220.

R.A. Bass et al., "DNA Cytometry and Cytology By Quantitative Fluorescence Image Analysis in Symptomatic Bladder Cancer Patients", *International Journal Cancer*, 40, 1987, pp. 698–705.

R.E. Hurst et al., "Molecular and Cellular biological Approaches and Techniques in the Detection of Bladder Cancer and Enhanced Risk for Bladder Cancer in High-Risk Groups", *Journal of Occupational Medicine*, vol. 32, No. 9, Sep. 1990, pp. 854–862.

Y. Fradet et al., "Polymorphic Expression of a Human Superficial Bladder Tumor Antigen Defined By Mouse Monoclonal Antibodies", *Proc. Nat'l Acad. Sci.*, USA, vol. 84, Oct. 1987, pp. 7227–7231.

P.F. McGowan et al., "Equilibrium Binding of Hoechst 33258 and Hoechst 33342 Fluorochromes with Rat Colorectal Cells", *The Journal of Histochemistry and Cytochemistry*, vol. 36, No. 7, 1988, pp. 757–762.

J.Y. Rao et al., "Cellular F-Actin Levels as a Marker for Cellular Transformation: Correlation with Bladder Cancer Risk", *Cancer Research*, 51, Jun. 1, 1991, pp. 2762–2767.

W.L. Parry et al., "Cancer Detection By Quantitative Fluorescence Image Analysis", *The Journal of Urology*, vol. 139, Feb. 1988, pp. 270–274.

G.M. Marsh et al., "A Protocol For Bladder Cancer Screening and Medical Surveillance Among High-Risk Groups: The Drake Health Registry Experience", *Journal of Occupational Medicine*, vol. 32, No. 9, Sep. 1990, pp. 881–886.

G.P. Hemstreet et al., "DNA Hyperploidy As A Marker For Biological Response To Bladder Carcinogen Exposure", *International Journal Cancer*, 42, 1988, pp. 817–820.

D.P. Wood et al., "DNA, RNA and Immunohistochemical Characterization of the Her–2/neu Oncogene In Transitional Cell Carcinoma of the Bladder", *The Journal of Urology*, vol. 146, Nov. 1991, pp. 1398–1401.

G.P. Hemstreet et al., "Identification of a High Risk Subgroup of Grade 1 Transitional Cell Carcinoma Using Image Analysis Based Deoxyribonucleic Acid Ploidy Analysis of Tumor Tissue", *The Journal of Urology*, vol. 146, Dec. 1991, pp. 1525–1529.

L.G. Koss, "Tumors of the Urinary Tract and Prostate", *Diagnostic Cytology and Its Histological Bases*, Third ed., vol. 2, 1979, pp. 749–811.

*Primary Examiner*—Toni R. Scheiner
*Attorney, Agent, or Firm*—Dunlap & Codding,P.C.

[57] ABSTRACT

A system for evaluating one or more biochemical markers for evaluating individual cancer risk, cancer diagnosis and for monitoring therapeutic effectiveness and cancer recurrence, particularly of bladder cancer. The system uses automated quantitative fluorescence image analysis of a cell sample collected from a body organ. Cells are treated with a fixative solution which inhibits crystal formation. Cell images are selected and stored as grey level images for further analysis. Cell images may be corrected for autofluorescence using a novel autofluorescence correction method. A neural net computer may be used to distinguish truepositive images from false-positive images to improve accuracy of cancer risk assessment. Cells having images positive for a marker amy be compared to threshold quantities related to predetermined cancer risk.

39 Claims, 24 Drawing Sheets

Sensitivity and Specificity of M344 antibody with voided urines as a function of threshold number of positive cells.

Longitudinal followup of a single patient using p300/M344 marker.
■ = number of positive cells in urine. ▲ = biopsy results.

Operating characteristics of cells with >5C DNA as a marker for identifying risk in benzidine-exposed cohort.

Operating characteristics of G-actin as a marker in exposed and control groups.

CELL ANALYSIS METHOD USING QUANTITATIVE FLUORESCENCE IMAGE ANALYSIS

This is a continuation of copending application(s) Ser. No. 07/984,191 filed on Dec. 20, 1992.

BACKGROUND

This invention relates to methods for screening cell samples for cytological factors using quantitative fluorescence image analysis, and more particularly, but not by way of limitation, to a method for screening cell samples for cytological factors indicative of cancer or for an increased risk for cancer using quantitative fluorescence image analysis.

An estimated 47,000 cases of bladder cancer were diagnosed in 1991. Approximately 10,000 people were estimated to have died from bladder cancer in 1991. Most of the deaths occurred in people who were not diagnosed early while the cancer was curable. The 5-year survival for noninvasive disease is about 88%, but only 50% for invasive disease, even without nodal involvement. The 5-year survival with metastasis to the lymph nodes is only about 18%. This means that such patients will almost certainly die from bladder cancer or metastases.

Bladder cancer develops by two routes--papillary and flat lesions. Approximately 15% of tumors progress from relatively noninvasive nonmetastatic lesions that are not life threatening to dangerous invasive, metastatic lesions. Papillary lesions progress from benign papillomas that protrude from the bladder surface, to noninvasive malignancies growing into the bladder lumen, and finally to invasive, metastatic malignancies capable of causing death. At the lower grades of this progression, cells are cytologically "atypical," and appear similar to those seen in other conditions not related to cancer, notably inflammation, obstruction, or stones. In the higher grades, such cells are cytologically "suspicious" or "positive" and have a quite characteristic appearance. Flat lesions progress through several stages of dysplasia (a premalignant lesion), culminating in carcinoma in situ (CIS), a noninvasive lesion in which the cells appear highly aberrant and are generally classified as "suspicious," even though the lesion is not cancer per se. However, approximately one-third of such lesions progress to high-grade invasive cancer that is rapidly life threatening. The key to controlling bladder cancer is to detect lesions before they become invasive, and failing that, to detect invasive lesions as early as possible.

Until recently, bladder cancer was diagnosed almost exclusively by either cystoscopy, wherein a fiber optic device is inserted into the bladder and lesions are detected visually by a urologist, or by conventional Papanicolaou staining of bladder cells obtained from urine or from a bladder wash (hereafter called "conventional cytology"). Cystoscopy is an invasive procedure and is therefore unsuitable for screening. Its major use is to detect tumors in patients expressing the symptom complex characteristic of bladder cancer--hematuria, pain, or urinary obstruction. Unfortunately, symptoms usually do not occur until the tumor has progressed to a more dangerous grade or stage. The difficulty with conventional cytology is that while its sensitivity to high-grade lesions is approximately 90%, the sensitivity to lower grade lesions is highly dependent upon the training of the cytopathologist. Grade II and above tumors were detected with a sensitivity of 78% by highly trained cytopathologists, but with much less efficiency by pathologists not specifically trained in urinary cytology. Highly curable Grade I tumors are virtually undetectable by cytopathology.

Research has shown that an image analysis system can screen urine samples having cells labeled with DNA-binding fluorescent dyes to identify "alarms," which are potentially abnormal objects that exceed certain size-brightness thresholds. When this is coupled with a trained human observer to eliminate artifacts and visually classify cells and with DNA measurements to detect cells that exceed the limit of 5C DNA, an effective cancer detection system results. Because the normal diploid amount of DNA (2C) can be doubled in dividing cells, it is not possible to determine from ploidy alone whether a cell in the 2C–4C region is a normal cell in the process of division or an abnormal cell, additional parameters are needed. Also, morphology alone is insufficient, since many low-grade tumors produce "atypical" cells which have minimally altered morphologies and are also produced by noncancer processes.

Malignant cells and high- and low-grade tumor cells with stained DNA can be classified using appropriately modified criteria presented by L. G. Koss in "Tumors of the Urinary Tract and Prostate", in *Diagnostic Cytology and Its Histological Bases*, Third ed. Vol. 2, J. B. Lippincott, Phil., pp. 749–811 (1979) which is hereby specifically incorporated herein by reference.

The mainstay of cancer diagnosis has been the recognition of cancer cells by a human expert. Humans can learn to recognize such cells visually, but the process of screening samples generally requires a high level of skill and knowledge. The work is generally fatiguing and boring due to its repetitive nature. Cytology is therefore an excellent candidate for automation, and it has been a desired goal to combine quantitative measurements of cell features to identify cancer cells in cell specimens. Although a number of different approaches have been tried, the image analysis approach of attaching a television camera to the microscope, and extracting "features" from the image, and then using those quantitative feature measurements as diagnostic parameters has been used almost exclusively. The term "features" encompasses a wide variety of parameters, including dimensional and ratio parameters. Dimensional parameters include, but are not limited to, density (brightness or darkness), area and length measurements, and dispersion measurements (e.g., standard deviation) of features. Ratio parameters include nuclear/cytoplasmic area and other similar derived parameters. Image analysis is by and large an algorithmic approach, and ultimately bogs down in the long computational times required to process images and features with discriminant analysis or other statistical approaches.

Quantitative Fluorescence Image Analysis

Quantitative fluorescence image analysis (QFIA) is an instrumentation technology that can be used to quantitate molecular changes at the cellular level. The technology relies on a computerized microscope programmed and standardized to automatically make biochemical and immunochemical measurements at the molecular level in single cells using fluorescent probes. The particular advantage of image analysis is that quantitative molecular determinations can be directly correlated with the wealth of information inherent in visual morphology. Proper standardization, and attention to the fluorescent and stoichiometric properties of dyes are the key to using fluorescence as a quantitative methodology.

Comparison of Integrated Grey Level (IGL) versus Optical Density (OD) and Quantification By Fluorescence versus Optical Density Fluorescence and Absorption Probes In order to detect certain molecules, it is generally necessary to use a probe that specifically binds to the molecule of interest. With systems that depend upon measurement of light absorption, that probe is usually referred to as a "stain". Relatively high concentrations are needed. The stain can interact with the molecule of interest in two ways. The stain can cause a chemical reaction that leads to a colored or fluorescent product, or there is a physical interaction between the probe and the molecule of interest so that the probe is bound physically. The first is irreversible, that is the stain cannot be removed without some other chemical reaction (e.g. bleaching). The second is reversible, that is the stain can be washed out. At the concentrations of stains that are usually used, other substances will almost invariably also bind stain.

The chemistry of physically-binding absorption stains is not well understood, and there is rarely a simple stoichiometry (the relationship between the amount bound and the amount of molecule that binds the stain). In order to be able to see the stain, very high concentrations must be used. While it is true that the molecule of interest probably binds the stain most strongly, and other substances usually bind more weakly, the high concentrations involved force the binding equilibria of these weak binding substances strongly to the bound state. Thus, the pattern that is seen is a complex relationship involving the particular molecules of interest and many other non-target molecules as well. The net result is that the amount of staining may bear only a very general relationship to the amount of the molecules of interest. This problem is much less severe when a chemical reaction (e.g. Feulgen reaction) is used rather than a physical interaction (e.g. hematoxylin and eosin staining or Papanicolaou staining).

On the other hand, with fluorescence methods the higher contrast of the signal (light on dark versus dark on light for absorption) means that measurements are inherently much more sensitive and that the signal can be detected at much lower probe concentrations. The stoichiometry is frequently simple in that it is both proportional to the amount of molecule of interest and independent of the amount of probe once some lower limit that saturates the binding sites is exceeded. As a result, fluorescence methods are much more quantitatively accurate than methods relying on physical interactions.

Quantification by Optical Density

The Beer-Lambert law (Eq. 1) describes the relation between the absorbance or optical density, OD (the two terms are used interchangeably); the intensity of transmitted light, I; the intensity of incident light (i.e. before passing through the absorbing substance), $I_o$; the distance the light must pass through the absorbing object (pathlength), L; a molecular constant, a; and the concentration of absorbing molecules, c.

Absorption consists of a darker signal imposed upon a bright background. Operationally, $I_o$ is measured by measuring the $$\text{Absorbance} = OD = -\log\left(\frac{I}{I_o}\right) = aLc \qquad (1)$$

intensity of light transmitted through the slide in a region where there is no absorbing sample while I is measured after passing through the sample. With an image analysis system, an image of a field is captured, and those areas in the background where nothing is absorbing give a measurement of $I_o$. While absorbance and concentration are linearly related, concentration and the intensity of transmitted light, I, are not. Thus, a logarithmic transformation of data is required in order for results to be accurate.

The amount of substance present is calculated by multiplying the concentration by the volume, V, in which the absorbing material is confined. In theory, the amount of DNA could be calculated from Eq. 2 if the molecular constant a were known and if there is a direct proportionality between the amount of probe bound and the amount of DNA that binds it. The actual image consists of a continuous range of different intensities because DNA is not evenly distributed within the nucleus. Note that the volume is the product of the cross sectional area, A, and the thickness, which is the same as L. Thus, the pathlength, L, disappears from the equations.

$$DNA = \left(\frac{OD}{aL}\right) V = \left(\frac{OD}{aL}\right) AL = \frac{(OD)(A)}{a} \qquad (2)$$

A digitized image actually consists of discrete "pixels" or picture elements. An example is the discrete dots that comprise an ordinary television image. In digitization, each pixel, which actually represents an average over some small area, is assigned a discrete value, usually between 0 and 256. White would be 0 while completely black would be 256. This value is referred to as the "grey level" and is denoted by the symbol G. The net result is that the continuous variable I is replaced with the discrete variable G. This operation lumps values that are very close to each other together in the same "box" or grey level value, but the human eye is not able to distinguish the digitized signal from the continuous natural one. If the pixel area is $S_p$, then the total DNA content of a cell nucleus is calculated by summing the DNA contained in each volume corresponding to a pixel over all N pixels that comprise the image. This volume is $S_p L_i$, where $L_i$ is the pathlength at the ith pixel. An equation equivalent to Eq. 2 can be derived and is shown as Eq. 3.

$$DNA = \frac{1}{a} \sum_{i=1}^{N} \frac{OD_i}{L_i} V_i = \frac{S_p}{a} \sum_{i=1}^{N} \left(-\log \frac{G_i}{G_0}\right) = \frac{S_p}{a} IOL \qquad (3)$$

The summation term is the integrated optical density, or IOD. IOD is time consuming to measure because the logarithmic transformation must be performed on each and every data point. Many systems abbreviate the calculation and do not perform the logarithmic calculation on each pixel element. Instead, they calculate an integrated grey level, IGL, which is the average grey level of the image.

$$IGL = \sum_{i=1}^{N} G_i \qquad (4)$$

with absorbance, an error factor is created when the image is not of uniform density, as is the case of images of cells. The error occurs because intensity of transmitted light and concentration are logarithmically, not linearly, related. For an image analysis system, the more exact relation shown in Eq. 3 is approximated as described in Eq. 5. The accuracy of the approximation is dependent upon the range of variation in intensities.

$$DNA = \frac{S_p}{a} \sum_{i=1}^{N} -\log\left(\frac{G_i}{G_0}\right) \approx \frac{S_p}{a} \log \frac{IGL}{G_0} \qquad (5)$$

In practice, a is not known and, indeed, varies from assay to assay and batch to batch of samples because of the problem that the chemical methodology is not particularly reproducible. This problem occurs whether a chemical reaction such as the Feulgen procedure is used or stains such as the Papanicolaou stain are used. This problem is partially overcome by using a standard material, for example, a cell type that has a DNA content that is assumed from other measurements. In the normal, resting cell, the amount of DNA is an exact, fixed amount that is arbitrarily assigned a value of 2.0C. In practice, because, (1) some cells may be dividing (and have more DNA), (2) there are certain errors is inherent in measuring the OD of an image, and (3) there may be some cell-to-cell variation in staining or labeling, the DNA content of a number of normal cells would be determined and the mode used to set the point 2.0C. The mode is selected because it is relatively insensitive to individual variations in the cells being measured. If one further assumes that the molecular constant for the two cell types will be identical (which is not always true), then the DNA content of an unknown cell type, $DNA_u$, is related to the DNA content of the standard cell, $DNA_s$, by Eq. 6, where the term $M(logIGL_s/G_{o,*})$ refers to the mode of the histogram of OD for the normal cells.

$$DNA_u = 2.0 \frac{-logIGL_u/G_{0,u}}{M(-logIGL_s/G_{0,s})} \quad (6)$$

Quantification by Fluorescence

Fluorescence occurs when molecules absorb light, then dissipate some of the energy of the absorbed light in internal molecular transfers wherein light is reemitted at a longer wavelength. In the absence of fluorescence, when a molecule absorbs light, it rapidly emits the light at the same wavelength. This cannot be distinguished from the light that was originally absorbed. In a microscope, fluorescence consists of a bright signal on a dark background, which is the exact opposite of absorption. Additionally, the intensity of emitted light is directly proportional to the number of molecules emitting light, is and no logarithmic transformation is required. The fluorescence is also directly proportional to the intensity of the exciting light, $I_e$. The relationship between the intensity of $I_e$, the intensity of fluorescence, $I_f$ and concentration c of molecules is given by Eq. 7.

$$I_f = I_e K c \quad (7)$$

The parameter K is a constant for a particular system. It contains a number of other variables including the quantum yield, which is the fraction of light quanta that are emitted after absorption, the strength of absorption of light at the exciting wavelength, and orientation factors peculiar to the particular instrumental configuration. Generally, the molecules will be randomly oriented, which means that light will be emitted at all orientations, and only some fraction will be picked up by the microscope objective.

The chemical selectivity of fluorescence dyes is generally much greater than that of absorption dyes. This occurs because in order to be able to see staining of absorption dyes with a microscope, very high concentrations of stain must be used because of the very short pathlengths involved. At such high concentrations many molecules in addition to those of interest will be stained, and very frequently the Beer-Lambert Law (Eq. 1) does not hold exactly, i.e., the relationship between OD and concentration no longer is linear. Thus, some completely arbitrary means of calibration must be used. In the case where Feulgen staining is used as a means of calibration, staining is rarely exactly linear, and the assumption that a cell which has four times the IGL of a diploid cell has four times the DNA content is rarely true.

In contrast to the situation with absorption, in the present invention, the relationship between fluorescence of the probe and the amount of DNA is independently established. How this process operates in the case of DNA is explained thoroughly in the paper by McGowan, et al. ("Equilibrium Binding of Hoechst 33258 and Hoechst 33342 Fluorochromes with Rat Colorectal Cells", *The Journal of Histochemistry and Cytochemistry*, Vol. 36, No. 7, 1988, pp. 757–762). The process is described for immunologic probes in Jones, et al. ("Quantitative Immunofluorescence, Anti-ras p21 Antibody Specificity, and Cellular Oncoprotein Levels", *Biochemical and Biophysical Research Communications*, Vol. 167, No. 2, 1990, pp. 464–470). The references by McGowan, et al., and by Jones, et al., are hereby incorporated herein by reference. Once it is established that this relationship holds, it is not necessary to include a standard curve every time unless there is uncertainty that such a linear relationship holds.

In the present invention, the background of a fluorescent signal, which is essentially black, is assigned a grey level of zero. The gain of the camera is adjusted such that the usual cell images fall within some range that allows for very bright signals. This arbitrary point is assigned to grey level 255. Thus, any signal brighter than this will be truncated at G =255. In the present invention, these truncation occurrences are reported to prevent errors. The real advantage of fluorescence is the linear relationship between fluorescence and concentration using IGL leading to an essentially error-free measurement of amounts of molecules.

DESCRIPTION

The present invention provides a system for evaluating one or more cytological markers for cell analysis, particularly for individual cancer risk assessment, cancer diagnosis, and for monitoring therapeutic effectiveness and cancer recurrence. Quantitative measurements of phenotypic marker profiles can be used to document the risk of malignancy faced by an individual. While many genetic changes may lead to the malignant phenotype, a much smaller number of phenotypic markers may be used to chart the progress towards malignancy. The current invention represents in one version the first successful application of the neural network approach where the input is a gray level image derived from cells labeled for specific molecules using fluorescent probes.

Figure 1:
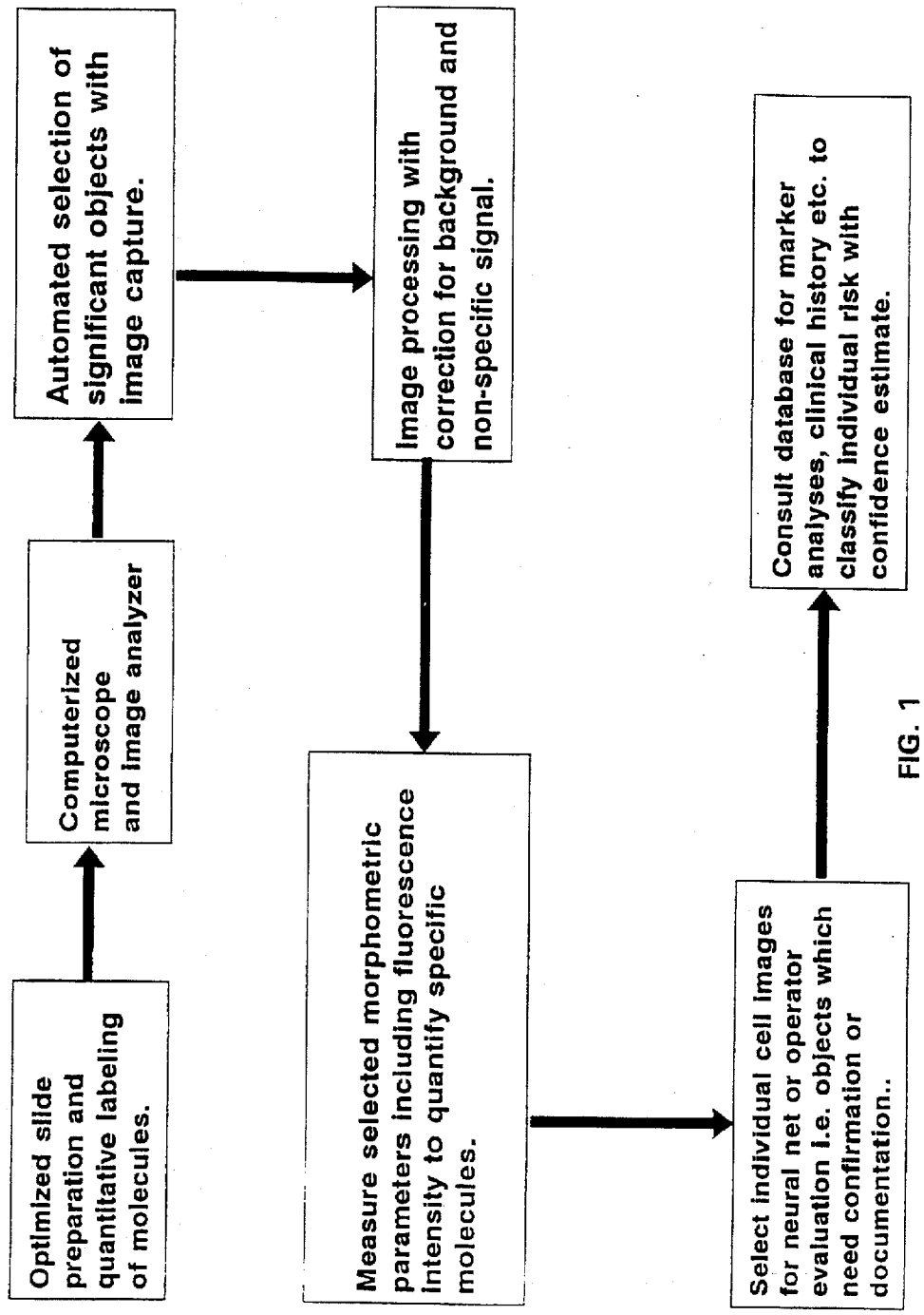
FIG. 1 is a schematic of the overall process of cell analysis using quantitative fluorescence image analysis.

The present invention is generally described in the schematic diagram shown in FIG. 1 and can be briefly summarized as follows. A sample of biological cells is collected. The cells may be collected by washing an organ, such as a bladder, a colon, a small intestine, or bronchial tissues, for example. Or the cells may be collected from body fluid such as urine, pleural fluid or sputum, for example. Or the cells may be collected from a needle aspiration of a body part, gland, or organ, for example the prostate gland.

The sample is prepared for application to a slide, including optimization of the number of cells on the slide. The cells are applied to the slide in preparation for quantitative labeling. The slide is sequentially processed wherein a series of one or more quantitative fluorescent labels is applied to the cell sample in such a way that the labels do not interfere with their affinities to specific cytological markers. In the preferred embodiment of the present invention the fluorescent label is comprised of a fluorochrome bound to an affinity probe. By "fluorochrome bound to an affinity probe" is meant any fluorochrome which is attached directly or indirectly to an affinity probe, or any fluorochrome which itself acts as an affinity probe. An example of the latter is Hoechst 33258. Several fluorochromes are noted in Table IV.

The term affinity probe as used herein is defined to include a material having a specific affinity for a particular type of cytological marker and may include, but is not limited to antibodies, peptides or polypeptides, nucleotides or polynucleotides, dyes, carbohydrates, lectins, and other ligands, and combinations thereof. Several examples of affinity probes are the M344 antibody, anti-EGFR probes such as AB-1, anti-HER-2/neu protein probes such as TA1, and DNase I.

The slide is analyzed using a quantitative fluorescence image analysis system using a system including a microscope means which automatically selects and stores the grey level images of from about 24 to 115 cells per slide. The term microscope means, as used herein, refers to any means by which cells may be magnified to be viewed at a microscopic level, and may include any viewing means which allows the quantitative measurement of cellular markers within a cell. For example, from a slide double-labeled for actin and DNA, 64 images may be stored for DNA evaluation and 48 images may be stored for actin evaluation. The term actin, as used herein, means any cellular actin-type molecule such as F-actin, G-actin, and any other cytological or nuclear actins. Each cell image may be corrected for extraneous fluorescence including back-ground fluorescence (from the sample medium) and autofluorescence. Cells are then quantitatively analyzed for fluorescence of the specific cytological markers. The term cytological marker is meant herein as any cytological feature which may serve to "mark" a particular type of cell or other component of the cell sample and may include, but is not limited to, tumor associated antigens, receptors, cytoskeletal proteins, oncogene proteins, DNA (including genes and chromosomes) and RNA and which may be labeled by a fluorescent label.

Cells which require further confirmation or documentation as normal or abnormal are then evaluated either by a trained technician or by a trained neural net computer. For example, certain cells which demonstrate a high quantity of the M344 label of the p300 marker typical of an abnormal cell (i.e., the cells are brightly positive) may actually be normal. These abnormal (cancerous) cells can be distinguished from normal cells because of the differences in the pattern of fluorescence within the cell (FIGS. 2A and 2B) Such differences in fluorescence patterns can be distinguished by a human operator as well as by a trained neural net computer al though the neural net computer performs the task more quickly. Such a finding, where humans can easily recognize the difference but find it difficult to encode into rules represents an ideal use of neural networks. Other markers may occur in similarly differentiable patterns in normal and abnormal cells and can thereby be distinguishable. Once the markers have been analyzed, the marker profile, which contains information about the quantities of the markers in the cells as well as how many cells may be positive for certain markers, the cell sample may be further classified.

In the present invention, the step of classifying the cell sample may comprise (1) generating a marker profile for the cell sample, (2) assigning a cancer risk level to the person who contributed the cell sample, (3) generating a proposed course of clinical action to be followed by the person from whom the cell sample was obtained, or (4) any combination of (1), (2) and (3).

Normal cells within the cell sample are used to establish the calibration for diploid DNA. For example, even in urine from a person having a bladder tumor, most of the cells are normal. For urine cells, approximately 100–200 such cells are measured and the fluorescence intensities are plotted. The mode, the most probable value, of the distribution is determined. Since DNA normally has a discrete value, this fluorescence corresponds to 2C, or the diploid amount of DNA. The advantage of the mode is that the inadvertent inclusion of a few abnormal cells in the distribution does not affect the mode. The DNA content of an unknown cell is determined from Eq. 8, where $M(IGL_N)$ represents the mode fluorescence of the normal cells and B is the background fluorescence, which is usually near zero.

$$DNA_u = 2.0 \times \frac{IGL_u - B}{M(IGL_N) - B} \qquad (8)$$

In contrast to Eq. 6, Eq. 8 is simpler with less inherent error.

Understanding the concept of risk is essential to any program of cancer control. The appearance of a clinically detectable tumor is the end point of a long process that has occurred over many years. It is analogous to a heart attack, which is the end point of a long process of narrowing of the arteries. Both processes are detectable, and markers can point to risk. In the case of heart attacks, elevated cholesterol is such a marker and is often used as an indicator of elevated risk and the need for treatment.

The present invention offers an automated approach using QFIA for multiple marker measurements at the cellular level. By detecting field disease as well as tumors, such measurements can stratify groups labeled as high risk by epidemiologic risk factors. Screening for positive markers in exfoliated cells is noninvasive, and interventions can be targeted to individuals with objective indicators of abnormality. Additionally, marker profiles can be used to target aggressive therapies at individuals with markers indicating high risk for progression or metastasis while indicating conservative therapy for individuals identified as being at lower risk. A third application lies in monitoring cancer patients for response to therapy and for recurrence. The degree of ablation of abnormal markers by therapy will undoubtedly correlate with risk of recurrence, and observing progressive development of abnormal markers may be used to signal early intervention or diminish the need for invasive cystoscopy as a monitoring tool when it does not occur.

Changes in cellular differentiation and proliferation are results of the carcinogenic process. These changes are not necessarily linked to each other. For example, a cytologic low-grade-appearing tumor may have a high proliferation rate with well-differentiated cellular architecture. F-actin is a quantitative marker that reflects the degree of differentiation in model cell-culture systems, with low levels reflecting a less differentiated state.

As shown below for bladder cancer, because quantitative differences in expression of certain markers are important characteristics distinguishing field, low, and high grade tumor cells, marker profiles based upon quantitative methods, such as QFIA, are more likely to be useful than qualitative or semi-quantitative methods.

Bladder Cancer Tumorigenesis

The biochemical changes produced by the process of tumorigenesis can be detected prior to the development of a cancer, and by evaluating those changes using specific, quantitative markers, an individual's risk for developing bladder cancer and, more specifically, dangerous, invasive bladder cancer, can be assessed. For example, while almost all cancer cells contain abnormally low amounts of F-actin, so do many cells from dysplasias. Just as not all people having elevated cholesterol or narrowing of the arteries suffer heart attacks, not all dysplasias develop into cancers. However, no cancer appears to develop that does not proceed through such a stage. Thus, the finding of cells with decreased F-actin, or increased G-actin, its precursor, is a marker for risk.

More information can be obtained by measuring additional markers, such as tumor related antigens or DNA ploidy. In a study based upon a university referral population, which is weighted toward recurrent cancers, the combination of DNA ploidy and visual classification of cells by a trained human observer had an approximate 95% specificity (fraction of noncancer samples not called abnormal), a virtual 100% sensitivity to high-grade tumors, an approximate 80% sensitivity to low-grade tumors and a 20%–30% advantage over conventional Papanicolaou cytology.

Smoking itself can produce cells with >5C DNA by inducing failed cell divisions, although the majority of smokers with cells with >5C in their urine do not develop cancer. A small percentage of smokers will have positive results for this marker when judged against a threshold derived from a non-smoking population. However, the finding of both abnormal actin and DNA ploidy is a strong indicator of risk in a smoker. The abnormal actin marker points to the process of altered cellular differentiation and suggests the cells with abnormal DNA ploidy arose from a dysplastic lesion rather than the process described above. While failed cell divisions are abnormal and indicate some risk for cancer, the presence of dysplastic lesions is indicative of much higher risk for cancer. Addition of a third marker can provide even more information.

For example, presence of the p300 protein produced by low-grade tumor cells and some dysplastic cells (and detected by the M344 antibody), is a further indicator of risk for cancer. In a study of over 600 urine samples from workers exposed to chemicals that cause bladder cancer, some of whom also smoked, some 15% showed abnormal actin, some 8% showed abnormal DNA and some 2% showed abnormal p300. However, only 5 showed all 3 markers abnormal, and 3 of these were found to have bladder cancer. Of these, 2 had been positive a year earlier, but had not had a detectable cancer at that time. Thus, having all 3 markers positive appears to occur late in the tumorigenesis, near the time when a tumor can be detected, and is a very strong indicator of risk.

Bladder cancer is frequently multifocal, and large areas may display altered biochemical or morphological changes ("field disease") indicative of increased risk. These findings are particularly important to occupational studies because, as noted above, F-actin may be a useful marker for individual bladder cancer risk assignment. More importantly, such early transformation-related events might be correctable by retinoids, providing a theoretical approach for chemopreventive intervention. Based upon findings that retinoids administered in animal carcinogenesis models reverse cytologic changes detectable by quantitative fluorescence imaging analysis (QFIA), retinoid chemoprevention in persons identified with QFIA as being at high risk for cancer may well offer a more effective control strategy than waiting until tumors appear to administer retinoids. Although DNA ploidy changes can occur early in experimental carcinogenesis, F-actin or other markers may be as or more effective intermediate end-point indicators.

The results to date indicate that QFIA measurements on voided urine cells can play an important role in occupational screening programs. The sensitivity and specificity of currently available QFIA technology combining DNA and morphology are better than is usual in most screening tests. The main shortcomings are the high cost and the inability of currently available instrumentation to make multiple marker measurements that could enhance sensitivity to low-grade tumors and simultaneously provide an individual risk profile. The objective of the present invention is to overcome these shortcomings.

Specificity-Sensitivity of the p300 Marker

Figures 2A, 2B:
FIG. 2A is a grey level image of an abnormal cell labeled with M344.
FIG. 2B is a grey level image of a normal cell labeled with M344.

The sensitivity and specificity of the p300-marker was independently tested in a study of symptomatic and asymptomatic subjects and patients with bladder cancer using the M344 antibody. The specificity using voided urines was determined with a mixture of samples, consisting of completely normal, asymptomatic controls that approximately matched the age distribution of cancer cases and patients currently without cancer being monitored for recurrence. Preliminary data analysis has shown that p300 is a valuable marker for the detection of low-grade bladder cancers, with the amount per cell being less significant in identifying tumor cells than the appearance of a specific pattern consisting of small, relatively bright granular fluorescence in the cytoplasm (FIG. 2A) versus a less granularly, more generally fluorescent appearance in normal cells (FIG. 2B).

Figure 3:
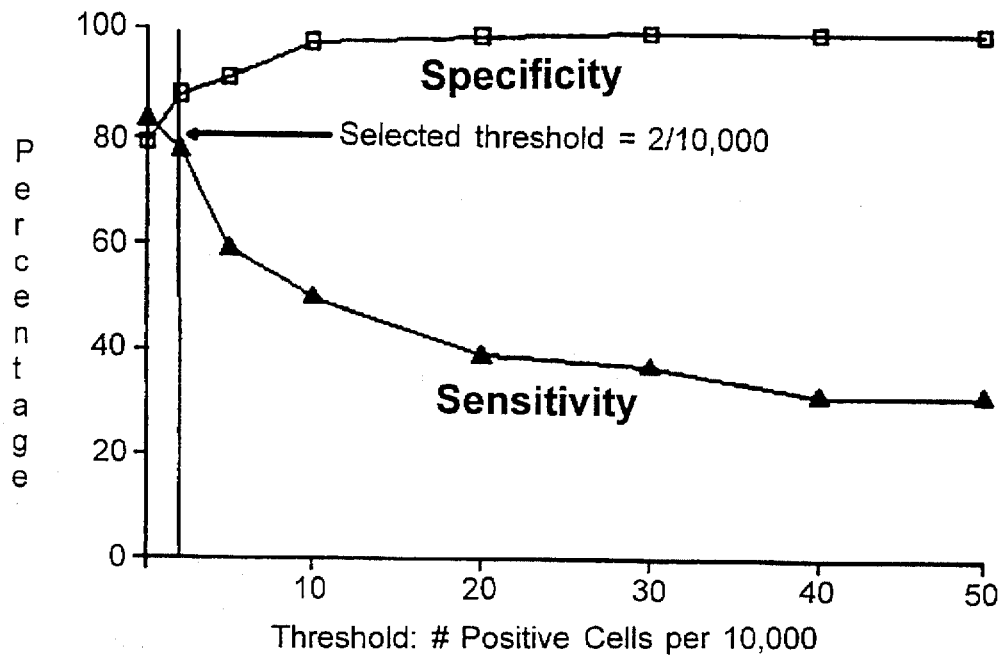
FIG. 3 is a sensitivity/specificity plot of the M344 antibody in voided urine cells.

Analysis has shown that cells can be effectively scored as either "positive" or "negative". Additional studies have shown that in any given tumor, not only are not all cells positive for the marker, but frequently the positive fraction was small. This suggested that the finding of a small number of positive cells (i.e., "rare events") in a urine sample might be significant. In order to determine the optimal threshold, the data were analyzed by the "receiver operating characteristics" (ROC) curve method in which sensitivity and specificity are plotted as a function of the threshold selected. FIG. 3 shows the M344 ROC curve for voided urines.

FIG. 3 indicates that finding two cells per 10,000 cells examined in a voided urine is a strong, positive marker for cancer risk. The p300 protein is also expressed by at least some pre-malignant lesions, as shown by the finding of positive cells in some of the controls. Positive cells were also found in patients with benign prostatic hyperplasia and bladder outlet obstruction, suggesting the protein is a marker for altered differentiation that can be produced either by carcinogenesis or by the promoting effects of urinary stasis. Completely asymptomatic normals express this protein very rarely, and the specificity is in excess of 98% with such individuals. Overall, with the inclusion of symptomatic individuals, the sensitivity with voided urines was 90% with 90% specificity. Preliminary analysis of the data using the stratified risk approach and the field disease studies suggest that p300 appears earlier than abnormal DNA ploidy but after abnormal G-actin.

Figure 4:
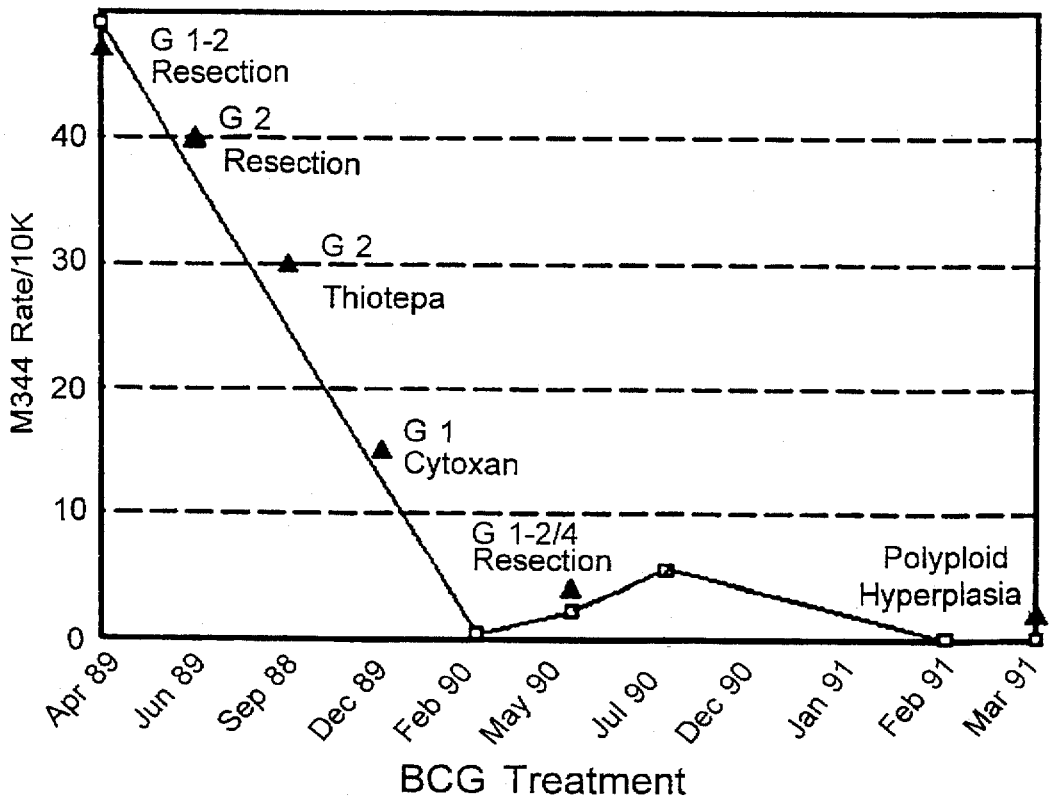
FIG. 4 is a longitudinal follow up of a person using M344.

Preliminary analysis of data from those individuals from whom at least one year follow up is available strongly supports the use of p300 as a useful marker for monitoring response to therapy and risk of recurrence. To this point, no patient who normalized (became negative for p300) experienced a recurrence of cancer without prior reappearance of M344-positive cells. Also, patients who did not normalize in response to treatment have tended to recur rapidly and at a rate much in excess of the recurrence rate by patients who normalize. FIG. 4 shows the long-term follow up of a subject treated with BCG. The subject on initial diagnosis was found to have several, large low-grade tumors which were resected. The subject was treated with BCG, as indicated by the boxes below the graph, and the number of positive cells dropped to the normal range. Later, positive cells appeared and the patient experienced a recurrence. After resection and treatment with an additional course of BCG, the patient has not recurred and his results have remained negative.

G-actin as an Early Marker for Bladder Cancer Risk

G-actin has also been investigated as a marker in cancer patients. Globular actin or G-actin, as the monomeric precursor for F-actin, bears a reciprocal relationship to F-actin. Decreased F-actin (a cytoskeletal protein) levels in urinary tract cells is a marker for decreased differentiation. In 9 patients with biopsy-proven disease the mean G-actin content of urinary cells was 105 units, and in 19 asymptomatic controls was 48.4 units. This difference was significant at $p<0.001$.

EXAMPLE 1

Quantitative Fluorescence Image Analysis of Cells with Multiple Markers

Transitional cell carcinomas (TCC) of the bladder are known to frequently develop as multiple foci in time and place within the bladder. The bladder represents a complex ecosystem of interfacing epithelial and stromal cells, and the progressive subversion of growth and differentiation controls, leading to eventual emergence of cells capable of at least partial autonomous growth, requires years. Altered histopathology is a relatively late event in carcinogenesis, but biochemical or genetic manifestations of carcinogenic damage may be detectable years earlier. As described below, phenotypic markers were mapped in the bladder by quantifying markers in sample specimens from the tumor, the adjacent epithelium and from distant epithelium in persons with bladder cancer and in bladder cells from normal persons. Because quantitative rather than qualitative differences in gene expression and protein levels probably underlay most of the differences between malignant and normal phenotypes, the ability to quantify markers is needed. Accordingly, QFIA was used to quantify the phenotypic markers in single cells from the sample specimens. Because of its visual morphologic component, and in contrast to methods such as flow cytometry, QFIA can link conventional morphologic assessment with quantitative biochemical markers at the single cell level. The markers included; QFIA cytology, a combination of visual morphology and the presence of cells with DNA in excess of 5C (which is a marker for genetic instability), the p300 tumor-related antigen detected by the M344 monoclonal antibody, the differentiation-related proteins epidermal growth factor receptor (EGFR) and G-actin, and p185, a protein product of the HER-2/neu oncogene.

Experimental Methodology

The patient population consisted of 30 patients with TCC and 6 noncancer controls, all of whom gave informed consent. To obtain single cells for QFIA analysis, "touch preps" were made from biopsy specimens of tumor, adjacent field and random distant epithelium in the operating room. The surface of the tissue was touched to a polylysine-coated slide, and the remainder of the tissue was submitted for routine pathology. Separate forceps were used for each piece of tissue to prevent cross contamination. The slides were then triple-labeled for DNA using 8 μM Hoechst 33258, for p185 using the TA1 antibody directly conjugated to Texas Red, and for p300 using the M344 mouse monoclonal antibody and a 3-stage sequence using biotin goat antimouse secondary antibody and Bodipy-labeled avidin. With fourteen of the tumors and all six controls a second triple-labeled slide was prepared labeling for DNA as above, for EGFR using AB-1 mouse monoclonal (Oncogene Science) and the same visualization system as was used with M344 above, and for DNase I (Molecular Probes) directly conjugated to Texas Red to detect G-actin. A corresponding negative control slide omitting primary antibodies was also prepared. All reagents were optimized to achieve saturation. Labeling was carried out in an automated slide labeling device (Instrumentation Laboratories Code-On). With each batch of slides, standard cell lines known to be high and low expressors for each quantitative marker were also included, thereby enabling the quantitation of each marker found to be present in a particular cell. Tables I–III show examples of three different staining sequences similar to the staining procedure used in Example 1.

TABLE I

Stain Sequence - G-actin + M344 + DNA

| EVENT | STATION | TIME | | SOLUTION |
|---|---|---|---|---|
| 1 | 11 | 1.00 | MIX | PAD |
| 2 | 14 | 1.00 | MIX | M344 |
| 3 | 7 | 30.00 | | INCUBATOR |
| 4 | 8 | 0.50 | | PAD |
| 5 | 10 | 0.10 | | 1X AUTO. BUFFER |
| 6 | 9 | 0.50 | | (BM-M30) |
| 7 | 10 | 0.10 | | PAD |
| 8 | 11 | 0.50 | | 1X AUTO. BUFFER |
| 9 | 10 | 0.50 | | (BM-M30) |
| 10 | 12 | 1.00 | MIX | PAD |
| 11 | 15 | 1.00 | MIX | 1X AUTO. BUFFER |
| 12 | 7 | 30.00 | | (BM-M30) |
| 13 | 8 | 0.50 | | PAD |
| 14 | 10 | 0.10 | | SECONDARY |
| 15 | 9 | 0.50 | | INCUBATOR |
| 16 | 10 | 0.10 | | PAD |
| 17 | 11 | 0.50 | | 1X AUTO. BUFFER |
| 18 | 10 | 0.10 | | (BM-M30) |
| 19 | 12 | 0.50 | | PAD |
| 20 | 10 | 0.10 | | 1X AUTO. BUFFER |
| 21 | 11 | 0.50 | | (BM-M30) |
| 22 | 10 | 0.10 | | PAD |
| 23 | 12 | 1.00 | MIX | 1X AUTO. BUFFER |
| 24 | 16 | 1.00 | MIX | (BM-M30) |
| 25 | 7 | 30.00 | | PAD |
| 26 | 11 | 0.50 | | 1X AUTO. BUFFER |
| 27 | 10 | 0.10 | | (BM-M30) |
| 28 | 12 | 0.50 | | PAD |
| 29 | 10 | 0.10 | | 1X AUTO. BUFFER |
| 30 | 9 | 1.00 | | (BM-M30) |
| 31 | 10 | 0.60 | | PAD |
| 32 | 8 | 1.00 | MIX | BODIPY |
| 33 | 17 | 1.00 | MIX | INCUBATOR |
| 34 | 7 | 30.00 | | PAD |
| 35 | 8 | 1.00 | | 1X AUTO. BUFFER |
| 36 | 10 | 0.10 | | (BM-M30) |
| 37 | 11 | 0.50 | | PAD |
| 38 | 10 | 0.10 | | 1X AUTO. BUFFER |
| 39 | 11 | 0.60 | | (BM-M30) |
| 40 | 10 | 0.10 | | PAD |
| 41 | 8 | 1.00 | MIX | 1X AUTO. BUFFER |
| 42 | 6 | 2.00 | | (BM-M30) |
| 43 | 12 | 0.30 | | PAD |
| 44 | 6 | 0.50 | | G-ACTIN |
| 45 | 11 | 0.30 | | INCUBATOR |
| 46 | 6 | 0.50 | | PAD |
| 47 | 9 | 0.30 | | 1X AUTO. BUFFER |
| 48 | 6 | 0.50 | | (BM-M30) |
| 49 | 8 | 0.30 | | PAD |
| 50 | 6 | 2.00 | | 1X AUTO. BUFFER |

TABLE I-continued

Stain Sequence - G-actin + M344 + DNA

| EVENT | STATION | TIME | SOLUTION |
|---|---|---|---|
| The total processing time: 146.10 min. | | | (BM-M30) |
| | | | PAD |
| | | | 1X AUTO. BUFFER |
| | | | (BM-M30) |
| | | | PAD |
| | | | HOECHST |

TABLE II

Stain Sequence - M344 + DNA

| EVENT | STATION | TIME | | SOLUTION |
|---|---|---|---|---|
| 1 | 11 | 1.00 | MIX | PAD |
| 2 | 15 | 1.00 | MIX | PRIMARY ANTIBODY |
| 3 | 7 | 30.00 | | HEATED WET |
| 4 | 8 | 0.50 | | CHAMBER |
| 5 | 10 | 0.10 | | PAD |
| 6 | 9 | 0.30 | | 1X AUTO. BUFFER |
| 7 | 10 | 0.10 | | (BM-M30) |
| 8 | 11 | 0.30 | | PAD |
| 9 | 10 | 0.50 | | 1X AUTO. BUFFER |
| 10 | 12 | 1.00 | MIX | (BM-M30) |
| 11 | 16 | 1.00 | MIX | PAD |
| 12 | 7 | 30.00 | | 1X AUTO. BUFFER |
| 13 | 8 | 0.50 | | (BM-M30) |
| 14 | 10 | 0.10 | | PAD |
| 15 | 9 | 0.50 | | BIOTINYLATED |
| 16 | 10 | 0.10 | | SECONDARY |
| 17 | 11 | 0.50 | | INCUBATOR |
| 18 | 10 | 0.10 | | PAD |
| 19 | 12 | 0.50 | MIX | 1X AUTO. BUFFER |
| 20 | 17 | 0.50 | MIX | (BM-M30) |
| 21 | 7 | 30.00 | | PAD |
| 22 | 8 | 0.50 | | 1X AUTO. BUFFER |
| 23 | 10 | 0.50 | | (BM-M30) |
| 24 | 9 | 0.50 | | PAD |
| 25 | 10 | 0.50 | | 1X AUTO. BUFFER |
| 26 | 11 | 0.50 | | (BM-M30) |
| 27 | 10 | 0.50 | | PAD |
| 28 | 12 | 0.50 | | TEXAS RED |
| 29 | 10 | 0.50 | | INCUBATOR |
| 30 | 9 | 1.00 | | PAD |
| 31 | 10 | 0.60 | | 1X AUTO. BUFFER |
| 32 | 12 | 1.00 | MIX | (BM-M30) |
| 33 | 6 | 2.00 | | PAD |
| 34 | 11 | 0.60 | | 1X AUTO. BUFFER |
| 35 | 6 | 0.50 | | (BM-M30) |
| 36 | 12 | 0.60 | | PAD |
| 37 | 6 | 0.50 | | 1X AUTO. BUFFER |
| 38 | 11 | 0.60 | | (BM-M30) |
| 39 | 6 | 0.50 | | PAD |
| 40 | 12 | 0.60 | | 1X AUTO. BUFFER |
| 41 | 6 | 0.50 | | (BM-M30) |
| 42 | 11 | 0.50 | | PAD |
| 43 | 6 | 2.00 | | 1X AUTO. BUFFER |
| 44 | 12 | 0.60 | | (BM-M30) |
| 45 | 10 | 0.50 | | PAD |

The total processing time: 115.20 min.

| | | | HOECHST |
| | | | PAD |
| | | | HOECHST |
| | | | PAD |
| | | | HOECHST |
| | | | PAD |
| | | | HOECHST |
| | | | PAD |
| | | | HOECHST |
| | | | PAD |
| | | | HOECHST |

TABLE III

| | Stain Sequence - F-Actin + DNA | | |
|---|---|---|---|
| EVENT | STATION | TIME | SOLUTION |
| 1 | 8 | 1.00 MIX | PAD |
| 2 | 17 | 1.00 MIX | ANTIBODY |
| 3 | 7 | 30.00 | INCUBATOR |
| 4 | 8 | 1.00 | PAD |
| 5 | 10 | 0.10 | 1X AUTO. BUFFER (BM-M30) |
| 6 | 11 | 0.50 | |
| 7 | 10 | 0.10 | PAD |
| 8 | 11 | 0.60 | 1X AUTO. BUFFER (BM-M30) |
| 9 | 10 | 0.10 | |
| 10 | 8 | 1.00 MIX | PAD |
| 11 | 6 | 2.00 | 1X AUTO. BUFFER (BM-M30) |
| 12 | 12 | 0.30 | |
| 13 | 6 | 0.50 | PAD |
| 14 | 11 | 0.30 | HOECHST |
| 15 | 6 | 0.50 | PAD |
| 16 | 9 | 0.30 | HOECHST |
| 17 | 6 | 0.50 | PAD |
| 18 | 8 | 0.30 | HOECHST |
| 19 | 6 | 2.00 | PAD |
| | | | HOECHST |
| | | | PAD |
| | | | HOECHST |

The total processing time: 42.10 min.

Filter Sets Used for Quantitation of Fluorochromes

Filters image analysis quality (DRLP grade) with high precision in angle of incidence to avoid problems with image registration. A/R coated rear surface dichroics eliminate additional undesired stray light for quantitative purposes. Narrow band emission filters are selected to maximize fluorochrome properteries and minimize non-specific autofluorescence (see Table IV).

TABLE IV

| Fluorochrome | Excitation | Dichroic Beam Splitter | Emission |
|---|---|---|---|
| Hoechst 33258 | 360 ± 50 nm | 400 @ 45° DRLP | 450 ± 50 nm |
| Texas Red | 560 ± 40 nm | 595 @ 45° DRLP | 630 ± 23 nm |
| Bodipy-Fitc | 485 ± 22 nm | 505 @ 45° DRLP | 530 ± 30 nm |
| Autofluorescence | 540 ± 23 nm | 565 @ 45° DRLP | 590 ± 35 nm |

Neutral Density Filters

Neutral Density filters are comprised of quartz and have a clean flat uniformly coated surface. The degree of transmission required is determined by the fluorochrome, sensitivity of the imaging camera, and the specific marker quantified. A typical set of seven filters would include the following properties at 485 nm absorption (see Table V). The linearity of the camera system can be quantified using known transmission values at each given wave-length. A reference table is then used to correct for non-linearity at each wavelength.

TABLE V

| % Transmission | Optical Density |
|---|---|
| 79.4 | 0.1 |
| 50.1 | 0.3 |
| 25.1 | 0.6 |
| 10.0 | 1.0 |
| 1.0 | 2.0 |
| 0.3 | 2.5 |
| 0.1 | 3.0 |

The present invention also contemplates using a first fluorochrome and a second fluorochrome which may be excited by a single excitation wavelength. In such a case, the single excitation wavelength which causes a first fluorochrome to emit fluorescent light at a first emission wavelength, may also be effective in causing a second fluorochrome to emit fluorescent light at a second emission wavelength which is different from the first emission wavelength.

FIGURE LEGENDS

Figure 5A:
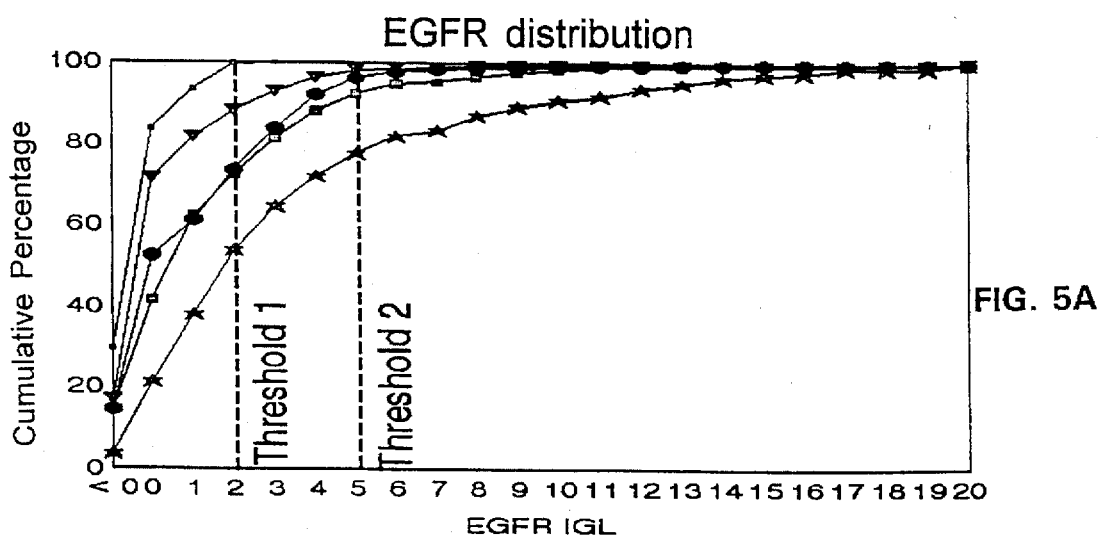
FIG. 5A is a plot of EGFR distribution in relation to field disease.
Figure 5B:
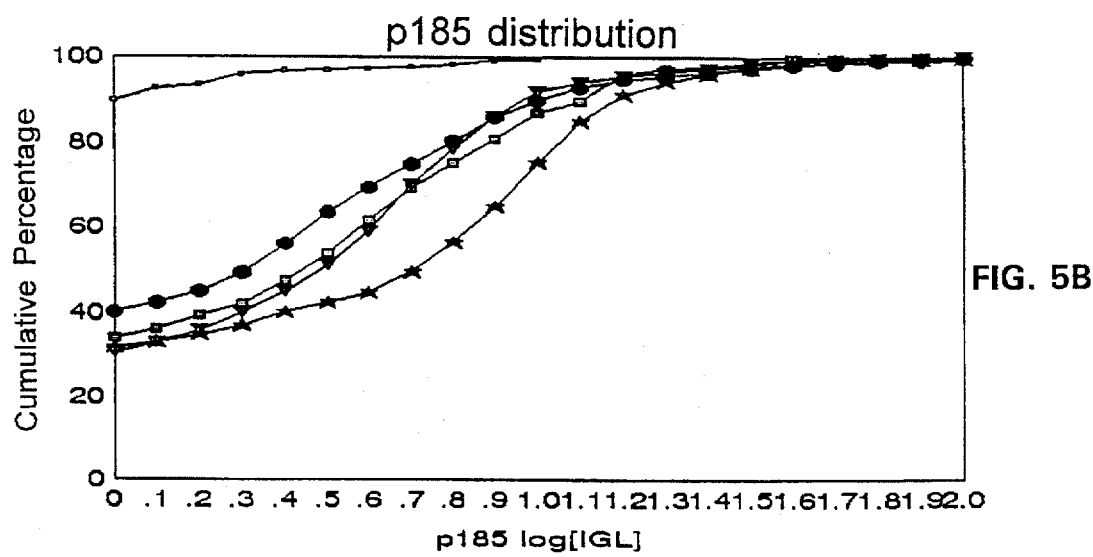
FIG. 5B is a plot of p185 distribution in relation to field disease.
Figure 5C:
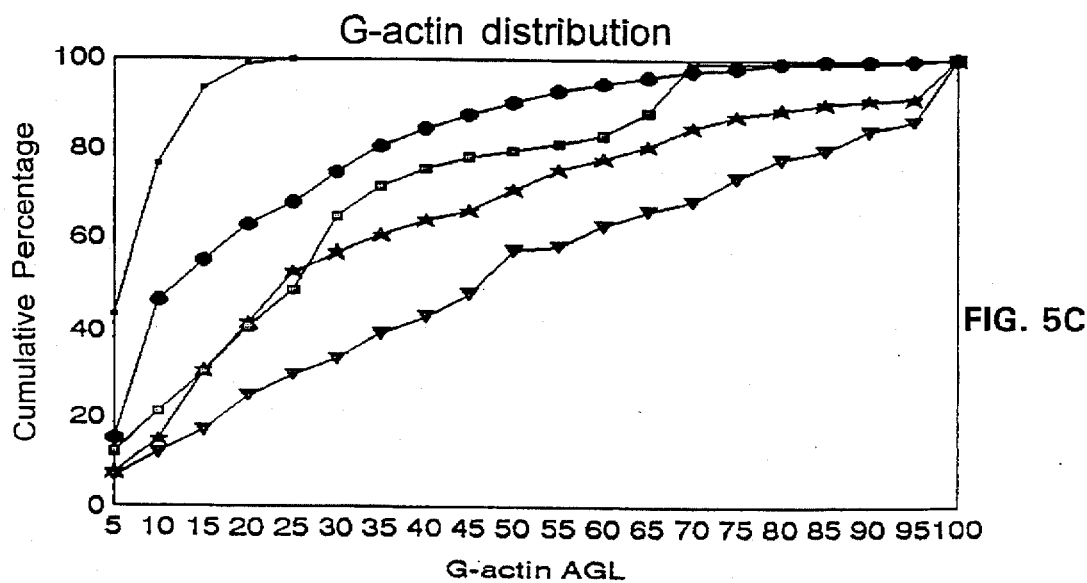
FIG. 5C is a plot of G-actin distribution in relation to field disease.

FIGS. 5A–C: Cumulative distributions of EGFR (FIG. 5A), p185 (FIG. 5B) and G-actin (FIG. 5C) as measured by IGL (integrated grey level), Log[IGL] and AGL (average grey level), respectively. IGL and AGL are calculated by the IBAS image analysis system (Zeiss Instruments) from the digitized, grey-level fluorescence images and represent the fluorescence intensity integrated over a cell image (IGL) and the average intensity (AGL) of all pixels comprising the image. Markers were quantified using the IBAS on a cell by cell basis from 50–100 cells per slide. In tumor biopsies, regions of tumor cells were specifically analyzed. In non-tumor specimens, cells were randomly selected. In both cases infiltrating lymphocytes or blood cells were specifically excluded. The immunofluorescence assays were calibrated against cell lines known to express high and low amounts of the proteins. The 18-3-7 line transfected with an expression vector containing HER-2/neu and the A431 line served as positive controls for p185 and EGFR respectively. A large number of slides were prepared from a single batch of each cell line. A positive (with primary antibody) and negative (without primary antibody) slide for each marker was included with each batch of patient samples, and the cells were labeled and analyzed as described. The IGL or AGL was corrected for background fluorescence by subtracting the mean IGL and AGL determined from approximately 100 cells on the negative control slide. -□-=control; -●-=field of low grade TCC; -▼-=low grade TCC; -■-=field of high grade TCC, and -★-=high grade TCC.

Figure 6:
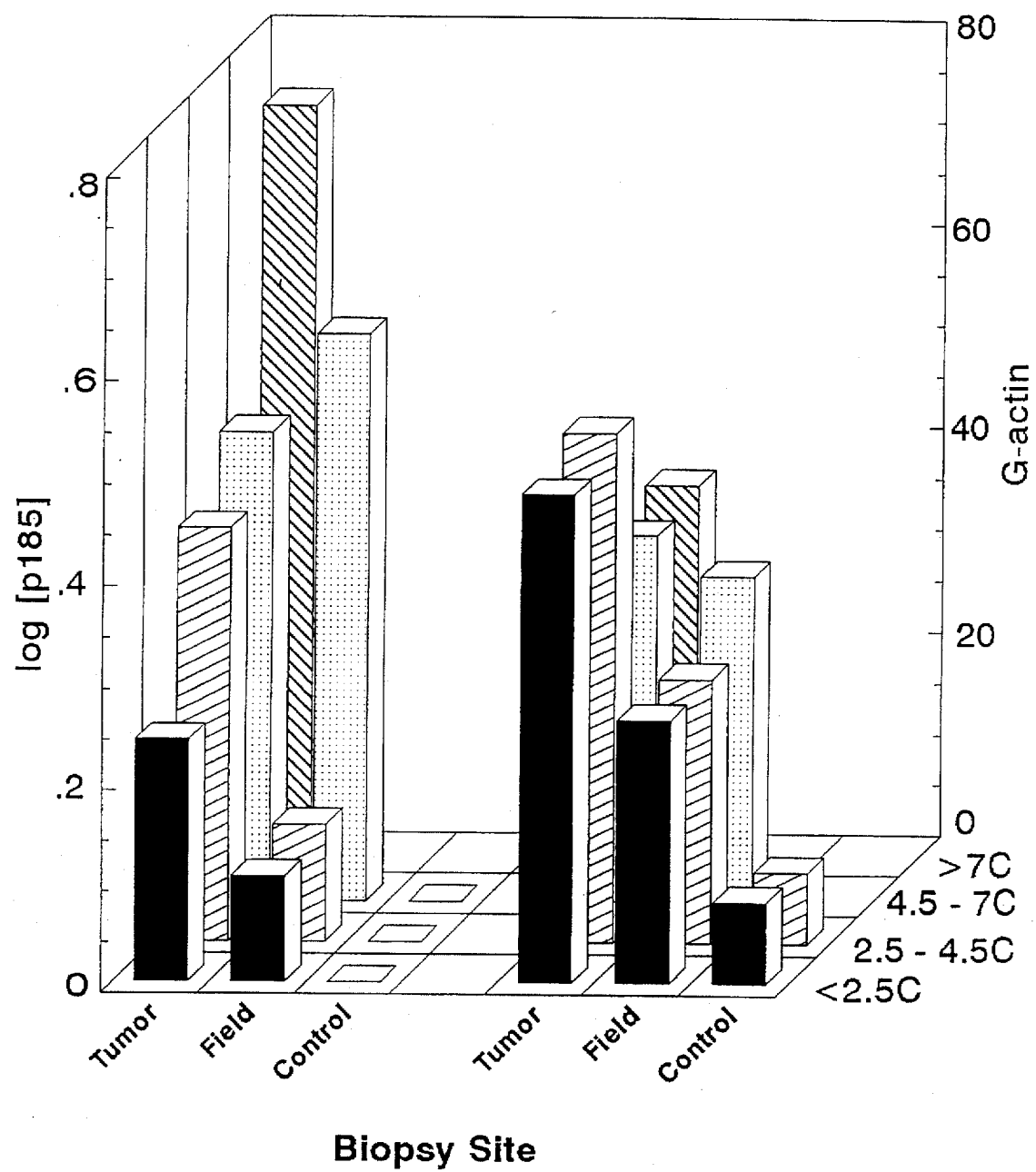
FIG. 6 is a plot of p185 and G-actin quantities in relation to DNA ploidy and field disease.

FIG. 6: Relationships between DNA ploidy and log[p185] or G-actin as a function of biopsy site. The cells were stratified by DNA ploidy and the mean marker content for all the cells from all the patients were plotted as a function of ploidy as shown on the figure.

Figure 7:
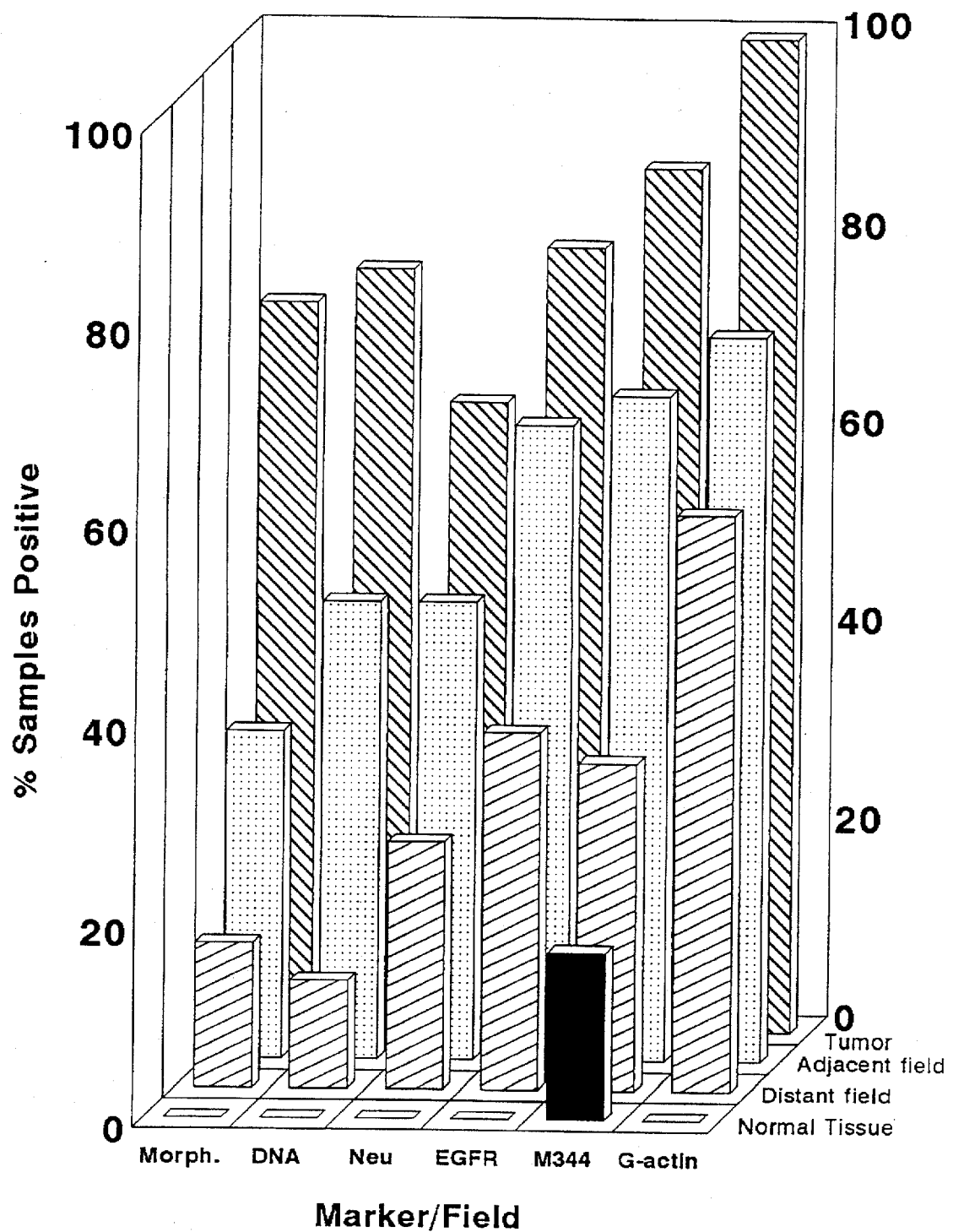
FIG. 7 is a plot of percentage of samples positive for 6 markers in relation to field disease.

FIG. 7: The progression of biochemical markers from control (n=6), random distant field (n=27), adjacent field (n=24) and tumor (n=30) of TCC with markers scored by positive/negative criteria. Cytology was scored by a trained cytologist and confirmed by a pathologist. The presence of cells with "suspicious" morphology labeled the sample as "positive" as did the presence of any cells with >5C DNA. The p300 marker (M344) was scored visually by two independent observers. A sample was considered positive if any positive cells were noted. EGFR and G-actin were approximately normally distributed while p185 (Neu) showed a lognormal distribution. For p185, the mean IGL of cells on the negative control slide was calculated and was subtracted from the IGL of each cell on the sample slide. If the adjusted mean IGL significantly (t-test) exceeded the adjusted IGL of a low expressing cell line (3T3SW480), the sample was labeled as positive. For EGFR, a histogram of normal cells from control patients was constructed, and the presence of cells above the upper limit of normal (threshold, FIG. 3) was used as an indicator of positive. For G-actin, a sample was labeled as positive if the mean IGL was significantly higher ($p<0.05$ by Student's t-test) than the mean of the control patients.

Results

FIGS. 5A–C present the cumulative frequency distributions for EGFR, p185 and G-actin. EGFR and G-actin showed distributions markedly skewed from normal while p185 was distributed normally. The progression in markers could be demonstrated in two ways from these plots by either establishing a threshold or by comparing mean values. EGFR shifted progressively to higher expression levels that could be exploited to develop a positive-negative schema in terms of the fraction of cells exceeding the threshold for normal cells (Threshold 1). The field from low-grade tumors showed a significant increase over the normal field in cells expressing 2-5 EGFR units. Almost identical distribution of EGFR expression by low-grade tumors and the field from high-grade tumors was observed, but high-grade tumors expressed significantly larger numbers of high expressing cells (>5 EGFR units). Little if any p185 expression was found in the normal controls, but in all the abnormal samples an approximately normal distribution was seen with a progressive shift in the maximum to higher mean expression from low grade to high grade and from field to tumor. A schema based upon comparison of mean values was derived in order to score samples. With G-actin all the abnormal cells clustered at mean values that were 3-5 times the mean value of normal cells. A single threshold separated positive from negative while the mean values displayed progression.

The markers were investigated for clustering and statistical independence. Cluster analysis using SAS showed the variables fell into three relatively independent groups. G-actin and EGFR were in one cluster while cells with more than 5C DNA and p185 were in a second cluster. Visual morphology, being a qualitative variable not amenable to cluster analysis, was placed into the second cluster because of the close association with DNA (P<0.05 by Cochran-Mantel-Haenszel analysis). The p300 marker was the third independent cluster.

The measurement of multiple parameters on the same cells can be used to delineate markers that are coexpressed in the same cells and those that are expressed in different cells or which are unrelated to each other. FIG. 6 shows the distribution of p185 and G-actin as a function of the DNA content of the cell stratified by biopsy sites. The association between p185 and DNA content and the independence of G-actin on DNA content are both clearly evident. The pattern for EGFR was almost identical to that of p185 and was not shown.

Differences in marker expression, particularly in EGFR, were observed between low and high grade tumors and their fields. When a threshold of >5%. of cells with more than 5IGL EGFR content (Threshold 2 in FIG. 5A) was used, 2/8 low grade tumors and the corresponding fields were positive, while 6/6 high grade tumor and 3/6 high grade field samples were positive. This difference was statistically different at p<0.05 by the Mann-Whitney U-test. With visual DNA morphology, the difference between low and high grade tumors was statistically significant by Chi-square at p<0.05. Only 24% (4/17) of fields adjacent to low grade tumors had positive visual DNA morphology while in the fields adjacent to high grade tumors, 57% (4/7) were positive (p=0.1 by Chi-square). With p300, the decrease of percentage positive in adjacent field from low grade to high grade tumors (14/17 vs 2/7) was statistically different (p<0.05 by Chi-square). For p185, the positive-negative classification was not significantly different for low and high grade samples, but the mean values of the distribution of IGL between high and low grade tumors (FIG. 5B) was significantly different by analysis of variance (p =0.04).

FIG. 7 summarizes the results after each parameter was stratified into a binary classification schema as described in the legend. FIG. 7 presents the percent of cases positive for each marker in the distant field, adjacent field and tumor without respect to tumor grade and of corresponding tissue from control bladders. Each marker showed a progression from distant field to adjacent field to tumor tissue. With the exception of p300 for which one of the six controls was positive, none of the markers were positive in the control bladders. Every marker was positive in some fraction of the distant field biopsies, and a clear progression in markers was evident in the adjacent field biopsies. G-actin was positive in virtually every tumor and in 58% of distant and 73% of adjacent field biopsies. A large increase between distant and adjacent field was observed for both p300 and DNA ploidy (p<0.01 and 0.05, respectively, by Chi-square).

The data presented in this example of phenotypic markers verify the concept of "field disease" at the biochemical level and which heretofore had been defined solely in histopathologic terms. Clearly, differences in some biochemical phenotypic markers are manifested well before an abnormal histopathology is evident, and some are even abnormally elevated in distant biopsy sites. DNA ploidy changes as far as 10 cm from a primary colon tumor have been observed. The quantitative changes of markers displayed a sequential and progressive pattern from normal, random distant site, adjacent field, and tumor which mapped the progressive course of bladder carcinogenesis in terms of quantitative changes in specific molecules and other phenotypic markers.

These results indicate that the differentiation-related cytoskeletal protein G-actin seems to reflect very early events in bladder carcinogenesis, being abnormal in 60% of the distant biopsies from bladders that contain tumors and essentially 100% of tumors themselves. Previous findings of decreased F-actin in bladder cancer and a strong relation to bladder cancer risk suggested that elevated G-actin (which is the monomeric precursor of F-actin) should be observed. The data presented here confirm the concept that alteration in the cytoskeletal reflected by a shift from a high level of microfilament actin (F-actin) to a high level of globular actin (G-actin) represents an early, common marker for dedifferentiation and shows this phenotypic change persists during cytologic dedifferentiation.

The p300 marker, which is apparently not normally expressed in urothelium, is preferentially expressed in low grade, diploid tumor cells, some premalignant lesions and high grade tumor cells, as well as in a high fraction of fields adjacent to low grade tumors. Previous findings suggesting that abnormal p300 expression was associated with abnormal F-actin but not with abnormal ploidy suggests this marker seems to represent early phenotypic changes that may be related to differentiation.

EGFR clustered with G-actin, even though some correlation with the changes in DNA ploidy, p185 and morphology was noted, which indicates EGFR reflects a set of phenotypic changes more reflective of alterations in differentiation program than of factors relating to the other markers. The enhanced EGFR levels of high-grade tumor cells probably results from a loss of EGF-mediated down-regulation of EGFR expression by high grade tumor cells, a mechanism which functions in normal urothelium and low-grade tumor cells. The quantitative difference in p185 expression between low and high grade tumors suggests the possibility that abnormal HER-2/neu expression in bladder cancers may indicate an elevated risk for progression from low to high grade disease. Elevated p185 can be either a primary event, reflecting activation of the HER-2/neu oncogene, or it may be a phenotypic marker for other genetic events leading to upregulation of HER-2/neu.

Quantitative differences in expression of p185 and EGFR, and not the fraction of positive cells, were both shown to be important characteristics distinguishing field, low, and high grade tumor cells. Therefore, marker profiles based upon QFIA are more likely to be useful than immunohistochemistry, which is semi-quantitative at best.

These results clearly demonstrate that marker-positive cells can originate in areas of the bladder other than tumor, and could represent either premalignant cells or the result of altering the cytokine environment of the bladder with consequent changes in the growth characteristics of the bladder epithelium. These changes denote a phenotype that is strongly associated with the cancer process and which can be used to monitor response to therapy and predict recurrence as well as to detect disease.

Research in evaluating and validating markers has been slowed by the necessity to perform a 5-year follow up study on every marker. An alternative evaluation method that may rapidly provide valuable information concerning how a given marker relates to existing markers and whether it occurs early or late can be obtained by using subjects, stratified according to risk, or according to the probability that they will eventually develop disease. The highest risk group would include patients with histologically-proven disease. The next highest risk category would be patients with a proven history of disease and with abnormal DNA ploidy and cytology, but currently undetectable for the disease. Next would be patients with no currently detectable disease, negative for abnormal cytologies, a previous history and hematuria. The next group would be subjects having hematuria and without a previous disease history. At lowest risk is a general population.

A marker sensitive to early changes would show a graded, parallel fraction of abnormality, while a late marker might only be abnormal in the highest risk group. F-actin has been shown to be an early marker by this approach, and over 90% of the subjects with biopsy-proven cancer showed F-actin-positive results. This approach represents a major advance in that it can provide extensive information about how markers relate to each other, to the time frame and genetic changes involved with carcinogenesis, and the sensitivity and specificity for identifying premalignant or malignant disease in specific populations, including symptomatic and asymptomatic. Thus, carefully selected markers can be evaluated in long-term follow up studies knowing which markers are independent and which are early or late markers.

EXAMPLE 2

Comparison of Results Between Immunochemistry and Quantitative Fluorescence Image Analysis The DNA ploidy and p300/M344 results obtained on the same samples prepared using immunochemical methods and QFIA methods were compared. The immunochemical samples were prepared using the Feulgen DNA determination and light absorption microscopy. The immunochemical p300/M344 analysis was based upon alkaline phosphatase immunohistochemistry with manual scoring rather than fluorescence, but was interpreted against the same positive ($\geq 5$ cells positive for M344/10,000 cells) criterion used to interpret the QFIA samples. The QFIA p300/M344 results were determined using both the automated program with manual confirmation and an entirely manual scoring.

There was complete agreement in ploidy assessment in 20/29 cases (69%). Chi-squared analysis showed a high correlation (p=0.039) between the two sets of results. The agreement in p300/M344 analyses was, in contrast, poor. Of 13 samples, there was agreement on 8. Of the 5 disagreements, QFIA found 4 to be positive that had been scored as negative using immunochemical methods. One of the immunochemical samples was scored as positive but negative using QFIA. Chi-squared analysis showed the correlation to be poor (p=0.28) between the two methods. These results indicate a significant difference in the potential outcomes of analyses using the two methods.

EXAMPLE 3

Bladder Cancer Screening Using QFIA of Biomarkers

The screening was carried out in two phases, a pilot study in one of the cities to identify problems and test protocols, and the full screening, which amounted to 1686 exposed subjects and 388 controls. A total of 2084 exposed subjects and 439 controls were notified, so that 81% and 88% respectively of each group participated. Complete questionnaire information, blood, and urine samples were collected from all the subjects, and shipped to the processing lab.

The experimental design of urine QFIA analysis optimized the usage of urine sample and included as markers, DNA ploidy, G-actin, and p300/M344. The aliquot of urine sample for QFIA was not split, and all of the sample was fixed with 0.5% PF for 15 minutes followed by an equal volume of 50% EtOH MOPSO fixative. Samples fixed in this manner were stored and shipped to the QFIA laboratory at 4° C. Two slides were prepared from each specimen and were triple-labeled with M344 monoclonal antibody conjugated with Bodipy fluorochrome, DNase I conjugated with biotin to measure G-actin for avidin-biotin immunofluorescence with Texas Red fluorochrome, and the DNA stain, Hoechst 33258. One slide served as the negative control. DNA and G-actin were quantified using the Zeiss IBAS and the software of the present invention, while p300/M344 was scored visually.

The slides were stored at $-70°$ C. until analysis was begun using a Zeiss IBAS system. The distribution of positive findings by exposure to benzidine and smoking is listed in Table VI for a subset of subjects.

TABLE VI

Distribution of positive marker test results by benzidine exposure and smoking history.

| | Smokers | | | Non-Smokers | | |
|---|---|---|---|---|---|---|
| Group | G-Actin | DNA | M344 | G-Actin | DNA | M344 |
| Exposed | 61/375 | 35/384 | 13/384 | 22/130 | 14/130 | 5/130 |
| | 16.3% | 9.1% | 3.4% | 16.9% | 10.8% | 3.8% |
| Controls | 5/70 | 8/73 | 2/73 | 4/37 | 1/39 | 2/39 |
| | 7.1% | 11% | 2.7% | 10.8% | 2.6% | 5.1% |

The data set was combed to eliminate all samples that had incorrect or incomplete data. Previous smokers were analyzed with smokers, and no correction for quitting smoking was included. Exposure was calculated both on the basis of years of exposure and from an exposure index. Each of the 12 job titles found to involve benzidine exposure was weighted according to the relative incidence of bladder cancer among workers with that job title. Exposure index was calculated by summing the time worked at a job multiplied by job risk over the entire work history. However, exposure index calculated in that way showed no correlation with biochemical markers or with any other markers such as hematuria. Some correlation was obtained with arbitrary weights of 1, 2 and 3 for low, medium and high exposures, but this may reflect no more than an association with years of exposure.

TABLE VII

Significance (p) of risk factors in producing positive test results by test using Cox Logistic Regression Model.

| | p Value | | |
|---|---|---|---|
| Feature | G-Actin 92/612 | DNA 58/626 | M344 22/626 |
| Pack Years | .0001 | .0001 | .0001 |
| Years of Exposure | .0001 | .0001 | .0001 |
| Prostatic Hyperplasia | .0469 | .0176 | .0002 |
| Exposure Index | .2154 | .9746 | .7379 |
| Hematuria | .3215 | .4558 | .6964 |

The number of abnormal test results in the unexposed, non-smoking group is small, and that is an apparent association with exposure. Most of the differences between exposed and nonexposed populations are highly statistically significant, but rather than present a large number of different $X^2$ comparisons, we elected to test all of these factors simultaneously in the Cox Logistic Regression model as shown in Table VII and simultaneously test other factors such as prostatic hyperplasia and hematuria. Smoking, as measured by pack years, and years of exposure to benzidine are the most significant variables in producing abnormal findings. In the absence of carcinogenic exposure, smoking produces a large effect on DNA ploidy. Other studies in our laboratories suggest that the abnormal cells found in current smokers may not be premalignant. It is likely that smoking produces an immediate clastogenic response that leads to failed cellular divisions with consequent highly abnormal cells with increased DNA content. The vast majority of such cells are terminal mutants that do not divide, and the number of such cells decreases to normal levels after smoking cessation. However, in persons with a previous history of cancer or other strong evidence for field disease, such cells are the abnormal offspring of altered basal cells and are, hence, truly dysplastic.

Of interest was the strong association of prostatic hyperplasia as a risk factor, particularly with the p300/M344 test. In part this may reflect increased risk for bladder cancer but outlet obstruction can produce positive findings as well. Interestingly, hematuria was not associated with positive marker analyses in this study, possibly because so many subjects were positive for hematuria.

Figure 8:
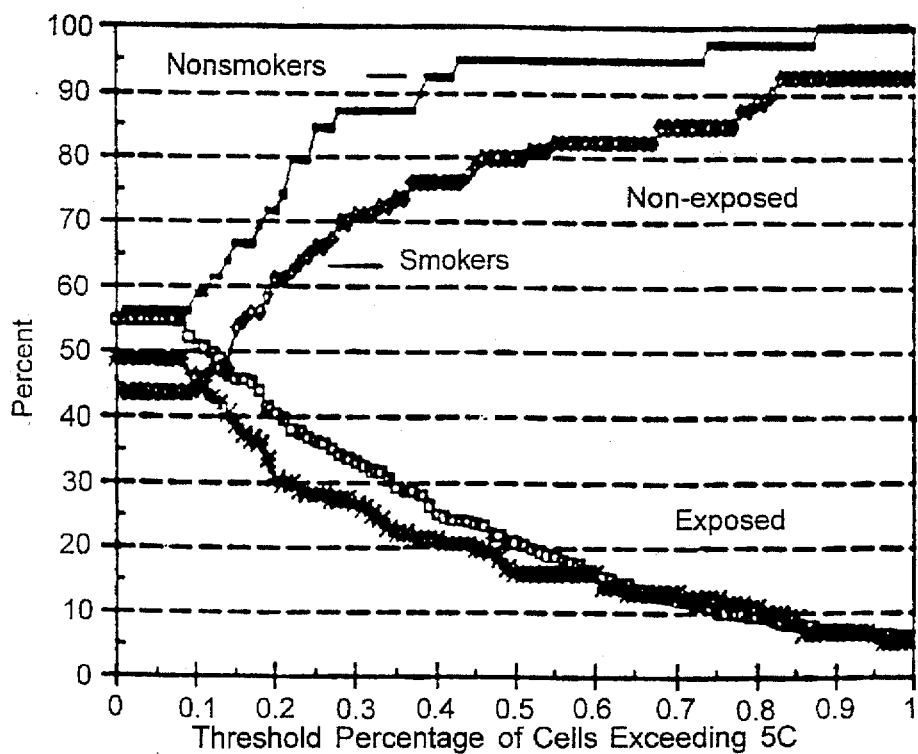
FIG. 8 is a specificity/sensitivity plot of abnormal DNA ploidy in relation to smoking and benzidine exposure history.
Figure 9:
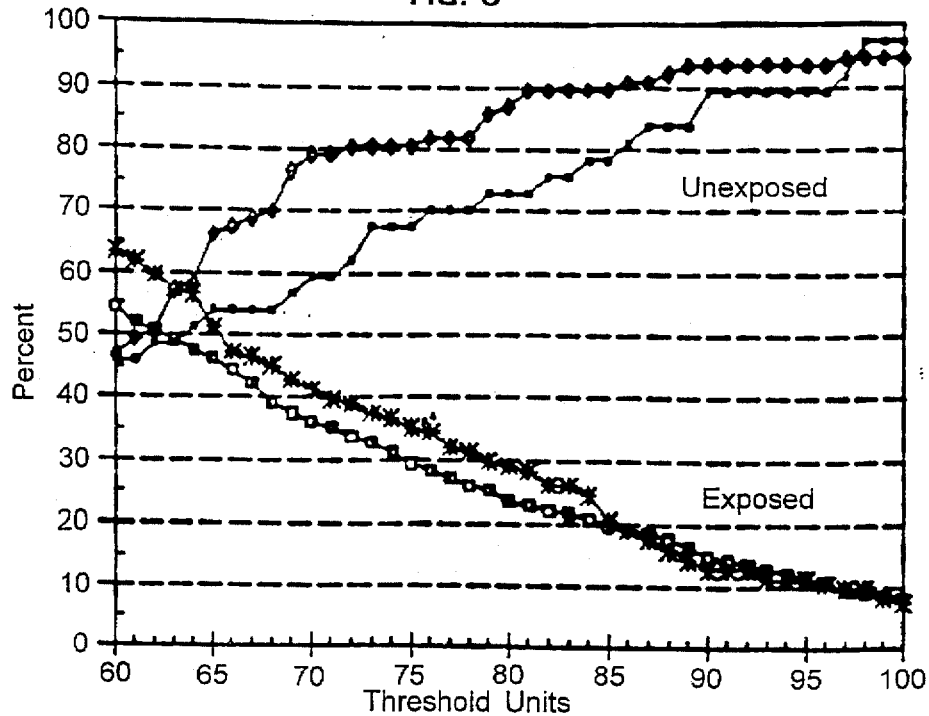
FIG. 9 is a specificity/sensitivity plot of G-actin in relation to benzidine exposure history.

The data were analyzed to determine optimal thresholds to use in interpreting findings among this cohort of workers. The ROC plot for DNA is shown in FIG. 8. FIG. 9 shows the corresponding ROC plot for G-actin. As with the DNA ploidy marker, the exposed and nonexposed populations differed in their distributions between the two populations. The units for G-actin are reported as the ratio to a standard cell population known to express elevated levels of G-actin, expressed as a percentage. The threshold chosen in this study defined a positive such that the mean G-actin content of a minimum of 20 exfoliated cells from a single slide was greater than 90 units. This definition of positive was used to derive the positive-negative findings listed in the tables.

A number of subjects had more than a single marker positive, and such occurrences were much more frequent than by chance (16-fold for all three markers), thereby supporting the association between markers and exposure. The numbers of samples positive for two and three markers respectively are shown in Table VIII by exposure and smoking.

TABLE VIII

Samples positive for two or three markers by exposure and smoking history.

| | Smokers | | | | Non-Smokers | | | |
|---|---|---|---|---|---|---|---|---|
| Group | G-Actin + DNA | DNA + M344 | M344 + G-Actin | All Markers Positive | G-Actin + DNA | DNA + M344 | M344 + G-Actin | All Markers Positive |
| Exposed | 10/368 2.7% | 5/384 1.3% | 8/368 2.2% | 3/365 0.8% | 3/121 2.5% | 2/130 1.5% | 5/121 4.1% | 2/119 1.7% |
| Controls | 1/69 1.4% | 0/73 0% | 1/69 1.4% | 0/69 0% | 1/36 2.8% | 0/39 0% | 1/36 2.8% | 0/36 0% |

Of particular interest were 22 subjects of the study who were p300/M344-positive. Each of these subjects was also positive for either G-actin or abnormal DNA. Thus, this particular marker seems to have a very strong association with other positive findings.

TABLE IX

Logistic regression analysis of multiply positive samples by other risk factors.

| Feature | G-Actin + DNA 15/579 | DNA + M344 7/619 | M344 + G-Actin 15/579 | All Markers Positive 5/594 |
|---|---|---|---|---|
| Pack Years | .0001 | .0001 | .0001 | .0001 |
| Years of Exposure | .0001 | .0001 | .0001 | .0001 |
| Prostatic Hematuria | .0008 | .0001 | .0001 | .0001 |
| Exposure Index | .4395 | .2907 | .9703 | .2831 |
| Hematuria | .8624 | .6397 | .9093 | .8119 |

The Cox Logistic Regression model was applied to the multiply-positive samples with results as shown in Table IX. The results were similar to those obtained with single markers. Pack years of smoking and years of exposure were the most significant variables, while prostatic hyperplasia was significant as well. Hematuria made no contribution to the model in this particular study, and the contribution of the exposure index was small.

TABLE X

Logistic regression analysis of Papanicolaou cytology comparing other markers and other risk factors.

| Feature | p Value Pap Cytology 48/687 |
|---|---|
| G-Actin Mean | .0001 |
| M344 Pos/10K | .0001 |
| DNA > 5C % | .1346 |
| Pack Years | .0002 |
| Years of Exposure | .0234 |
| Prostatic | .2661 |

TABLE X-continued

Logistic regression
analysis of Papanicolaou cytology
comparing other markers and other
risk factors.

| Feature | p Value Pap Cytology 48/687 |
|---|---|
| Hyperplasia | |
| Exposure Index | .9714 |
| Hematuria | .0974 |

The association of Papanicolaou cytology with the other markers and with other risk factors was also investigated using the Logistic Regression model with results as shown in Table X. There were 48 positive findings, with positive suspicious, and atypical all considered as positive findings in this analysis.

Preliminary data analyses have established that the marker set employed is capable not only of detecting tumors but of predicting tumors because the tumors that were found were from subjects in whom no tumors were evident at a previous screening.

Methods a. Quantitative Fluorescence Image Analysis. Three markers were simultaneously analyzed. Each sample was centrifuged and the pellet resulting was taken up in buffered fixative and frozen (−70° C.) until analyzed. This procedure preserves marker quantitation and cell morphology. To further minimize the number of inadequate samples, the cells in the sample were counted on a Coulter cell counter using algorithm that takes into account crystals, if present, small cells, such as lymphocytes, and large urothelial cells. This count is used to determine whether the cells will be aliquoted into one container or two. The samples are thawed, diluted with buffer, collected onto a filter and imprinted onto a special slide adapted for use on a Code-On automated stainer/labeler. These methods are described in more detail in the sections "Fixative/Preservative Solution" and "Slide Preparation".

The programmable robotics staining/labeling device precisely and reproducibly steps paired slides separated by a thin space through the reagents needed to label the slides with immunologic and dye reagents. Each slide was triple-labeled for, (1) DNA using 8.7 µM Hoechst 33258, (2) p300 using the M344 mouse monoclonal antibody direct-conjugated with Bodipy fluorochrome, and (3) DNase I (Molecular Probes) directly conjugated to Texas Red to detect G-actin. A corresponding negative control slide omitting primary antibodies was also prepared. All reagents had been optimized to achieve saturation. With each batch of slides, cell lines known to be high and low expressors for each quantitative marker were also included.

Figure 12A:
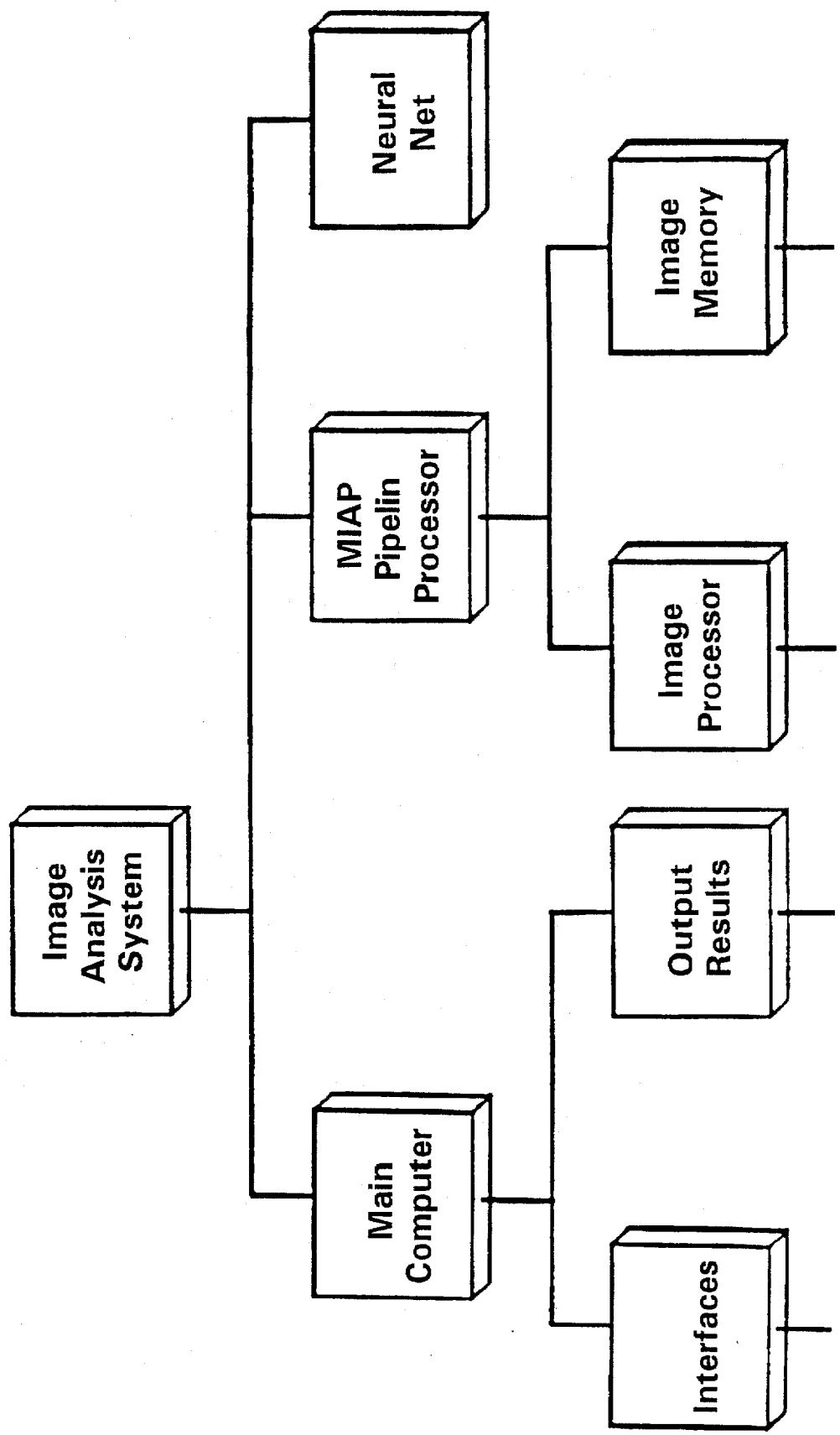
FIG. 12A is a partial schematic of an Image Analysis System showing main components.
Figure 12B:
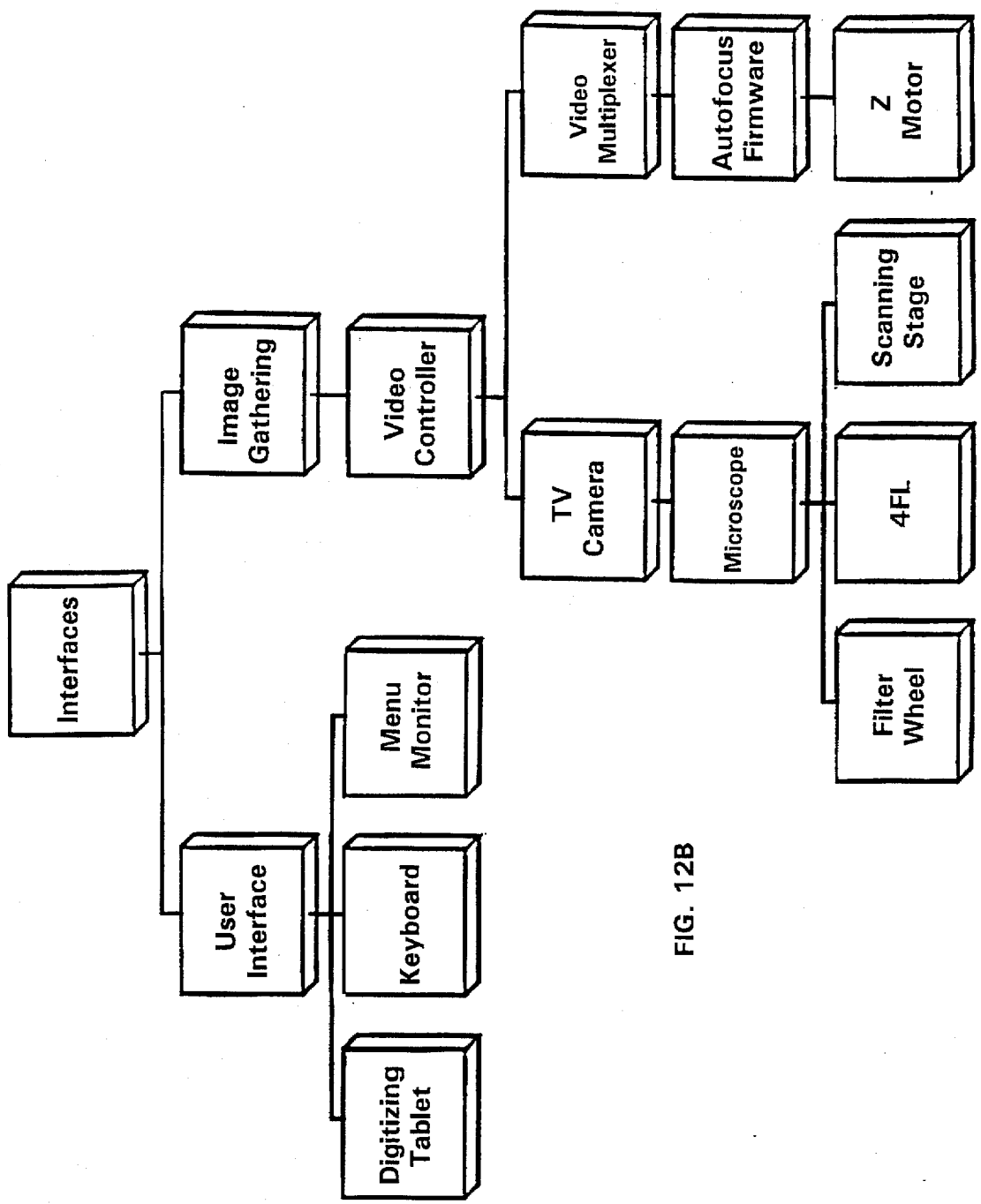
FIG. 12B is a partial schematic of Image Analysis System showing interface subunits.
Figure 12C:
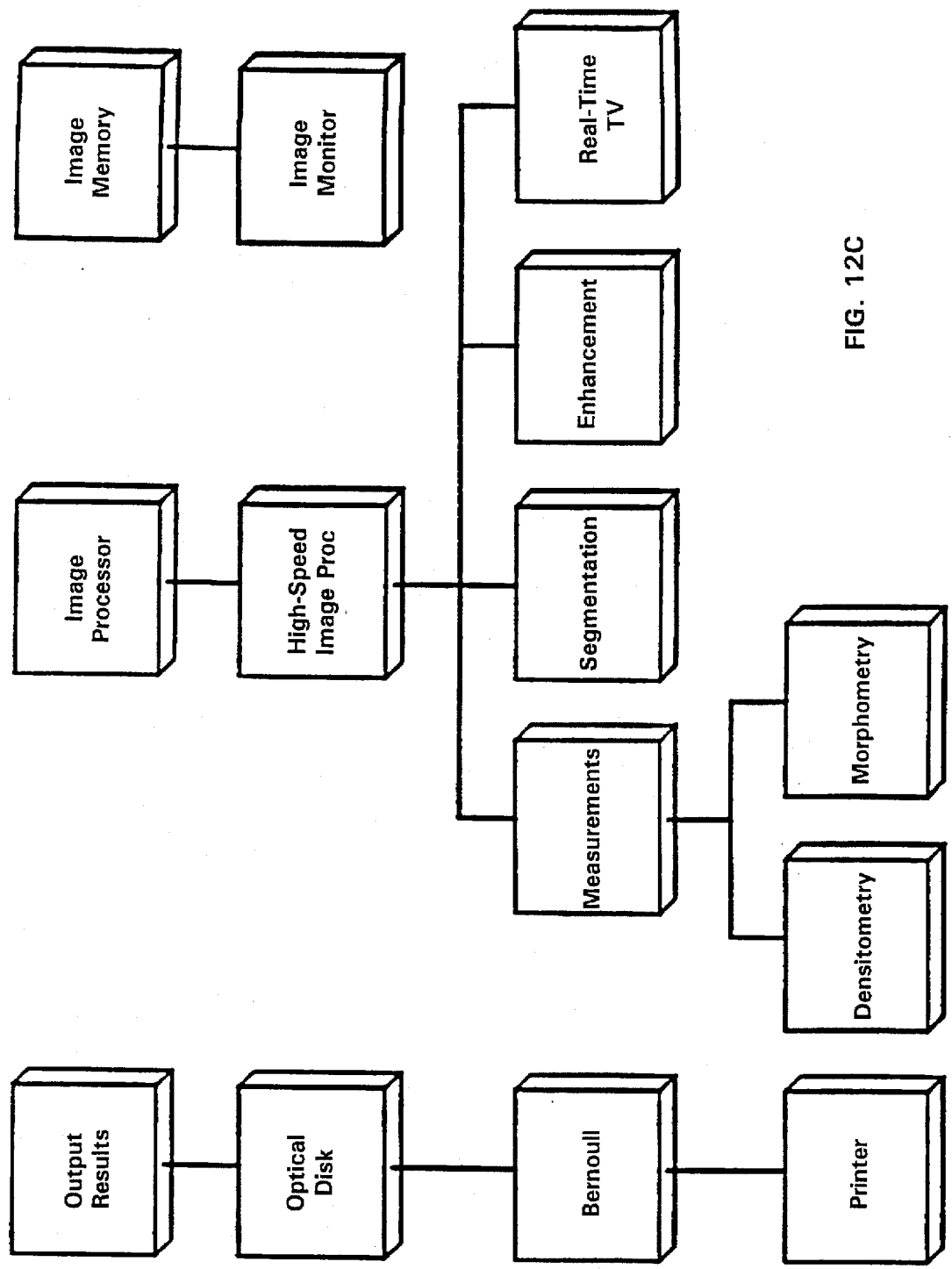
FIG. 12C is a partial schematic of Image Analysis System showing output, image processor and image memory subunits.

Markers were quantified on individual cells on a cell-by-cell basis for 50–100 cells per slide using a Zeiss IBAS image analysis system equipped for quantitative fluorescence. A schematic diagram of the IBAS system is shown in FIGS. 12A–C (neural net computer was not used in this example). In tumor biopsies, regions of tumor cells were specifically analyzed, but cells were randomly selected in nontumor control specimens. In both cases infiltrating lymphocytes or blood cells were specifically excluded. The images of labeled cells were captured and the intensity of each pixel (dot comprising the image) was converted to a digital grey level between 0 and 255. Immunofluorescence was measured as the integrated grey level (IGL) or averaged grey level (AGL). AGL is the average grey level of the pixels comprising an image and is proportional to the average concentration within a cell. IGL is the value obtained multiplied by the area of the cell image and is proportional to the total content of marker in each cell.

The immunofluorescence assays were calibrated against cell lines known to express high and low amounts of the proteins. A large number of slides were prepared from a single batch of each cell line. A positive (with primary antibody) and negative (without primary antibody) slide for each marker was included with each batch of patient samples, and the cells were labeled and analyzed as described. The IGL or AGL was corrected for extraneous background fluorescence by subtracting the mean IGL or AGL determined from approximately 100 cells on the negative control slide.

The p300 marker was scored visually by two independent observers. A sample was considered positive if more than two cells positive for p300 per 10,000 cells were found on the M344-labeled slide. The count of cells on the slide was obtained by the IBAS. The positive cells were manually confirmed. G-actin was approximately normally distributed. For G-actin, a sample was considered positive if the mean IGL was greater than 90% of the mean IGL of a positive-expressor cell line. Assays for p185 and EGFR have also been developed. For p185, the mean IGL of cells on the negative control slide is calculated and subtracted from the IGL of each cell on the sample side. The p185 shows a lognormal distribution. If the adjusted mean IGL significantly (t-test) exceeds the adjusted IGL of a low expressing cell line (3T3 SW480), the sample is labeled as positive. For EGFR, a histogram of normal cells from control patients is constructed, and the presence of cells above the upper limit of normal is used as an indicator of positive.

b. Papanicolaou cytology was performed using standard, routine urinary tract cytological methods.

c. Urinalysis and Hematuria Testing was performed using standard techniques, including a dipstick for heme. Urine sediment analysis was performed within 2 hours of collection of the sample.

Statistical Analysis

Preliminary statistical analysis of the decoded data from identified benzidine exposure, smoking, and prostatic hyperplasia as significant risk factors for the development of abnormal marker results. Not all dysplasias will necessarily progress to clinically detectable malignancy. Thus the number of marker-positive findings at time t will always be greater than the number of malignant lesions found in the same population and higher than the number of malignant lesions found upon subsequent follow up. In addition, only a portion of eventual disease, whether malignant or premalignant, results from known exposures, so that positive findings are expected in persons without known carcinogenic exposure.

Fixative/preservative solution

This fixative/preservative solution preserves the cells with retention of characteristic morphology and quantity and concentration and distribution of biomarkers in the cells while simultaneously inhibiting the formation of crystals in the urine. This process of inhibition of crystal formation is important because crystals can (1) prevent or interfere with adherence of cells to a slide, (2) lengthen the time necessary to prepare the slide for analysis, and (3) physically obscure the viewing of cells on the slide The benefits to the reduction of crystal formation in the sample are to (1) decrease preparation time, (2) decrease the number of unsatisfactory slides which are produced, and (3) increase the number of cells per microscope field on the slide.

A study was conducted in which 50 slides were prepared from urine samples fixated with the crystallization inhibiting fixative of the present invention, and separately 50 slides were prepared from urine samples fixated with a non-crystallization inhibiting control fixative (MOPSO with buffered ethanol, see, for example the reference by McGowan, et al., cited previously). The urine samples were taken from the sample population. On the slides using the crystallization inhibiting fixative, there was an average of 165 cells per $mm^2$. On the slides using the control fixative without crystallization-inhibiting agents, there was an average of 33 cells per $mm^2$. Thus, inhibition of crystallization improved adherence of cells to the slide by a factor of 5x.

The primary crystals inhibited by the method are common crystals comprising calcium and magnesium cations. Formation of certain rare crystalline forms may not be inhibited.

The term "inhibition of crystal formation" as used herein is defined as meaning the inhibition of the formation of crystals containing calcium or magnesium, or the solubilization such crystals which are already present, in urine samples which would otherwise form crystals under a range of temperatures including room temperature and refrigeration temperatures (e.g., about 4° C.) and during a range of time periods including immediately after collection of the sample, after 24 hours and after 48 hours or later if fixation was performed using a commonly used non-crystallization inhibiting composition such as buffered alcohol.

Inhibition of crystal formation allows the urine to be stored and shipped with its cells preserved. The fixative is designed to be mixed in equal volume with the urine. In a preferred version, the fixative consists of four components with an optional fifth.

A first component is a preservative which kills most bacteria and other microorganisms and inhibits endogenous enzymatic degradation. A specific preservative is ethanol (50% v/v). A second component is a buffer to adjust the pH of the solution to help retain morphology, the buffer having a pK preferably in the range of 6-7 but alternatively in the ranges of 5-6 or 7-8. A preferred buffer is 2-N-morpholino-2-hydroxypropanesulfonic acid (MOPSO), 0.05M, which is also effective within a range of from about 0.01M to 0.2M.

Other buffers in the preferred pk range are N-[2-Acetamido] -2-aminoethanesulfonic acid) (ACES), (N-[2-Acetamido] -2-iminodiacetic acid) (ADA), (bis[2-Hydroxyethyl]imino-tris[hydroxymethyl]methane (BIS-TRIS), (2-[N-Morpholino]ethanesulfonic acid (MES), and (Piperazine-N,N'-bis[2-ethanesulfonic acid] (PIPES). Buffers in the alternate pk range of 7-8 are (N,N-bis[2-Hydroxyethyl]-2-aminoethanesulfonicacid) (BES), (3-[N, N-bis(2-Hydroxyethyl)amino]-2-hydroxypropanesulfonic acid) (DIPSO), (N-[2-Hydroxyethyl]piperazine-N'-[3-propanesulfonic acid] (EPPS), (N-[2-Hydroxyethyl] piperazine-N'-[2-ethansulfonic acid] (HEPES), (N-[2-Hydroxyethyl]piperazine-N'-[2-hydroxypropanesulfonic acid]) (HEPPSO), (3-[N-Morpholino]propanesulfonic acid) (MOPS), (Piperazine-N,N'-bis[2-hydroxypropanesulfonic acid]) (POPSO), (3-[N-tris(Hydroxymethyl)methylamino]-2-hydroxypropanesulfonic acid) (TAPSO), and (N-tris [Hydroxymethyl]methyl-2-aminoethanesulfonic acid) (TES). These buffers are commercially available from a source such as Sigma Chemical Co.

A third component is a substance for inhibiting formation, and for solubilization, of crystals. Where the preservative is ethanol, the substance should be soluble in ethanol. A specific example is the dipotassium salt of ethylenediaminetetraacetic acid (EDTA). Other EDTA salts of cesium, rubidium, and various organic cations may also be effective, as are other salts, derivatives and analogs.

A fourth component is a substance to maintain the ionic strength within limits that inhibit cell distortion. A specific example is KCl, 0.10M, and it must be both soluble in the preservative (e.g., ethanol) and not cause precipitation of the solubilizing agent (e.g., potassium EDTA). Alternatively, the substance to maintain the ionic strength may be an additional amount of the buffer previously added or another compatible buffer.

A fifth component, which is optional, is a biocide to prevent the growth of certain resistant bacteria and other microorganisms. A specific example is $NaN_3$, sodium azide, 0.1% (w/v). This biocide component is optional depending on the time lapse between collection and shipment and analysis. The fixative is prepared by mixing the four aqueous components and adjusting the pH to 6.5, then adding an equal volume of pure ethanol.

Additional fixation to ensure preservation of protein markers can be achieved by first mixing the urine sample with a formaldehyde solution to a final concentration of 0.5% (w/v) and allowing the urine/formaldehyde mixture to stand for a time period, e.g., 15 minutes, prior to addition of the above fixative.

Figure 10A:
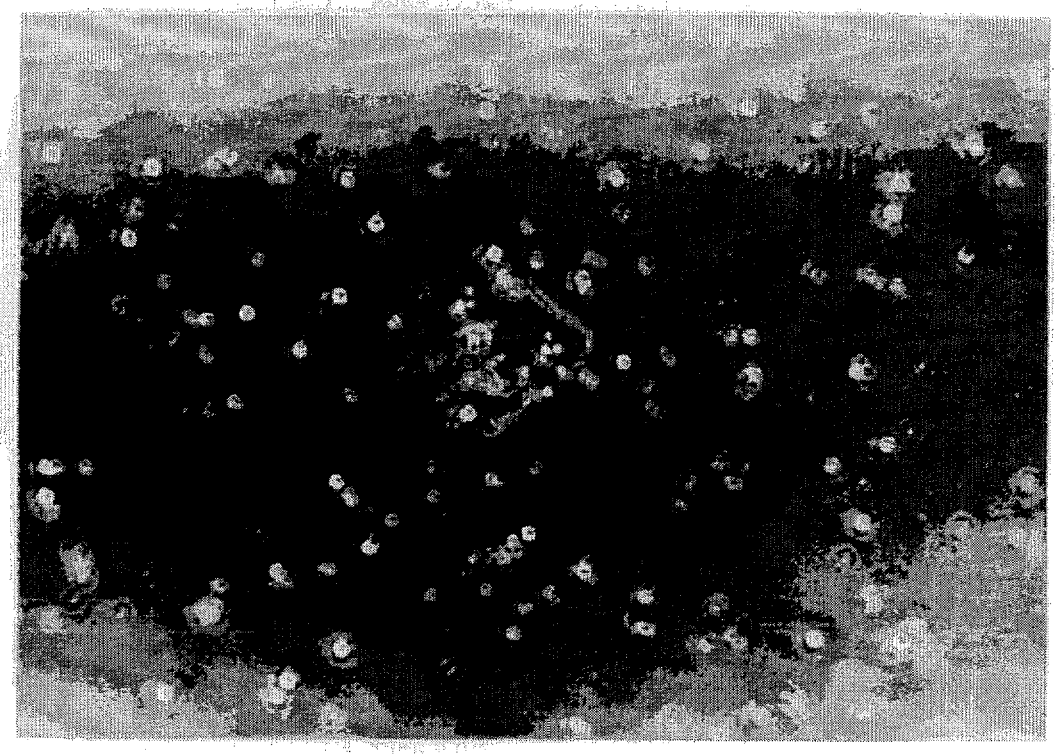
FIG. 10A is a phase contrast photomicrograph of a urine sample which was fixated with a non-crystal inhibiting fixative.

The efficacy of the crystallization inhibiting formulation of the present invention is shown in the photomicrographs of FIGS. 10A and 10B and 11A and 11B. The fixative of the present invention was compared to a non-crystallization-inhibiting fixative. A first urine sample was collected. A portion of urine sample was fixated with fixative of the present invention having the crystallization inhibiting fixative comprised of 50% ethyl alcohol and MOPSO buffer. The first urine sample contained an abundance of oxalate. A phase contrast photomicrograph of the urine sample fixated with the non-crystal inhibiting fixative is shown in FIG. 10A. A phase contrast photomicrograph of the portion of the urine sample fixated with the crystal inhibiting fixative of the present invention is shown in FIG. 10.

Figure 11A:
FIG. 11A is a phase contrast photomicrograph of a second urine sample which was fixated with a non-crystal inhibiting fixative.
Figure 11B:
FIG. 11B is a phase contrast photomicrograph of the same urine sample as FIG. 11A except it was fixated using a crystallization-inhibiting means.

Similarly, a second urine sample, containing an abundance of amorphous phosphate crystals was collected. A portion of the second urine sample was fixated with the non-crystal inhibiting fixative and another portion of the second urine sample was fixated with the crystallization inhibiting fixative of the present invention. A phase contrast photomicrograph of the portion of the second urine fixated with the non-crystal-inhibiting fixative is shown in FIG. 11A. A phase-contrast photomicrograph of the portion of the second urine sample fixated with the crystallization inhibiting fixative is shown in FIG. 11B.

Figure 10B:
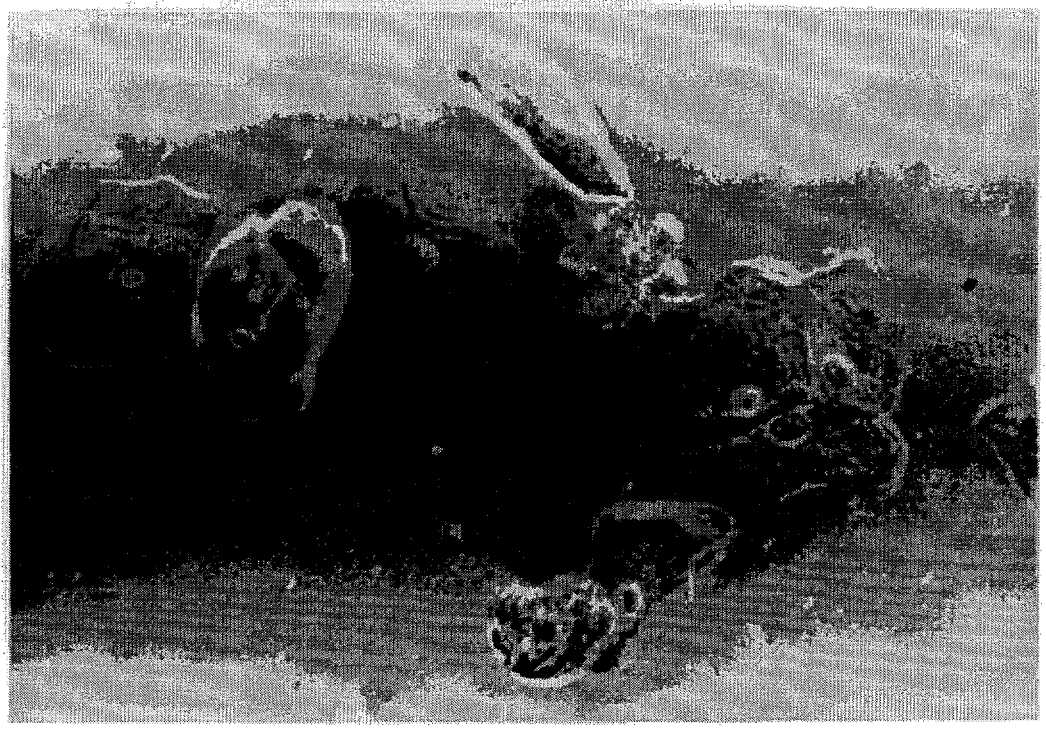
FIG. 10B is a phase contrast photomicrograph of the same urine sample as FIG. 10A except it was fixated using a crystallization-inhibiting means.

FIG. 10A shows a urine sample containing an abundance of oxalate crystals, interference of the cells on the slide by the crystals present, and only about 1 to 2 cells per microscope field. Alternatively, FIG. 10B shows a urine sample containing only rare crystals and containing significantly more cells than the number indicated on the slide micrograph of FIG. 10A.

FIG. 11A shows a urine sample containing an abundance of amorphous phosphate crystals, obfuscation of the cells on the slide by the crystals present, and only about 1–2 cells per microscope field. Alternatively, FIG. 11B shows a urine sample containing only rare crystals and containing substantially more cells than the number indicated on the slide micrograph of FIG. 11A, and which are substantially more visible.

Sample Slide Preparation

In order to prepare a sample for slide preparation, it must be thawed to room temperature if previously frozen. Label a washed 50 ml centrifuge tube for each sample. Label an Accu-vial for each sample and fill with 20 ml of Isoton using a repipettor. When the sample is thawed, shake it vigorously and pour it into a respective 50 ml centrifuge tube. With a clean disposable pipette, vigorously aspirate the cell suspension to disperse the clumps. Put approximately 2 ml of filtered DDW solution into the empty freezer vial. Aspirate the solution three or four times to break up the clumps. Transfer the solution to a respective 50 ml centrifuge tube containing the thawed cells. Fill to the 45 ml mark with 50% of EtOH +5 mM EDTA solution. Shake the 50 ml tubes and let stand at room temperature for 20 minutes.

In preparation of analyzing the sample with a Coulter counter, aliquot 0.5 ml from the sample in the 50 ml tubes into filled Accuvials. Prepare the Coulter Counter as per protocol. Perform a background count. If the reading is less than 5, proceed. If the reading is more than 5, wait a period of time for any bubbles in the blank to disperse and count again. If the reading is still more than 5, clean the aperture, rinse the probe and refill the blank container with Isoton after rinsing the container thoroughly with DI water. Gently invert a sample three or four times. Read the sample on the Coulter Counter at the following lower thresholds: 5.138 microns, 10.03 microns, and 15.00 microns. If the 5.138 micron count is equal to or greater than 1000, centrifuge the sample again in the 50 ml centrifuge tube. Pour off the superatant. Raise to 45 mls with 50% of the EtOH +5mM EDTA solution as before. Let the sample sit 20 minutes at room temperature. Recount on the Coulter as before.

To apply a portion of the cell sample to a slide, mount an 8 micron Nucleopore (or polycarbonate) filter on the Milli-pore Filter Apparatus using the small bore base with a 15 ml acid cleaned funnel, taking reasonable care to center the filter on the fritted base, removing all the wrinkles. Mount the funnel such that the filter is not moved or wrinkled. Shake the sample vigorously. Pour the calculated volume into the funnel. Note: If the count at 5.13 is >400, double the volume. Using the gentle vacuum, draw down the sample in the funnel to just above the filter. Pour 10 mls of the DDW+5 mM EDTA solution into the funnel. Draw the liquid in the funnel down to the filter with the vacuum, being sure not to air dry the filter (go slowly near the end). Pour 5–10 mls Saccomanno Fixative into the funnel. Vacuum 1–2 ml through then let it stand 2 minutes. Label two polylysine coated Probe-On slides with the sample Lab Number and the Study Number in pencil. Label one slide as positive (+) and the other slide as negative (–). Place the (+) slide on the imprint guide. Put a couple of drops of DDW on the (–) slide. When the time is up, apply the vacuum to the funnel removing the fluid such that the bottom of the meniscus falls just below the center of the filter, taking care not to air dry the filter (filter slowly near the end). Quickly remove the funnel by carefully tilting it back and away being sure the filter is left on the stand.

Grasp the filter with a clean pair of filter forceps. Invert the filter and center it on the (+) slide aiming for the target of the imprint guide. Place a folded dampened Kimwipe over the filter and the slide, then press gently with the side of the hand for approximately 7 seconds. Peel back the filter with filter forceps. Lay the filter cell side down on the drop of water on the (–) slide. Quickly spray the (+) slide with Carbofix-E. Press the filter on the (–) slide with a folded Kimwipe for 7 seconds. Peel back the filter and spray the slide with Carbofix.

If enough of the sample is left to at least double the amount used to make the slide, check the slide for the correct number of cells under a microscope and remake the slide with an adjusted volume if too sparse or too dense. Record the final volume used to prepare the imprint on the prep worksheet. Freeze the imprinted slides at −20° C. in numerical order.

Freezing Leftovers:

The volume must be at least the amount used to prepare one slide from the prep worksheet in order to be useful in the future. Centrifuge the sample at 600 g for 10. minutes. Pour off the supernatant. Transfer the pellet to a 5cc cryovial labeled with the lab number and the study number. Place in the refreeze box recording box. Freeze the samples at −70° C.

Reagents:

5 mM EDTA DDW solution: 7.44 g EDTA disodium salt in 4000.00 ml of deionized distilled water. Stir until dissolved. Adjust the pH to 5.5. Filter through a 0.22 Am magna nylon filter. The solution is stable for 1 week at 4° C. Alternately, the filtered solution may be filtered and stored at −20° C. When ready to use, thaw and adjust pH prior to use.

50% ETOH in 5mM EDTA solution: 7.44 g EDTA disodium salt and 1894.74 ml distilled deionized water. Filter 2105.26 ml 95% EtOH through a 0.22 Am nylon filter. Stir the EDTA solution until dissolved. Adjust the pH with 1N HCl to 5.5. Add to the filtered EtOH solution by adding the EDTA solution to the filter apparatus and filtering.

Modified Saccomanno Fixative:

Combine 20 ml of Polyethylene glycol (PEG) 1540 (e.g., Union Carbide), 516 ml of 95% ETOH, and 464 ml of Buffered Filtered Saline (BFS). Melt PEG at 600C. Prepare 50% ETOH solution. Slowly add 20 ml of melted PEG solution to the ethanol solution while stirring. Stir for one hour. Store at room temperature.

To Prepare the Poly-L-lysine Coated Slides:

Load the slides in the slide rack. Wash the slides by soaking one hour in hot 2% Alconox solution, rinsing one hour in running hot water, and rinsing one hour in running distilled water. Dip the washed slides two times in 0.25 Ammonium Acetate. Dip two times in distilled water. Soak in poly-L-lysine for 10 minutes at room temperature. Air dry in dust-free environment or in 50° C. oven. Store in dust-free boxes indefinitely. The Poly-L-lysine working solution may be stored at 4° C. and reused for 1000 slide capacity.

Materials for coated slides:

Combine 0.1 g of poly-L-Lysine (e.g., Sigma #1524, MW>300 KD) and 2000.0 ml 10 mM Tris-HCl buffer (pH 8.0) to make the Poly-L-lysine working solution.

Combine 2.42 TRIZMA Base (e.g., Sigma Chemical Co. #T-1503) with 2000.0 ml distilled $H_2O$) to make 10 mM TRIS Buffer. Titrate to pH 8.0 with 1.0N HCl.

Combine 19.27 g Anhydrous Ammonium Acetate and 1000 ml of distilled $H_2O$) to make 0.25M ammonium Acetate.

OFIA Software and Methodological Description

The image analysis system consists of an epi-fluorescence microscope equipped with motorized stage, autofocus mechanism, filter wheel containing various degrees of interference neutral density filters, custom built 4FL excitation/ emission filter changer, motorized shutters and objective magnification changer (FIGS. 12A–C). All microscope components are controllable by software from the IBAS console as well as manual controls at the microscope. The software applications developed for this instrument use some common modules i.e. initialization of all motors, scan parameters, case file creation, restoration of incomplete runs, location of first field, automatic threshold selection, DNA scene segmentation, artifact rejection, DNA quantification, image clipping, image review and rejection, and image and data storage. The features selected for measurement, pre-processing of images, scene segmentation, threshold selection, and which constitute features of a cell of a desired type, are determined by the specific marker of interest.

Figure 13:
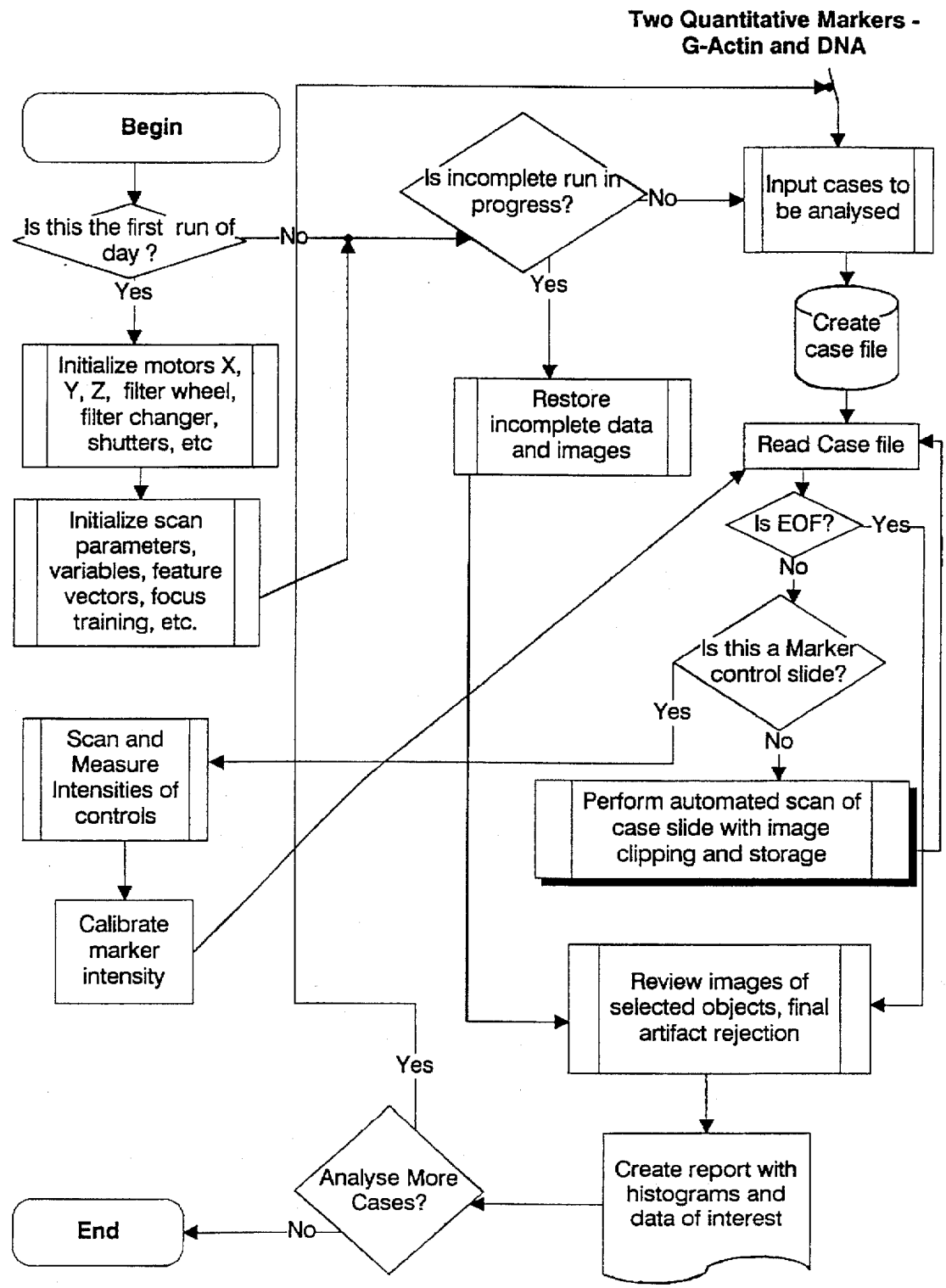
FIG. 13 is a schematic of software-controlled quantitative fluorescence image analysis with G-actin and DNA as markers.
Figure 14A:
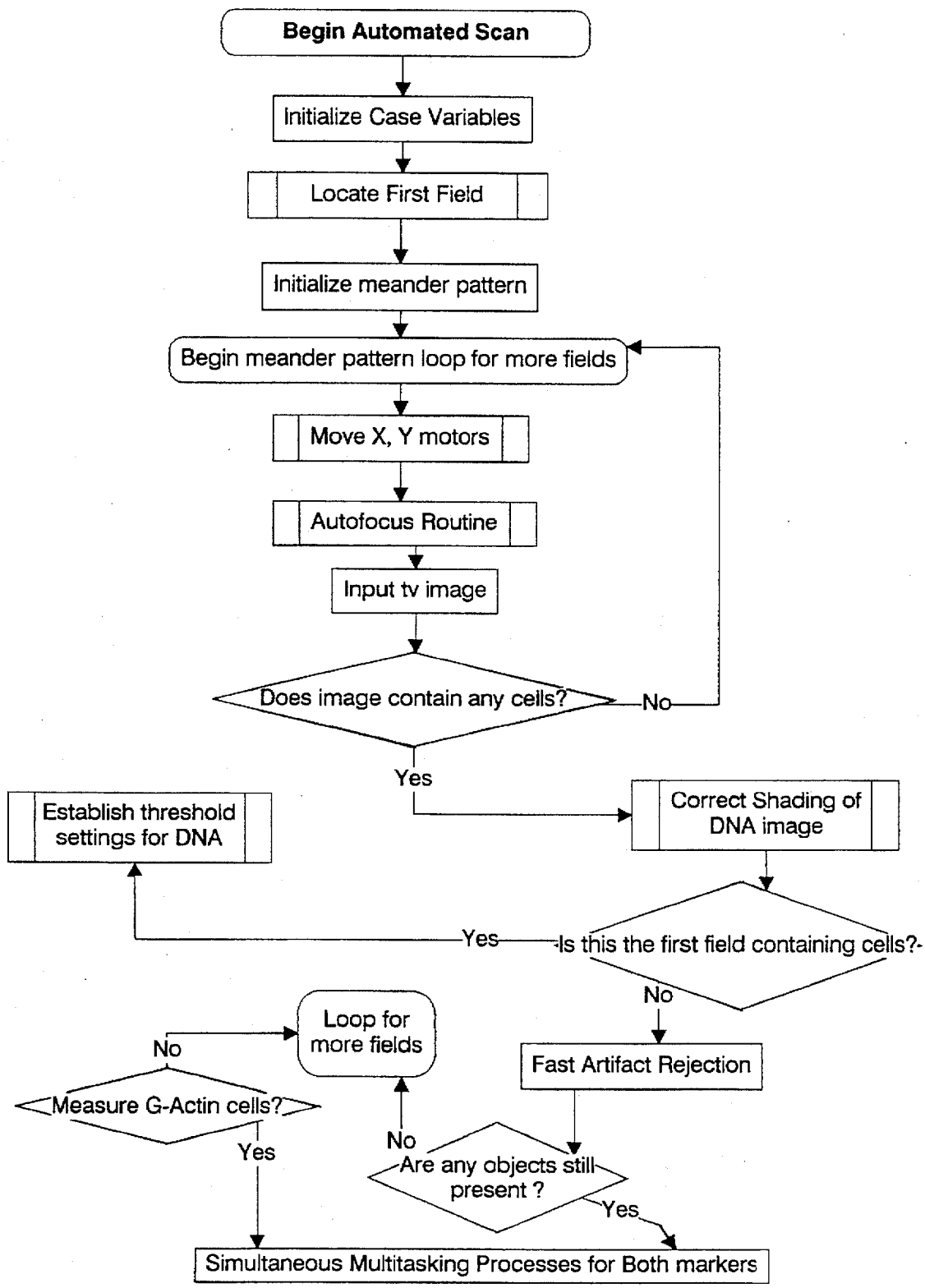
FIG. 14A is a schematic of the first stage of automated scan of slide with image clipping using G-actin and DNA.
Figure 14B:
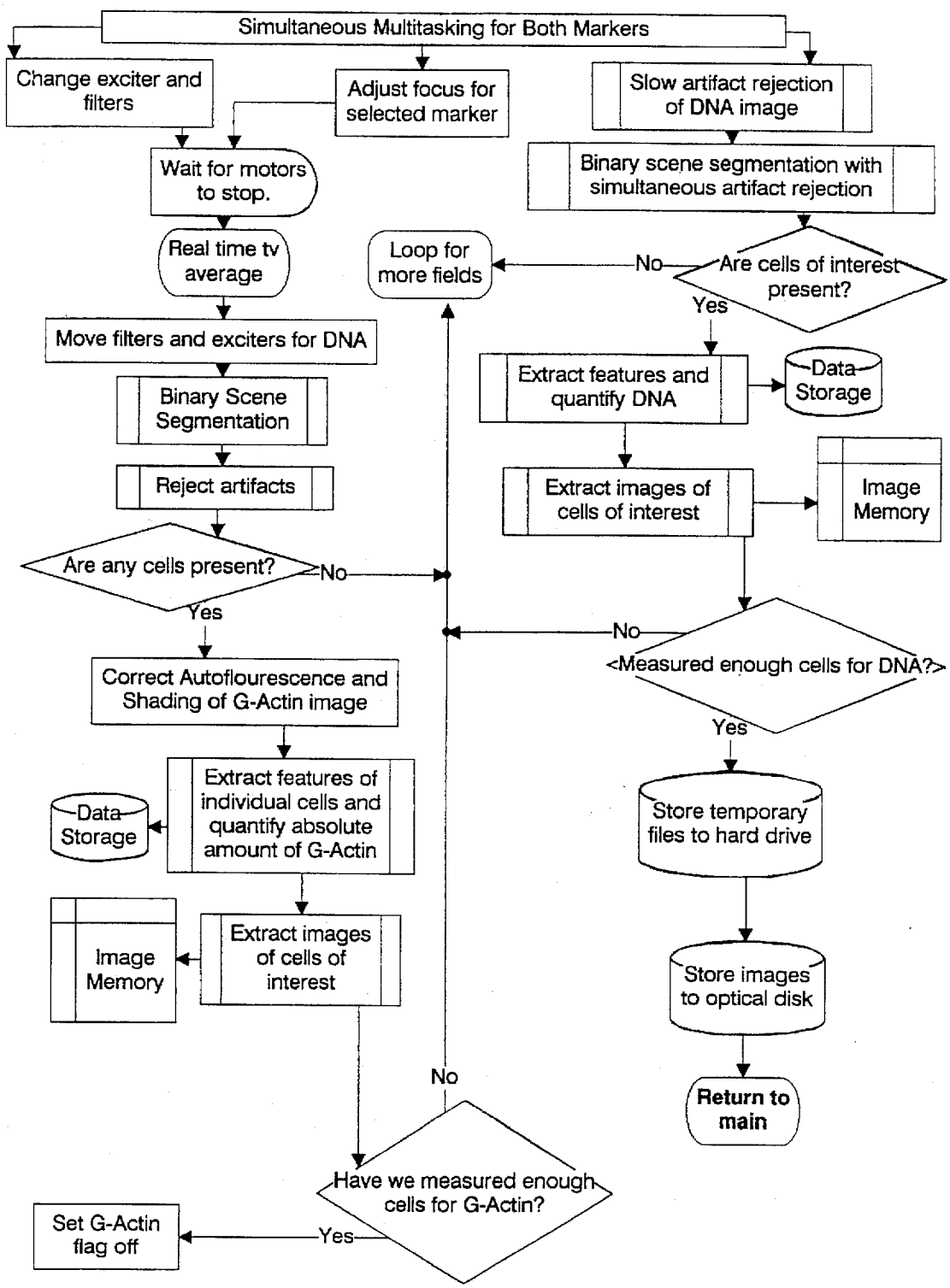
FIG. 14B is a schematic of the second stage of automated scan of slide with image clipping using G-actin and DNA.

An example of the program flow for a double-label assay, such as for DNA and G-actin is shown in FIGS. 13–14B. Briefly described, all motors are initialized when the instrument is powered up. In this process, home is located and defined for all motors and methods of communication to devices are established where appropriate. The meander pattern desired, optimal neutral density filters and exciters for each marker, and number of desired images of each marker are input by the user. The optimal focus is established in a brief training session for DNA. The cases loaded on the multiple position slide stage are then input into a scroll screen customized for quick entry. This information includes the filenames to be used for data and image storage, laboratory accession numbers to be stored with individual cell measurements, and patients names for each loaded stage position.

Upon completion of data entry, the software takes control and operates unattended until all cases have been completed (FIGS. 14A–B). During this time, selected features are measured and stored in temporary databases while images are clipped and stored to optical disk. The scan on each case continues with movement of the X and Y motors, focus, image capture, artifact rejection, image enhancement of each field for both markers simultaneously until enough cells have been measured (i.e., definitive positive or the entire slide).

The operator is then presented with a gallery of selected cells in order to exclude additional artifacts for each case. Alternatively, the gallery is sent to a neural net computer trained to exclude additional artifacts. The manual operation is controlled by the digitizer with a point and click approach to each image. The final histogram is presented with options to adjust the DNA 2C peak based on internal control cells if desired. Rejection of artifacts for both markers is included with subsequent production of the final report on a laserjet printer. Permanent data-bases are created and stored in the data path directory. The program then loops back to the case load module allowing additional slides to be analyzed.

In the event that a power failure occurred or the software is terminated while analyzing samples, a module is included to restore incomplete data in which temporary files created during the scans are restored, images reviewed, final reports generated, and permanent databases created.

Figure 15:
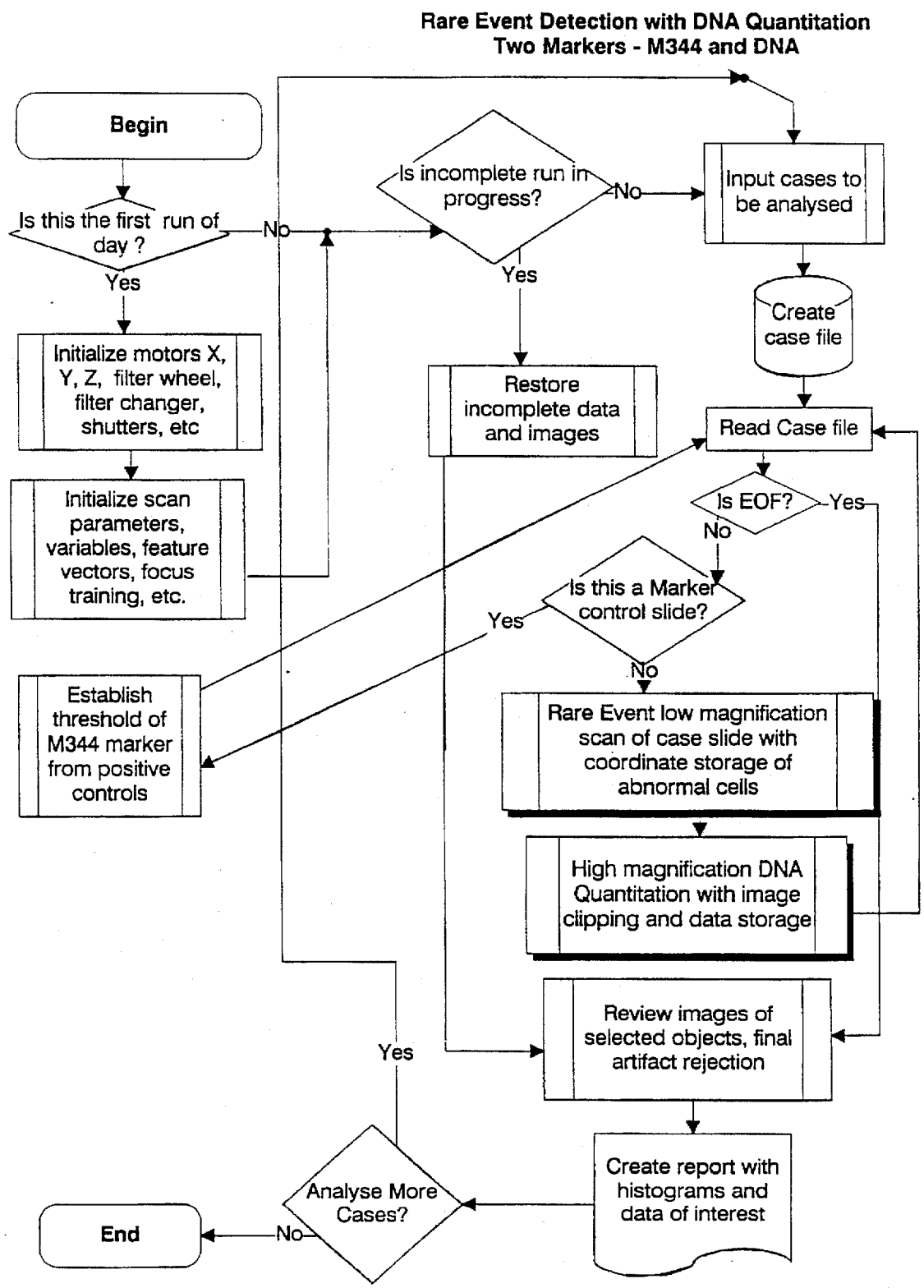
FIG. 15 is a schematic of software-controlled "rare-event" quantitative fluorescence image analysis using M344 and DNA.
Figure 16A:
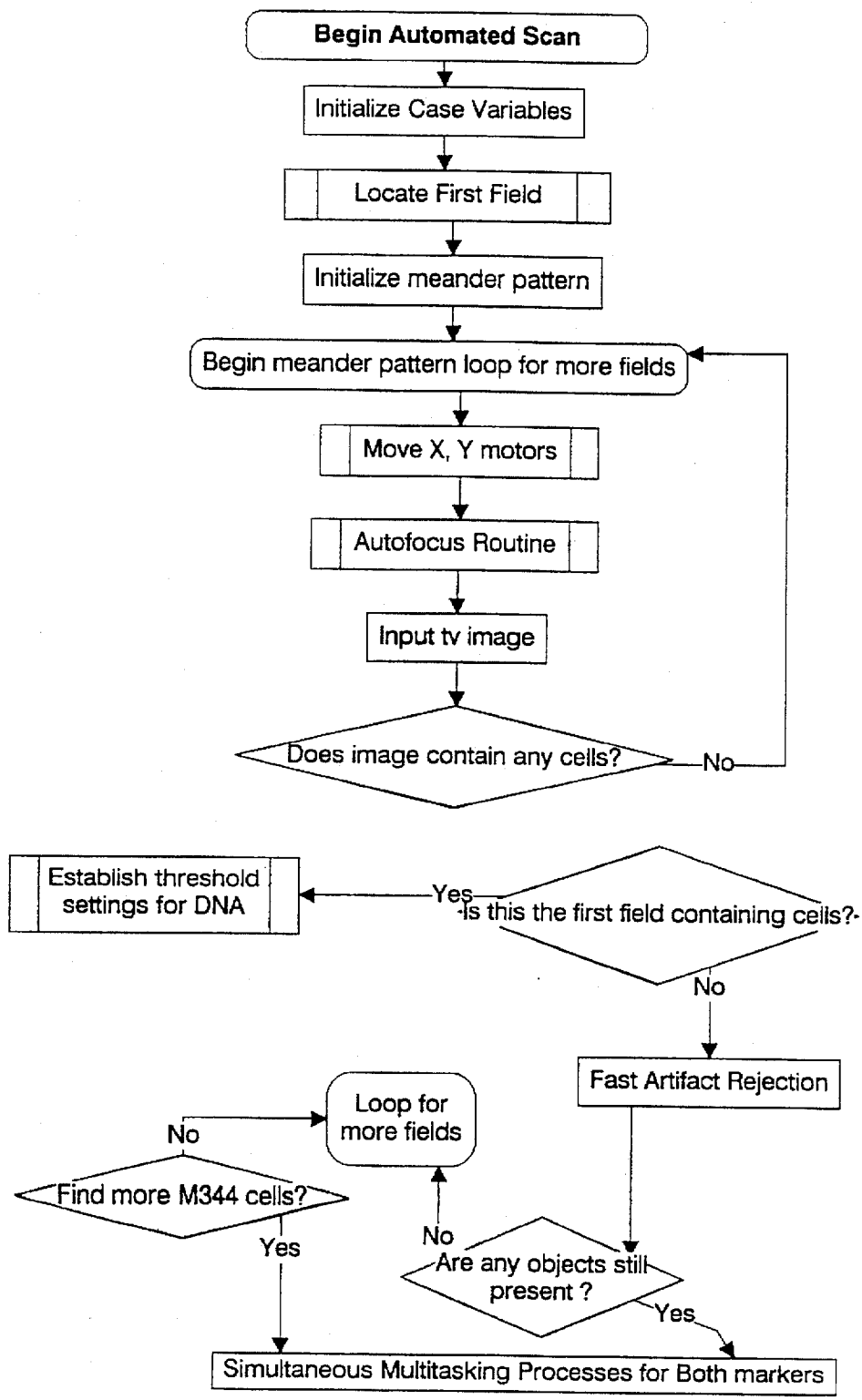
FIG. 16A is a schematic of the first stage of "rare-event" scanning at low magnification.
Figure 16B:
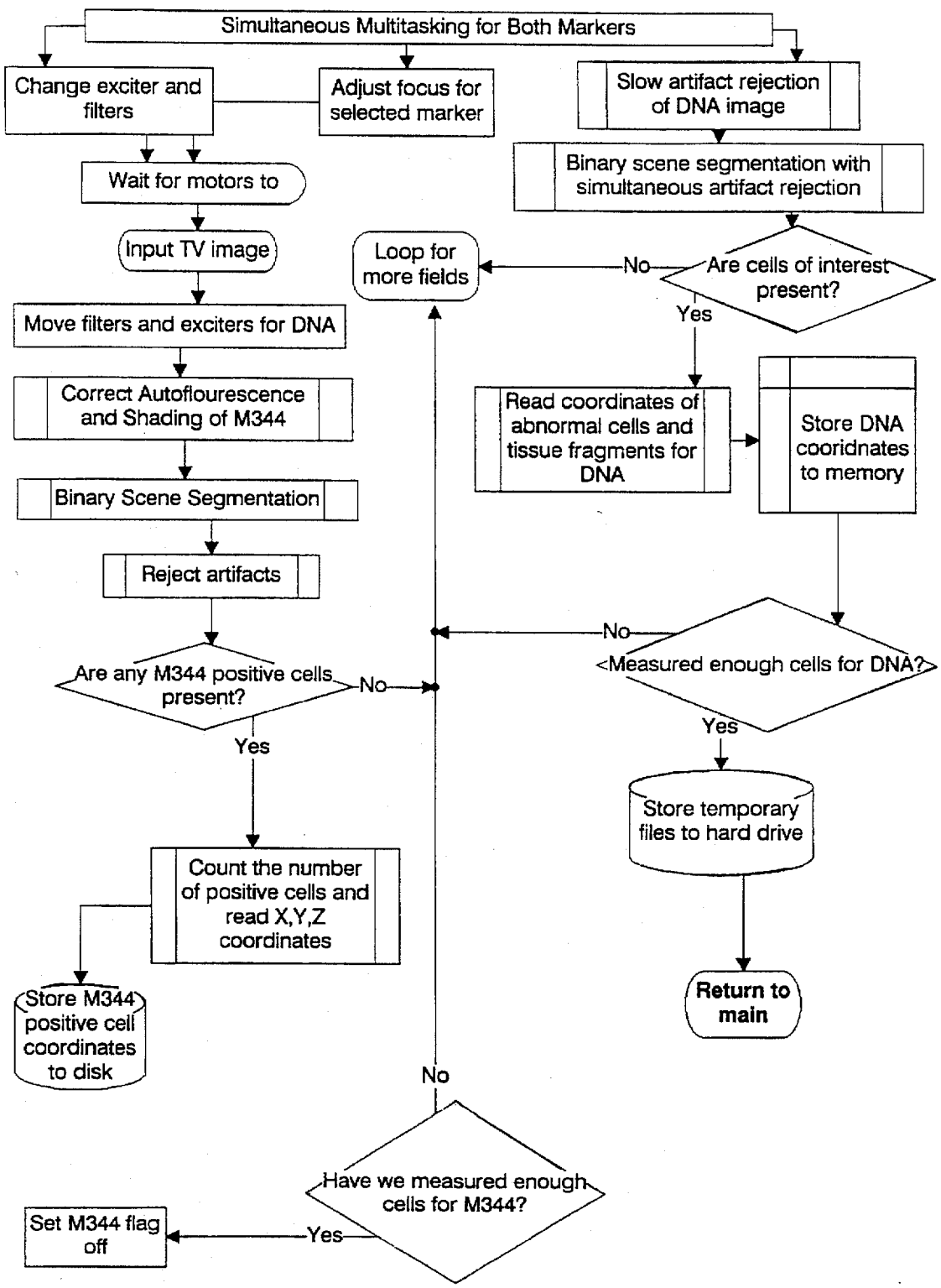
FIG. 16B is a schematic of the second stage of "rare-event" scanning at high magnification.
Figure 17:
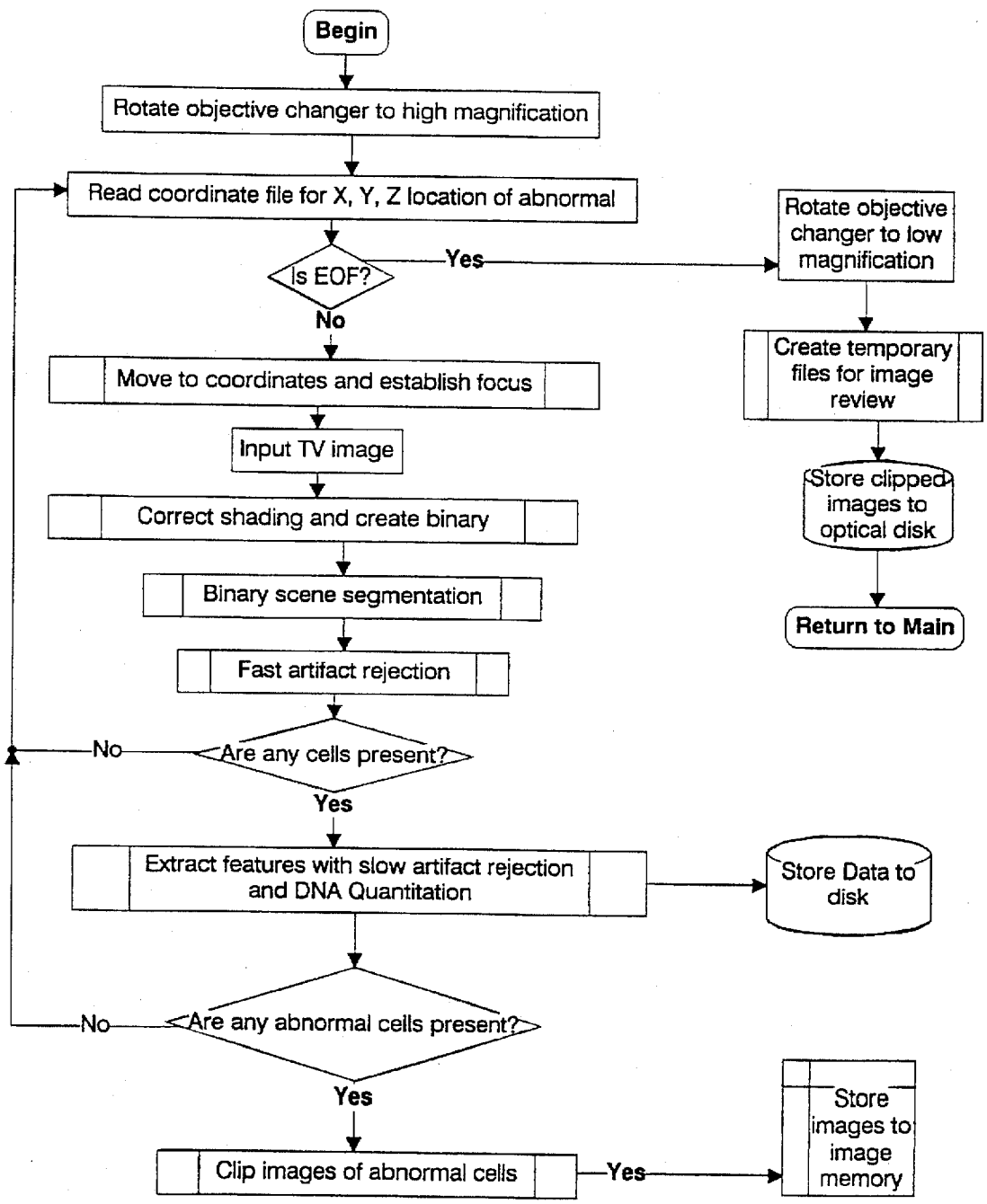
FIG. 17 is a schematic of "rare-event" scanning and DNA quantitation at high magnification using M344 and DNA.

The dual-marker software module for rare event scanning (M344-DNA) (FIG. 15) is similar to that of G-actin/DNA except that two passes are made on each slide during M344/DNA analysis with the first pass performed at low magnification (FIGS. 16A–16B) and the second pass at high magnification (FIG. 17).

This software is capable of locating events that occur in 2 per 10,000 cells. M344 is scored as a presence or absence marker with the number of events of expressing cells among the total number of epithelial cells calculated.

Figure 18:
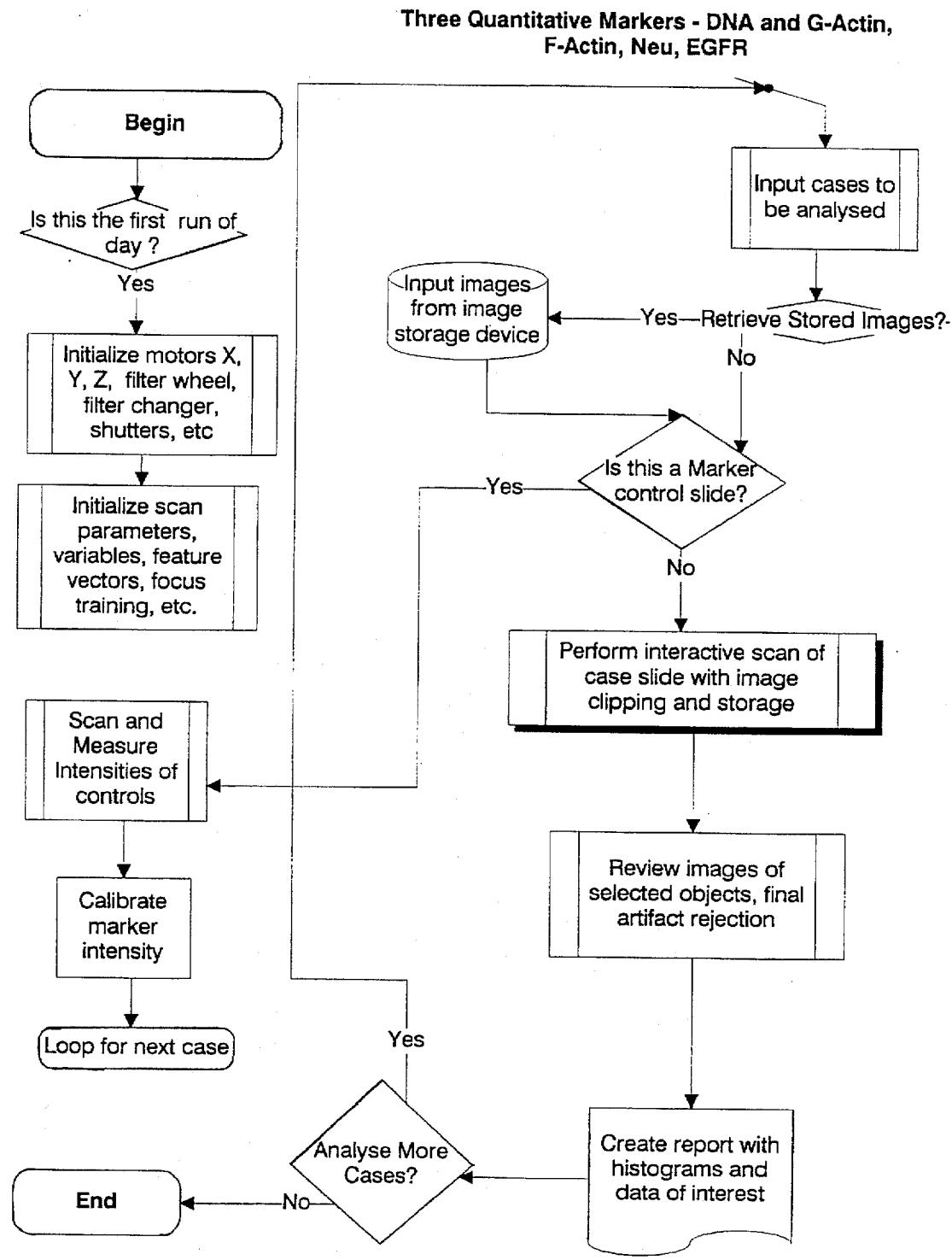
FIG. 18 is a schematic of software-controlled quantitative fluorescence image analysis with DNA and two other markers.
Figure 19A:
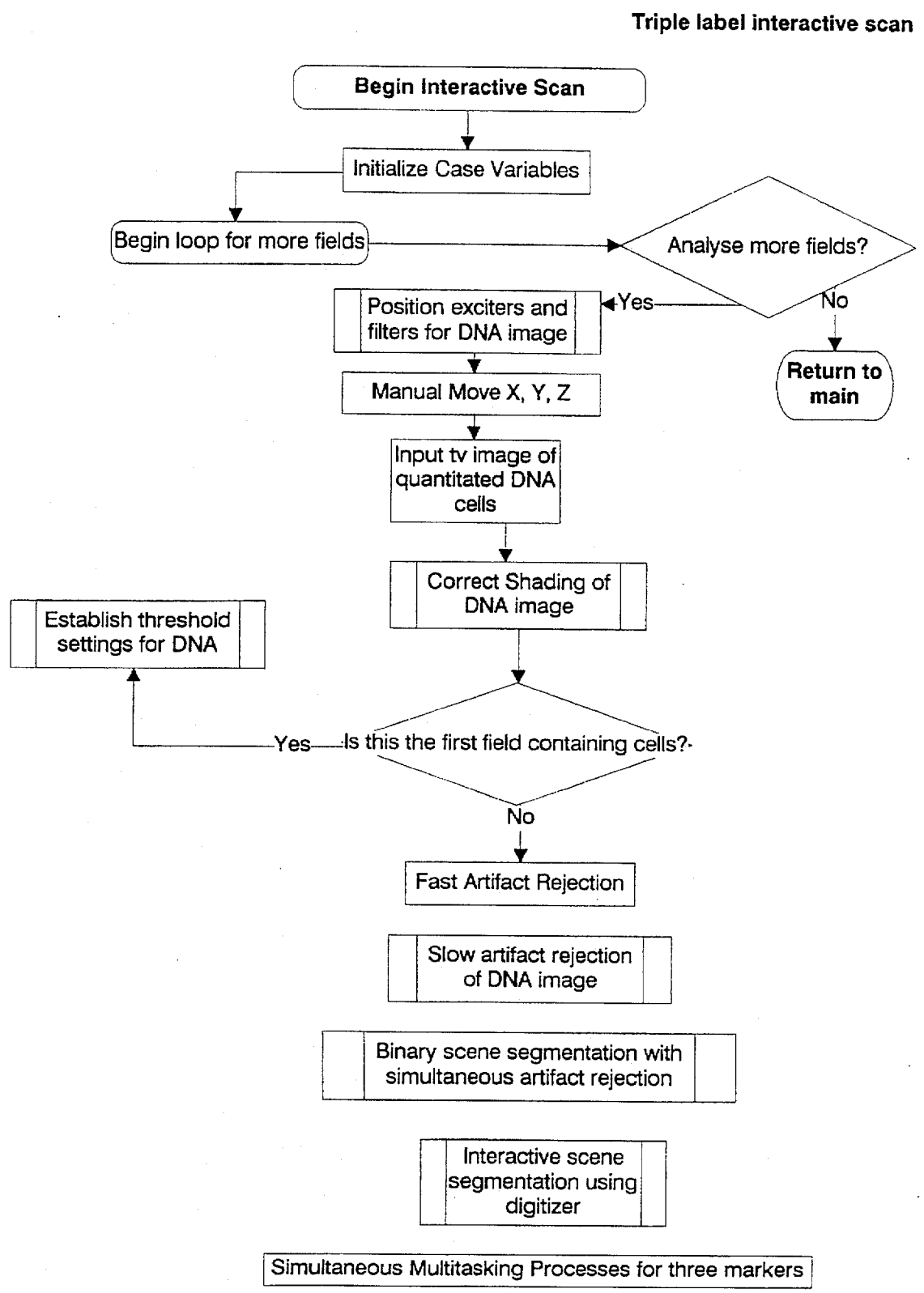
FIG. 19A is a schematic of the first stage of triple label scan.
Figure 19B:
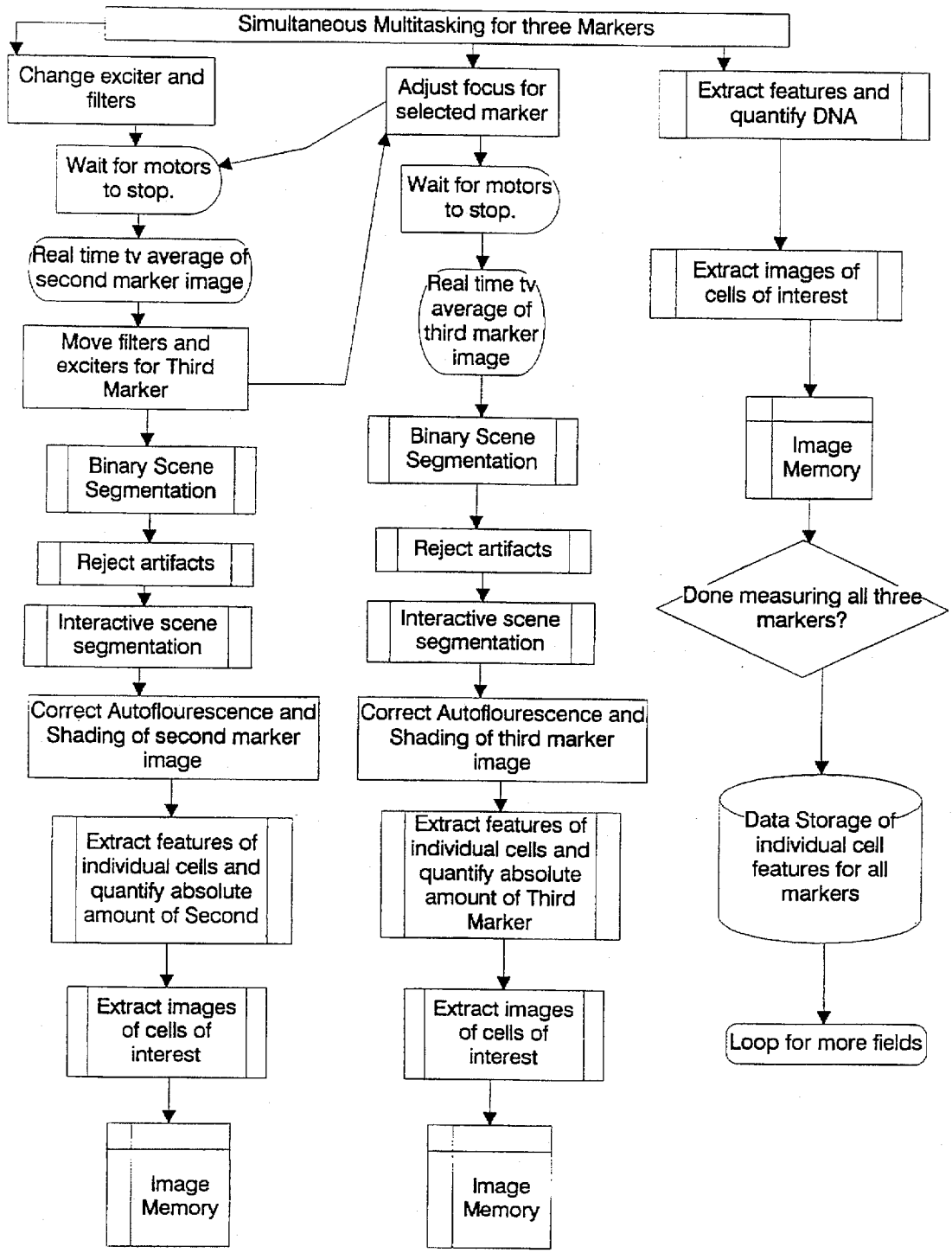
FIG. 19B is a schematic of the second stage of triple label scan.

The triple label software (FIG. 18) for touch preps has been designed to be interactive with the user in selection of cells and fields. It has additional features which allow the user to separate cells in tissue fragments using the digitizer. The three markers from each selected cell can be simultaneously measured with data and image storage if desired (FIGS. 19A–B). The software allows for image retrieval of stored images or direct image capture of live images from the microscope. Data analysis is also interactive with user selected parameters, scales, and three-dimensional histograms of selected parameters.

Referring in more detail to FIGS. 16A–B, the Rare Event scanning begins at low magnification. A portion of the prepared slide, such as a single field at low power is located and irradiated with a wavelength of light effective in irradiating the dye labeled to DNA. The resulting field image of the microscope field is digitized and analyzed for object images which are images of objects within the criteria established for cells. If the field image is the first which appears to contain cells, a grey value threshold for DNA is calculated. Another review step of the field image is conducted by the microscope wherein object images which exceed a predetermined size threshold or which are smaller than a minimum size threshold are rejected as artifacts.

The minimum size threshold for nuclei of all cells is set at $\geq 35\mu^2$. The maximum size threshold for all cells is $<600\mu^2$. For a cell to be categorized as a morphologically transitional cell the minimum nucleus size is $\leq 45\mu^2$. For a cell to be categorized as a morphologically abnormal cell the nucleus size is $\geq 60\mu^2$. The size limits of the cytoplasmic portion of all cells are $\geq 200\mu^2$ and $\leq 4000\mu^2$.

Object images which survive this review step undergo further analysis. In particular, object images are reviewed more slowly to examine the nuclei. At this stage objects which lack nuclei, such as cell fragments, or have more than one nucleus are rejected. At this stage, cells abnormal for DNA and tissue fragments with DNA are detected and their coordinate locations are recorded. Similarly, the field is irradiated with an excitation wavelength for the M344-conjugated fluorochrome. The resulting field image is corrected for sources of extraneous fluorescence such as background fluorescence and autofluorescence, and for camera shading. The field image is then segmented into discrete object images which are reviewed for a positive appearance for M344 (i.e., fluorescence intensity exceeds a predetermined threshold) and which satisfy desired morphological requirements for size and shape. If positive object images are identified, their coordinate locations are recorded. Images of these selected cells may be stored. Positive object images are searched for until the entire slide has been examined or until a predetermined minimum number of recorded M344 positive images has been exceeded. An example of such a predetermined threshold is 20 positive images per 5,000 cells on the prepared slide.

Once the field image has been searched under the first magnification (low power e.g. 12.5 X power for DNA, 25 X for most other markers), each object image identified as abnormal image is viewed again under a second, higher, magnification (e.g. 25 X power for DNA) (FIG. 17) during which the high power object image is reviewed again for comparison with predetermined selection requirements and DNA is quantified. For example, objects showing cells with nuclei touching or other cell fragments are eliminated from consideration. Object images which pass this selection process are reviewed again more slowly and are compared to selection parameters related to cell shape. Additionally, DNA is quantified at this point. If the object images survive this review, and are still considered to be morphologically abnormal, or have DNA in excess of a predetermined amount (e.g., $\geq 5C$), object images are stored.

The slide is searched for positive object images until the entire slide has been examined or until a predetermined number of cells with abnormal DNA has been recorded (e.g. until the gallery is full of stored images). Under high magnification, a random scan for cells with abnormal DNA continues until at least 100 cells are measured. In the case of G-actin, the scan continues until 100 cells have been measured for G-actin or until the DNA scan is complete.

The stored object images of abnormal cells, cells with abnormal amounts of DNA or cells positive for M344 (or positive for a similar marker, or having particular quantities thereof) may be reviewed again by another method for confirmation. For example, the object images may be confirmed by a trained operator, or the stored object images may be delivered to an automated confirmation system such as a neural net computer trained with a library of normal, abnormal, positive, negative and false positive cell images.

Autofluorescence

For unknown reasons cells from urine often fluoresce even in the absence of added fluorophore. This autofluorescence can introduce error into the result because the fluorescence emitted from a given portion of a labeled cell will be the sum of autofluorescence plus that light emitted from the bound probe. One method of accounting for autofluorescence is to determine the average autofluorescence of some number of cells on a negative control slide to which no probe has been added. This average autofluorescence (as IGL) is then subtracted from the IGL of each examined labeled cell on the slide.

Unfortunately, these methods of accounting for autofluorescence error are not adequate. Autofluorescence occasionally varies widely from cell to cell in a population of cells. For example, a minority of cells may be very bright by autofluorescence, thus adding an element of error to the average. In addition, autofluorescence may be unevenly distributed within a single cell. Some methods raise the threshold intensity of emitted light which is measured. However, this method decreases the sensitivity of the of the measurement resulting in the possibility that some "low expressing" cells may be "lost". An accurate method of accounting for autofluorescence would increase the accuracy and precision of fluorescence analysis.

Correction for Autofluorescence

In the present invention, the preferred method for accounting for error due to autofluorescence is to measure the autofluorescent light emitted from each cell upon excitation by a predetermined excitation wavelength. The grey level image of the cell is then corrected on a pixel-by-pixel basis.

Each fluorochrome used to label a particular marker has a known spectral response and has a characteristic excitation wave-length which causes peak fluorescence emission (see Table IV). When the cell labeled with the fluorochrome is irradiated with the excitation wavelength, the total fluorescent light emitted from the cell is comprised both of light emitted from the fluorochrome, and of light emitted from other components of the cell. The latter is the autofluorescent component of the total emitted fluorescence. To obtain an accurate measurement of the light emitted from the label, the fluorescent portion must be subtracted from the total emitted light.

Figure 20:
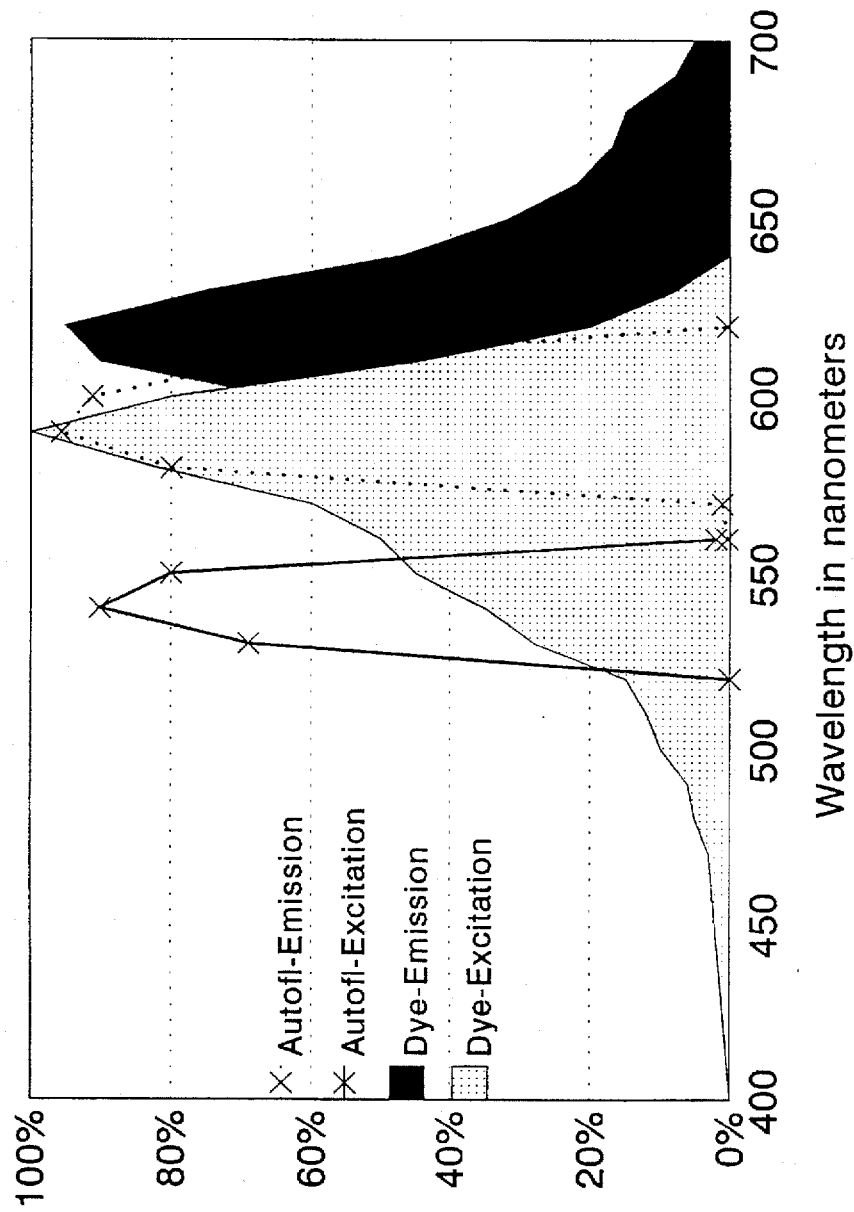
FIG. 20 is a graph of fluorescent excitation and emission patterns of Texas Red for correcting for autofluorescence.

This could be done by calculating an average autofluorescence over the entire image, then subtracting the same average amount of autofluorescence from each pixel of the image. However, the autofluorescent component can vary from pixel to pixel. Therefore, a method which subtracts only an average autofluorescent value can still result in significant error in any given pixel. To determine the amount of autofluorescence for a given pixel a second excitation wavelength is chosen from the tail of the fluorochrome's excitation spectrum. This wavelength is significantly different from the peak excitation wavelength of the fluorochrome (FIG. 20).

When the slide is irradiated with this second autofluorescence wavelength, most of the fluorescent light which is emitted is autofluorescence, with a small portion being emitted from the fluorochrome. In effect, the autofluorescence wavelength mildly excites the fluorochrome but does not cause a high level of excitation such as is caused by the peak excitation wavelength for the fluorochrome. The fluorescence emission is then digitized for each pixel in the image. This fluorescence is mostly autofluorescence.

Each calculated autofluorescence grey level is subtracted from the grey level obtained for that pixel when the slide is irradiated with the excitation wavelength of the fluorochrome. The resulting grey level value is the pixel grey level corrected for autofluorescence and primarily represents the quantity of the fluorochrome in that portion of the cell. Most of the autofluorescence is effectively removed from the image. This correction is made for each pixel of each cell measured.

EXAMPLE 4

Risk Assessment with Biomarkers

The process of cancer development is slow but progressive in that biochemical changes in cells are frequently apparent well before a clinically detectable tumor is present. The transition from "normal" to "premalignant" to "malignant" is continuous in that there is no single known marker that is always positive in cancers and never positive in premalignant lesions. Therefore one can only discuss "risk," which can have several meanings. The medical endpoint is a detectable tumor, but it is very clear that tumors exist before they can be detected by the usual diagnostic tests. For a variety of reasons, these tests do not always yield reliable results so that a false negative diagnosis sometimes occurs. Therefore, laboratory testing provides two kinds of information. One is "confidence," which is the probability that a given profile of markers establishes the presence of disease. The second is "risk assessment," which generally means an assessment of the patient's future prospects, but which can include the concept of risk for the disease. Thus, one can discuss the risk that a patient faces in having his or her disease progress to a more severe grade of disease, the risk that a cancer will recur, or the risk that a cancer will develop. Both surety and risk assessment can be stated in quantitative probabilistic terms (e.g. 22.4% of patients with such a marker profile will develop disease with 5 years) or as discontinuous assessments of risk or probability (e.g. "it is very certain that the patient has cancer" or "at moderate risk for recurrence"). The ideas of surety and risk assessment are not independent, and the same statement can contain both surety and risk assessment information. The statement that "74% of patients with these findings have a clinically detectable cancer" contains both surety information (i.e. we are 74% confident of the diagnosis) and a risk assessment (i.e. this person has a 74% risk for having cancer.)

TABLE XI

Definition of risk categories using visual cytology and rate of appearance of cells with > 5C DNA as determined with Hoechst 33258 dye.

| Risk Category | Visual Cytology | Cells with >5C DNA |
|---|---|---|
| 5 | Suspicious or positive | ≧2/500 ≧2/500 |
| 4 | Atypical | ≧2/500 |
| 3 | Atypical | 1–2/500 |
| 2 | Atypical | 0/500 |
| 1 | Negative or viral changes | 0/500 |

An example of a risk categorization approach that has been developed for use in the interpretation of QFIA cytology is shown in Table XI. This schema combines both the information inherent in the visual cytology and the detection of aberrant cells with >5C DNA and combines both risk assessment and surety information. In fact, the DNA content data allow those patients with "atypical" cells to be further classified into those whose atypical cells are cancer related (Group 4) and those who are likely not (Group 2), leaving only a small intermediate group (Group 3). These categories correspond to: 1=no aberrant findings; 2=some abnormal findings that are rarely associated with cancer but which more usually are associated with benign processes and if associated with cancer are associated with very low grade, nonaggressive disease; 3=some abnormal findings that are occasionally associated with cancer but usually reflect age, smoking or other processes and if associated with cancer indicate either a very low grade, nonaggressive disease or very early stages of more aggressive disease; 4 and 5 indicate abnormal findings associated with low and high grade disease, respectively. The exact number of abnormal cells detected within a sample also provides confidence information. A finding of 20 cells with >5C DNA and atypical morphology almost certainly establishes that a patient also has a clinically detectable cancer. The probability that a patient with only 3 such cells has a clinically detectable cancer is obviously lower. Such a small number of cells could have arisen in a pre-malignant lesion, a small lesion not visible by cytoscopy, or could be the result of a few failed divisions in cells that leave no progeny. Furthermore, confidence information can also be derived from the concordance among markers with in single cells. The probability that the three abnormal cells cited above arose from a cancer is higher if the cell also shows other cancer-related abnormalities that are independent of ploidy changes, examples being the tumor-related antigen, p300, and F-actin or G-actin.

The information in Table XI can be converted to a quantitative, probabilistic statement by (1) determining the proportion of patients in each category that have clinically detectable tumors at the time the test was performed and (2) following such patients for a time (e.g. 1 year) to determine what proportion of those in whom a tumor could not be found developed a tumor within the time period chosen or what proportion of patients in each category developed recurrences after the chosen time period. Table XI contains data from two markers (DNA and visual cytology). It could be readily expanded to include additional markers, such as those described in Example 1, without revising the categories. For example, addition of a tumor-related antigen measurement (e.g. p300 as determined by M344 antibody) could allow many patients in Group 3 that are associated with cancer to be categorized either into Group 2 or Group 4.

TABLE XII

Comparison of sensitivities (percent of patients with disease having abnormal findings) for QFIA cytology and Papanicolaou cytology in bladder cancer detection.

| Papanicolaou Tumor Grade Sensitivity | N | Sensitivity | N | QFIA Sensitivity |
|---|---|---|---|---|
| 1–2 | 74 | 81% | 86 | 52% |
| 3–4 or CIS | 52 | 100% | 54 | 96% |

An example of a probabilistic statement is provided in Table XII. In this study, QFIA cytology was performed on patients with known disease and compared to conventional Papanicolaou urinary cytology. Patients were classified by the grade of tumor. A positive finding for QFIA cytology was a Risk Category 4 or 5 as listed in Table XI. These data show that for the particular population of cancer patients selected, QFIA cytology performed better than did conventional cytology as well as providing a quantitative estimate of the surety of a given finding as related to the grade of tumor that the patient had.

TABLE XIII

Aggregate data from several studies of asymptomatic controls showing percentage distribution by risk category as a function of age.

| Age | N | Risk Category 5 | 4 | 3 | 2 | 1 |
|---|---|---|---|---|---|---|
| <50 | 57 | 0 | 4 | 4 | 33 | 60 |
| ≧50 | 162 | 4 | 4 | 4 | 29 | 59 |
| Total | 219 | 3 | 4 | 4 | 30 | 59 |

An additional examples is provided in Table XIII, which examines the question of what confidence can be placed in a positive finding. This shows that Groups 1–3 are predominately associated with benign findings but that the incidence of "false positive" findings increases with one known risk factor for bladder cancer, namely age. Smoking has a similar effect upon QFIA cytology as does bladder outlet obstruction and urinary tract stones, all of which increase the risk for cancer and produce cytologic changes characteristic of aberrant cells. Thus, QFIA cytology also is providing a risk assessment in that patients with such aberrant findings are shown to be at higher risk for developing bladder cancer than are patients without such findings.

A further point in the evaluation of marker profile measurements is that the marker itself may require validation, that is, it may be necessary to determine the relationship between the marker and disease if that marker does not have a history of use in medicine. This problem has been addressed by the development of a means of rapidly assessing whether a given new marker or combination of markers is useful for risk assessment. With this approach, a group of patients are stratified into groups representing distinct different experiences. This approach is illustrated in Table XIV, which shows how the marker F-actin was evaluated and determined to be a useful marker for assessing bladder cancer risk using a group of patients that had been stratified on the basis of perceptions of risk that were based upon expert experience.

TABLE XIV

Stratification of patients by various means establishes a gradient of risk that is used to validate a test such as F-actin.

| Patient Actin Content Group Can. | Patient Stratification Criteria | | | |
|---|---|---|---|---|
| | Hematuria Abnormal (%) | QFIA Cytology | Prev. | F-Blad. |
| One | — | Positive | — | 46(90) |
| Two | Yes | Intermediate | — | 18(75) |
| Three | Yes | Negative | Yes | 34(66) |
| Four | Yes | Negative | No | 13(36) |
| Five (Control) | No | Negative | No | 3(7) |

Patients in Group One are obviously at the highest risk for having cancer, given a positive cytology. In fact, all these patients had biopsy-proven disease. Group Two is symptomatic, having hematuria, and has an intermediate QFIA cytology. This combination of factors establishes that the Group Two patients are at higher risk than Groups Three or Four, and this is reflected by the high proportion (75%) of such patients exhibiting abnormal F-actin. Patients having hematuria and negative QFIA cytology, are next stratified by whether or not they had a previous history of bladder cancer. Those with a previous history of bladder cancer (Group Three) are at higher risk than those without (Group Four). This approach can be made quantitative by following such groups for some time period and determining the proportion that develop cancer within given time periods. This approach illustrates the importance of examining groups in addition to those with disease and those who are perfectly normal because it is the patients who are symptomatic who must usually be classified by any marker profile testing, not completely asymptomatic patients. The only exception is in routine screening of asymptomatic patients.

Figure 21:
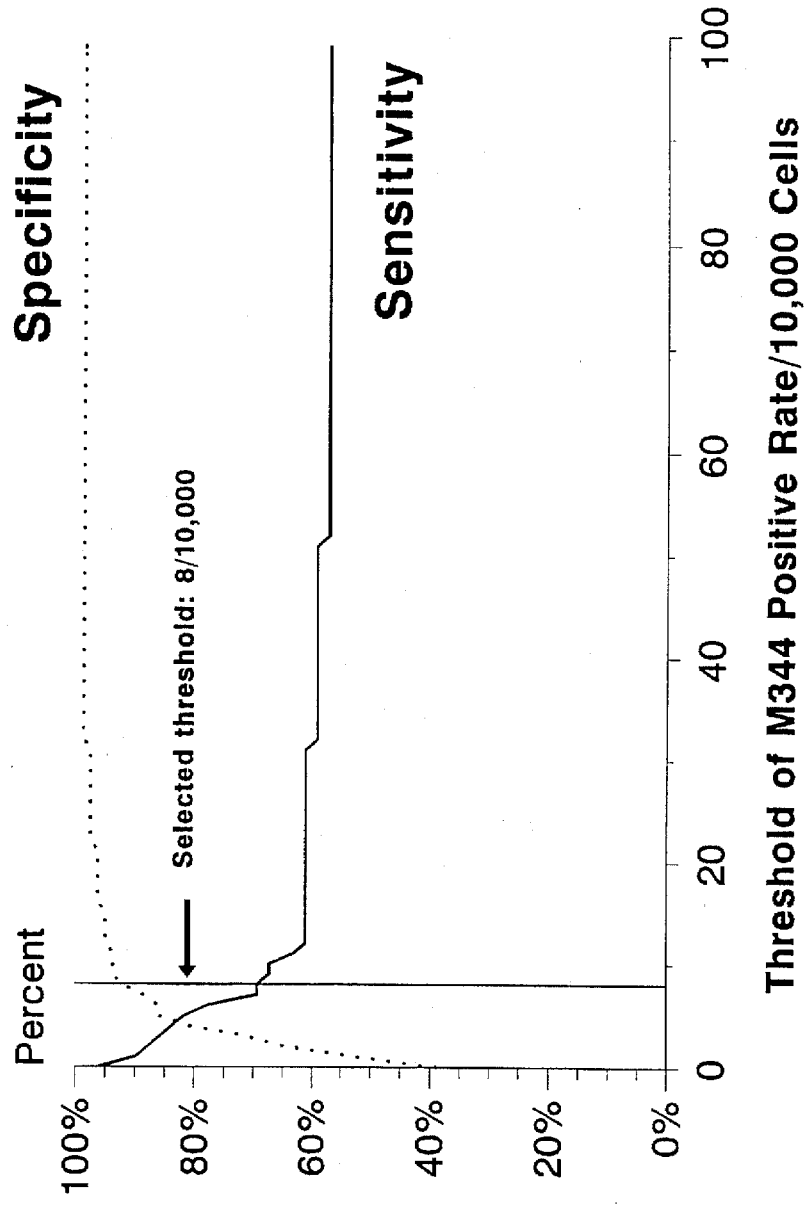
FIG. 21 is a specificity/sensitivity plot of the M344 antibody in cells of bladder washes.

Establishment of criteria for "positive" and "negative" for marker measurements in clinical samples is a complex process involving weighing of needs for sensitivity against those for specificity. FIGS. 3 and 21 illustrate how this can be achieved for the p300 tumor related antigen with voided urines and bladder washes respectively. These plots, which are derived from considerations of information theory and were first applied to signal/noise problems in radio, are referred to as "receiver operating characteristic" (ROC) plots. These plots were derived from studies of patients known to have cancer (sensitivity line) and from patients known not to have a clinically detectable cancer (specificity line). Included in those without disease are patients who are symptomatic. These plots are examined to determine the optimal threshold for identification of abnormal samples. The same plot can be used to set different thresholds as might be used for different applications. For example, a different threshold might be applied to populations of symptomatic individuals as compared to asymptomatic ones, or when the marker is used alone versus in combination with other markers.

EXAMPLE 5

Risk Assessment Using DNA, M344 and G-Actin as Markers

Multiple marker profiles can be developed to provide an estimate of the risk for cancer faced by an individual patient that can be used to guide subsequent treatment. This approach was used to stratify a population of individuals which had been exposed to a bladder carcinogen in the work place. The results were used to determine a set of risk categories, shown in Table XV, for guiding the continued clinical followup and management of this group. The three markers used were: DNA as measured by the % of cells in a urine sample with >5C DNA (ER5C) in the nucleus, the number of cells positive for M344 antibody per 10,000 cells assayed, and the mean G-actin content of the cells.

Samples having an ER5C≧0.8% of cells assayed were designated as "positive" (+) for ER5C. Samples having an ER5C≧2.0% of cells were designated as "strongly positive" (++). Samples having an ER5C <0.8% of cells assayed were designated as "negative" (−).

Samples in which either (1) the mean level of G-actin was ≧90 units or (2) the mean level plus the standard deviation of G-actin level was ≧130 units were designated as "positive" (+). Samples in which the mean level of G-actin alone was ≧140 units were designated as "strongly positive" (++) for G-actin. Samples in which mean G-actin was <90 units were designated as "negative" (−) for G-actin.

Samples having ≧2 cells which were positive for M344 per 10,000 cells measured were designated as "positive" (+) for ER5C. Samples having ≧10 cells per 10,000 measured were designated as "strongly positive" (++). Samples in which there were <2 cells positive for M344 per 10,000 cells assayed were designated as "negative" (−).

Table XV shows the risk categories (from Very High Risk to High Risk to Moderate Risk to Low Risk) correlated with particular profiles of each of the three markers. Each sample surveyed has a particular marker profile, and based on the marker profile, is assigned a risk category. Each risk category can be assigned a specific course of clinical action. This course of clinical action can then be proposed to the individual from whom the sample was obtained.

For bladder cancer risk, for example, the following protocols may be proposed. Persons assigned to the Very High Risk status may be proposed to follow a course of immediate clinical action which includes a cystoscopic examination for tumor and a biopsy, and other diagnostic tests as needed. Persons assigned to the High Risk status may be proposed to follow a course of clinical action which includes being given a cystoscopic examination for tumor and having new samples taken and new marker profiles determined at six month intervals. Persons assigned to the Moderate Risk status may be proposed to follow a course of clinical action which includes having new samples taken and new marker profiles determined at one-year intervals. Persons assigned to Low Risk status (negative for all three markers) may be proposed to follow a course of clinical action which includes having new samples taken and new marker profiles determined at three-year intervals. It can easily be seen how such risk categories could be expanded to include additional markers.

Additionally, the risk categories can be modified or stratified based on additional personal data. This additional data may comprise demographic information such as gender, smoking/non-smoking status, and may include level of exposure to the carcinogen. Other known risk factors which may be known to relate to certain organ sites may be included in the risk profile. In the case of colon cancer, additional risk factors are presence of polyps, multiple polyposis and a history of previous cancer. In the case of bladder cancer, additional factors may be diverticulum or urinary stasis.

Moreover, each biomarker has several variables which may influence its expression. The first variable is the variability within the test. A second variable is a threshold cut-off established by a given marker based on ROC plots. A third variable is the threshold of intensity of fluorescence for the marker.

TABLE XV

Bladder Cancer Risk Categories Using DNA, G-actin, and M-344 as Markers

| Risk Level | ER5C | G-actin | M-344 |
|---|---|---|---|
| Very High Risk | + or ++ | + or ++ | + or ++ |
|  | + or ++ | − | ++ |
|  | − | + or ++ | ++ |
|  | − | − | ++ |
| High Risk | + | + | − |
|  | ++ | − | − |
|  | + | − | + |
|  | − | ++ | − |
|  | − | + | + |
|  | − | − | + |
| Moderate Risk | + | − | − |
|  | − | + | − |
| Low Risk | − | − | − |

Legend:
ER5C: − = % of cells having > 5C is < 0.8%
+ = % of cells having > 5C is ≧ 0.8%
++ = % of cells having > 5C is ≧ 2.0%
G-actin: − = mean G-actin level < 90 units
+ = mean G-actin level ≧ 90 units or mean + S.D. > 130 units
++ = mean G-actin ≧ 140 units
M-344: − = ≦ 2 cells per 10,000 are positive for M344
+ = ≧ 2 cells per 10,000 are positive for M344
++ = ≧ 10 cells per 10,000 are positive for M344

EXAMPLE 6

Neural Networks

This example relates to directly encoding gray level images for classification by neural nets for use in automated cancer diagnosis or in detection of abnormal cells resulting from the process of carcinogenesis.

Neural networks are artificial intelligence systems which seek to model the physiological process at a neuronal level. The neural network encodes human-made decisions in the form of connection weights among the computational elements. Neural networks are adaptable to circumstances in which a human is able to consistently make a decision, and does not require any encoding of that knowledge, i.e., the neural network can be trained to replicate the human decision without any explicit knowledge of how that decision was made.

The neural network is a device for "learning." If presented with a set of complex patterns that are classified by a human observer, the neural network can "learn" to recognize members of each of the classes it was "trained" to recognize. In addition, if new objects that the neural net has not been trained to recognize are presented, the neural network is capable of determining that such objects do not fit any current classification. Neural networks are, in general, tolerant of some variation in characteristics within a given class. Neural networks are also rapid, usually achieving at least a near real time performance, even with complex images.

Though the concept of using an artificial neural network system (ANNS) to solve pattern recognition has been proposed since the fifties, recent advancement of learning theory and adaptive signal processing has greatly increased and strengthened the use of ANNS for practical problems. Research projects directed to applications of artificial neural networks can be roughly categorized into three main areas: pattern recognition/associative memory, artificial intelligence, and optimization. Pattern recognition problems have direct applications in robotics, machine vision, and natural language understanding. Artificial intelligence problems include game theory, and other heuristically oriented applications. Optimization problems include modelling, estimation, prediction, and control. One application of neural networks is in recognition of visual images, such as is required in the present invention.

The use of a neural-like network offers several advantages. First, a neural-like network performs the necessary and suitable "transformation" and "clustering" operations automatically and simultaneously. That is, the neural-network is able to abstract the distinctions between normal and abnormal patterns during the training session even though such distinctions may not be apparent. Secondly, a multi-layered neural-like network, specifically three or more, is able to recognize complex and non-linear groups in the hyperspace. This is a distinct advantage over conventional techniques. Thirdly, a neural-like network is massively parallel in nature and operates in parallel in close to real-time speed.

In the present invention, neural networks are used as part of an automated system wherein encoded grey level images are utilized in cancer diagnosis and cancer risk assessment.

An ANNS is a network that is composed of a large number of neuron-like processing elements called synthetic neurons that are densely interconnected to one another wherein the nodes of the network representing the synthetic neurons themselves. Used herein, the term neuron refers to synthetic neurons or neuron-like elements. The operation of a synthetic neuron can be functionally represented as a linear combiner as shown below (Eq. 9):

$$a_i = T \left[ S_i = \sum_{j=1}^{p} a_j W_{ji} \right] \quad (9)$$

where $a_i$ is the output of the ith neuron in a network of P neurons; $W_{ji}$ is a multiplicative weight representing the synaptic efficacy from the output of the jth neuron to the input of the ith neuron; $s_i$ is the intermediate sum of neuronal inputs; and T is the output transformation. Typically, the number of neuronal inputs is large indicating a rich and fully connected interconnection network among the neurons. The inputs to a neuron may be real valued or binary valued in general.

Eq. 9 shows that each neuronal input is weighted according to the efficacy of that corresponding junction or synapse. The weighted sum of all the inputs represents the intermediate output of the neuron. The actual output of the neuron, however, is a nonlinear function of this intermediate sum. It is this output transformation that gives the neuron non-linear characteristics and hence the ability to solve many optimization problems. In "first-generation" neural networks, T is sigmoid, but other mathematical relationships are not only possible but frequently offer enhanced performance in terms of improved trainability and training times, fewer layers or nodes needed to solve a given problem. Examples include sinusoidal or gaussian functions.

An ANNS consists of a collection of such neurons in a fully connected network. Such a network is completely characterized by the state of the neurons and the interconnections. The state of the neurons is usually represented by a vector describing the outputs of the neurons at a particular point in time. In addition, the synaptic weights between the neurons are described by a matrix. Information is stored in the interconnection network and in the efficacy of each synaptic junction, i.e., the synaptic weights. Information processing can be considered to occur as inputs passed through layers and layers of neural-like elements. Each layer of neurons provides an added transformation on the input data. Given an input vector then, the output vector can be derived from the neuronal state vector and the interconnection matrix to produce a stable output vector if the dynamics of the neuronal adaptation is known.

The ANNS can be trained to behave in a specified way by adaptively changing the weights toward the direction of the desired goal. There are two different approaches to adjusting the weights in a network. The first approach, called supervised learning, involves calculating the error in output achieved with a particular configuration and using one of several algorithms to feed that error back into the network. The most commonly used rule for changing weights is the generalized delta rule, which is an iterative gradient algorithm designed to minimize the mean square error between the actual output of a multilayer feed-forward perceptron and the desired output. This is a more generalized definition of back propagation employed with a sigmoid output transformation function. The mathematics will be different for each T in Eq. 9, because each T must be a continuous, differentiable non-linear function, but the principles are similar. This back error propagation approach has been successfully applied to many signature recognition projects such as sonar target recognition.

The second approach, which might be defined as a "second-generation" neural network, is ARTMAP, which is an example of unsupervised learning. The theoretical basis for this approach is Adaptive Resonance Theory. The fundamental principle of this theory is that a resonance will be established when the weights provide a solution to discriminating a particular set of patterns. At a conceptual level, this is analogous to an harmonic resonance with standing waves. Such networks are fundamentally different from those using a supervised learning algorithm because they are self-organized. ART systems carry out hypothesis testing to discover and learn good recognition codes when given a training set without common members in exclusive classes. ARTMAP can reject unfamiliar input as being unfamiliar (i.e. it provides an answer of "none of the above") so that incorrect classifications will not occur.

In this example, an image analysis system was used to perform preliminary algorithmic classification of images of exfoliated urine cells stained with a fluorescent dye which preferentially labels DNA and then to capture the grey-level images of potentially abnormal cells for analysis by a neural network. Digitized, grey-level cell images were captured on disks and were minimally processed for analysis by a trained neural network implemented on a Prime computer (VAX 780 equivalent). Minimally processed means normalized such that differences in DNA content were not a factor in the decision. The network consisted of an input layer (1936 neurodes), two hidden layers (50 and 24 neurodes each) and a single output node.

The network was trained with an image set consisting of both low and high grade cancer cells and several different examples of noncancer cells. A second, test set was evaluated without disagreement with a human expert (Table XVI). The principle was proven unequivocally that grey level images of cells having DNA labeled with fluorescent probes could serve as direct input for a neural network and that such networks could be trained to differentiate cancer cells from noncancer cells. The results clearly demonstrated the feasibility of using neural networks to recognize and classify grey level images captured by an image analysis microscope.

In a system for evaluating more than one marker, an image library for each marker would be selected. This is based upon the assumption that markers do not interfere with each other, an assumption that is satisfied using the processing techniques described herein for the present invention.

Methodology

Image library: An image library was collected by an expert cytologist with a Zeiss IBAS system. The IBAS is a full-function image analysis system with image capture capabilities. The cells were labeled with H-33258, a fluorescent dye that labels DNA preferentially. The images were stored as 512×512 pixel gray level images on floppy disks and sent for preliminary image processing to extract the image of the cell in a 64×64 format. These images were then analyzed at another site. An adequate image library is selected from cell images from patients known to have certain clinical conditions. Thus, cells representing cancer are taken from cells found in the urine of patients known to have cancer. Cells representing the normal condition are taken from individuals having no indications of cancer. Cells representing premalignant conditions are taken from patents who previously had a cancer but who do not currently have a detectable cancer, and who have one or more abnormal quantitative markers. Cells representing false results are obtained from patients being seen for urologic conditions other than cancer (e.g., chronic infection or benign prostatic hyperplasia) who have been evaluated and found to be free of cancer. The cells are then characterized by an expert cytologist (e.g., normal cell). Thus, each image will have associated two characteristics, its intrinsic classification and the clinical condition of the patient. An example might be "normal cell from cancer patient."

The image library consisted of the following cell types:

Normal cells from noncancer urines: Squamous cells (12 images). These are often found in female urine and represent cells that are differentiating along a more skin cell-like pathway. Transitional urothelial cells (12 images) represent the usual cells lining the bladder. Cancers are generally derived from this cell type. Polymorphonuclear leukocytes PML (8 images) are white cells found in the urine as a response to infection or inflammation.

Abnormal cells from cancer cases: Mild-moderate atypical cells (12 images) express mild morphological changes. These can be derived from both low-grade cancers and noncancer causes, and the challenge of bladder cancer diagnosis is to identify those that are derived from cancer. Moderately-severely atypical cells (12 images) are more severely altered. Suspicious cells (16 images) are found in high-grade tumors and have a characteristic abnormal appearance.

A selected image library was prepared as follows. Normal: Squamous cells (10 images), Transitional cells (2 images), PML (1 image); Cancer cases: Suspicious cells (10 images).

Neural Network Training and Testing: The neural network consisted of a 1936 neurode input layer (44×44+1 threshold modifier), two hidden layers of 50 (49+threshold modifier) and 24 neurodes respectively and a single output (Abnormal cell vs Normal cell). There was full connectivity, and neurodes were defined as perceptrons. The neural network was simulated in software on a Prime (VAX 780 equivalent 12 mips machine). The remainder of the normal cells and suspicious cells were used as a test set.

Results

The training time was approximately 24 hours. The time to classify a test image, however, was only 2 minutes of calculation time. Table XVI demonstrates the concordance between the human expert and the trained neural network with the second, independent test set. All test cell images were correctly classified as either normal cell or abnormal cell. It is of interest that this was achieved with a training set that emphasized squamous cells over transitional cells, while the test set was richer in transitional cells. This demonstrates that the results achieved with the neural net may have a degree of generalizability.

TABLE XVI

Comparison of Cell Classifications by Trained Neural Network Versus Human Expert

| Cell Type Net Abnormal | Classification By Human Expert | Classification Using Neural Normal | |
|---|---|---|---|
| Normal Squamous Cells | 2 | 2 | 0 |
| Normal Transitional Cells | 10 | 10 | 0 |
| Normal PMLs | 7 | 7 | 0 |
| Suspicious Transitional Cells | 6 | 0 | 6 |

A truly improved hybrid system will use algorithmic processing to identify potentially abnormal objects and a neural network to at least partially replace the human in classification of cell images. Hardware implementations of neural networks are commercially available. Hardware implementation will permit the true massive parallel processing rather than software simulation in a linear sequentially-processing digital computer. The approximate 10 μs required to process an image with hardware implementation will make classification of each image feasible. A reduction in training times can be achieved by using a more powerful computer, by various image-compression techniques to reduce the number of elements in the image, or by a combination of approaches.

EXAMPLE 7

Classification of Bladder Cells Using a Hybrid Multi-Layer Neural Network

Described herein is a new multi-threshold modified Perceptron capable of handling both binary and analog input. The modified Perceptron replaces the sigmoid function with sinusoidal function. A computer program was developed to simulate behavior of a network utilizing the modified Perceptron. A network utilizing this modified Perceptron requires fewer number of iterations to converge to a solution than that of a multi-layer Perceptron network using back propagation. A hybrid multi-layer network using the modified and sigmoidal perceptron was used to classify images of bladder cells. The results indicated that the hybrid network was capable of correctly classifying the images.

The single-layer Perceptron was one of the first neural networks developed. It is capable of handling both binary and analog inputs. The single-layer Perceptron can only classify input patterns that can be completely separated by a single hyperplane. Therefore, problems in which the input patterns cannot be separated by a single hyperplane can not be solved using single-layer Perceptron. This limits utility of single-layer Perceptron and points to the use of multi-layer Perceptron networks.

The multi-layer Perceptron network is a feed-forward network with one or more hidden layers of neurons between the input and output layers. Using this architecture, many shortcomings of the single-layer Perceptron can be avoided. However, because of the added complexity, the convergence theorem and weight adjustment procedure are not applicable. An alternate procedure called Back Propagation (BP) was developed (for example, see D. E. Rumelhart, J. L. McClelland and The PDP Research Group, Parallel Distributed Processing Explorations in the Microstructures of Cognition, Vol. 1. Foundations, MIT Press, Cambridge, Mass., 1988). This procedure is effective and allows for efficient use of multi-layer Perceptrons. But the procedure does not guarantee convergence to the global minima at all times. Also, it requires a large number of training iterations in order to learn a given set of transformations.

A modified Perceptron is discussed here. The modified Perceptron is a multiple threshold Perceptron. This Perceptron is capable of handling both binary and analog inputs and requires fewer number of iterations (as compared to BP) to develop appropriate input to output transformations.

Multi-Layer Perceptron

When the input patterns are not linearly separable a more complex structure (compared to single-layer Perceptron) is required to classify these patterns correctly. Multi-layer Perceptron presents one such structure. Multi-layer Perceptrons are feed-forward networks with one or more neuron layers (hidden layers) between the input and the output nodes.

Because the convergence theorem and weight adjustment procedures developed for single-layer Perceptron do not apply to multi-layer networks they had limited utility until a new procedure called Back Propagation (BP) was developed.

The BP approach has proven to be an effective training algorithm however it is not guaranteed to converge to the global minima in every instance. Also, BP requires a large number of iterations before it is able to utilize the learned patterns for solving a problem. The utility of the BP technique is due to the surprising computational power of networks with hidden layers.

Alternate Non-Linearity Function

The non-linearity function of interest not only must be able to form multiple decision boundaries but also must be continuous and its derivative must exist for all input patterns if it is to be used in a multi-layer configuration utilizing BP.

There are a number of functions that satisfy the multiple decision boundaries requirement specified. Sinusoid, Gaussian, double Sigmoid, and some piecewise linear functions all satisfy this requirement. The double sigmoid function correctly forms the required decision boundaries but it provides three distinct output values (−1,0,1). Therefore, double sigmoid function can be used to simulate tri-state logic. However, to simulate a binary logic element, an element capable of providing binary output is required. The same is true for piecewise linear function; in addition, it cannot be used for multi-layer configurations utilizing BP because its derivative is not defined for all values of input.

The Gaussian and sinusoid functions present the best choices for a binary valued neuron. This is due to the fact that their derivatives are defined for any possible value of input; and they can form multiple decision boundaries. However, the Gaussian function is more difficult to work with and is not as efficient as sinusoidal function. This is due to the fact that in the present case, it is required to evaluate the derivative of the nonlinearity function used. Also, in order to obtain more than two decision boundaries, a number of gaussian functions with different mean values must be added. But the periodical nature of the sinusoidal function automatically provides for having any number of decision boundaries. Hence, the sinusoidal function only is considered.

Sinusoidal Perceptron

A sinusoidal version of a single-layer Perceptron was developed, in place of the sigmoid function used by Rosenblatt. The sinusoidal function, $f_s$ is defined in Eq. 10.

$$f_s \text{Sin}(f^*a) \tag{10}$$

where "f" is the frequency and "a" is the weighted sum of the Perceptron inputs.

After each iteration the weights are adjusted as follows:

$$w(t+1) = \begin{cases} w(t) + h(d-y(t))x(t) & \text{if slope of } f_s \geq 0 \\ w(t) - h(d-y(t))x(t) & \text{if slope of } f_s \leq 0 \end{cases} \tag{11}$$

In Eq. 11 w(t) is the weight at iteration "t", h is a positive constant less than "1" called learning rate, and x(t) is the input pattern of interest. Variable "d" represents the desired output corresponding to x(t), and y(t) is equal to ai using Eq. 9.

A computer program was developed to simulate the behavior of the modified Perceptron. Results of the simulations indicate that use of a sinusoidal function as the non-linearity function allows the single-layer Perceptron network to develop all the decision boundaries (hyperplanes) needed to correctly classify more than two distinct classes of input patterns.

Use in Cancer Cell Classification

The modified perceptron was combined with the traditional perceptron to form a more powerful multi-layer network to analyze images labelled with the M344 antibody. This network consisted of an input layer, an output layer and one hidden layer. The hidden layer and the output layer neurons used the sinusoidal and sigmoid nonlinearity functions, respectively. The network was trained using two different sets of training data obtained from the recorded images. The recorded images were up to 70×70 pixels.

The first approach utilized a 10×10 set of pixels from the center of each cell. Therefore, the network required 100 input neurons. Hidden layer had 10 sinusoidal neurons and the output layer had one sigmoidal neuron. A total of 60 training sets was used to train the network to distinguish between cells falsely positive for the M344 marker and negative cells. A total of four test cases were used. The four represented two positive cells, one negative cell, and one false positive cell. The network required an average of 195 iterations to learn the data. The average number of iterations (maximum of 870 and minimum of 57 iterations) corresponds to different seed numbers used for the random number generator. The network successfully classified the four test cases. This approach was not able to correctly learn four of the images used for the training set.

The second approach used 55 images for training and 8 for testing the network. The test set consisted of 4 positive, 2 negative, and 2 false positive. Each image was reduced to 60×60 pixels.

The network used was a multi-layer network consisting of an input layer (3600 neurons), hidden layer (85 sinusoidal neurons), and an output (one sigmoidal neuron) layer. The network required 503 iterations (between 8 to 24 hrs of CPU time depending on the load on the machine) to learn the training set. Given an appropriate threshold (0.35 and 0.75) the network classified all test cells correctly.

Based on the results obtained from comparing a single-layer network of the modified Perceptron and multi-layer Perceptron network using BP, it is shown that the modified Perceptron is more efficient in forming required transformations from input to the output during the learning process for problems where convex decision regions can be used.

Changes may be made in the embodiments of the invention described herein or in parts of the elements of the embodiments described herein or in the steps or in the sequence of steps of the methods described herein without departing from the spirit and scope of the invention as defined in the following claims.

What is claimed is:

1. A method of assessing an individual's risk for bladder cancer, comprising:

providing a prepared slide having a population of cells affixed thereto, the prepared slide having been prepared by applying a portion of a cell sample provided by the individual to a slide then treating the slide with a first fluorescent label for labeling cellular DNA and at least a second fluorescent label for labeling a second cytological marker;

irradiating the prepared slide with an amount of a first excitation wavelength of light effective in causing the first fluorescent label in the cells to emit fluorescent light having a first emission wavelength;

obtaining a first population parameter related to the number of cells in the population of cells having quantities of cellular DNA which exceed a predetermined threshold quantity of cellular DNA;

irradiating the prepared slide with a second excitation wavelength of light effective in causing the second fluorescent label to emit fluorescent light having a second emission wavelength;

obtaining a second population parameter related to the number of cells in the population of cells having quantities of the second cytological marker which exceed a predetermined threshold quantity of the second cytological marker;

comparing the first population parameter to a set of predetermined first parameter thresholds;

comparing the second population parameter to a set of predetermined second parameter thresholds; and assigning a predetermined risk for bladder cancer to the individual based on which first parameter thresholds and second parameter thresholds are exceeded.

2. The method of claim 1 wherein the step of obtaining a first population parameter is preceded by the step of using a neural net means to review selected cells identified as having quantities of cellular DNA which exceed the predetermined threshold of cellular DNA.

3. The method of claim 1 wherein the step of obtaining a second population parameter is preceded by the step of using a neural net means to review selected cells identified as having quantities of the second cytological marker which exceed the predetermined threshold of the second cytological marker.

4. The method of claim 1 wherein in the step of providing a prepared slide, the portion of the cell sample used in preparing the slide was a urine sample or bladder wash.

5. The method of claim 1 wherein in the step of providing a prepared slide the second cytological marker is selected from the group consisting of actin, EGFR and HER-2/neu protein.

6. The method of claim 1 wherein the step of providing a prepared slide the is selected from the group consisting of an anti-HER-2/neu protein probe plus a fluorescent conjugate, an anti-EGFR probe plus a fluorescent conjugate, and DNase I plus a fluorescent conjugate.

7. The method of claim 6 wherein in the step of providing a prepared slide the fluorescent conjugate is selected from the group consisting of Texas Red, bodipy and fluorescein.

8. A method of analyzing a cell sample, comprising:

providing a prepared slide having a population of cells affixed thereto, the prepared slide having been prepared by applying a portion of a cell sample to a slide then treating the slide with a fluorescent label for labeling cellular p300 protein;

irradiating the prepared slide with an amount of an excitation wavelength of light effective in causing the fluorescent label in the cell to emit fluorescent light having an emission wavelength;

using a microscope means to select cells;

classifying each cell as positive or negative for a predetermined quantity of D300 protein;

using a neural net computing means to further classify a positive cell as a true-positive cell or as a false-positive cell wherein a true-positive cell is defined as having a cellular distribution of D300 protein characteristic of an abnormal cell, said cellular distribution being distinguishable from the cellular distribution of p300 protein characteristic of a normal cell;

obtaining a population parameter related to the number of true-positive cells in the population of cells having quantities of p300 protein which exceed the predetermined threshold quantity of p300 proteins; and outputting the population parameter for use in classifying the cell sample.

9. A method of assessing an individual's risk for bladder cancer, comprising:

providing a prepared slide having a population of cells affixed thereto, the prepared slide having been prepared by applying a portion of a cell sample provided by the individual to a slide then treating the slide with a first fluorescent label for labeling a first cytological marker and a second fluorescent label for labeling a second cytological marker;

irradiating the prepared slide with an amount of a first excitation wavelength of light effective in causing the first fluorescent label in the cell to emit fluorescent light having a first emission wavelength;

using a microscope means to select first cell images;

classifying the first cell image as positive or negative for a predetermined quantity of the first fluorescent label;

using a neural net computing means to further classify a positive first cell image as a true-positive first cell image or as a false-positive first cell image;

obtaining a first population parameter related to the number of true-positive first cell images irradiating the prepared slide with a second excitation wavelength of light effective in causing the second fluorescent label to emit fluorescent light having a second emission wavelength;

using the microscope means to select second cell images;

classifying a second cell image as positive or negative for a predetermined quantity of the second fluorescent label;

using a neural net computing means to further classify a positive second cell image as a true-positive second cell image or as a false-positive second cell image;

obtaining a second population parameter related to the number of true-positive second cell images;

comparing the first population parameter to a set of predetermined first parameter thresholds;

comparing the second population parameter to a set of predetermined second parameter thresholds; and assigning a predetermined risk for bladder cancer to the individual based on which first parameter thresholds and second parameter thresholds are exceeded.

10. The method of claim 9 wherein in the step of providing a prepared slide the first cytological marker and the second cytological marker are selected from the group consisting of DNA, p300, actin, EGFR and HER-2/neu protein.

11. The method of claim 9 wherein in the step of providing a prepared slide the first fluorescent label and the second fluorescent label are selected from the group consisting of Hoechst 33258, M344 plus a fluorescent conjugate, an anti-HER-2/neu protein probe plus a fluorescent conjugate, an anti-EGFR probe plus a fluorescent conjugate, and DNase I plus a fluorescent conjugate.

12. The method of claim 11 wherein in the step of providing a prepared slide the fluorescent conjugate is selected from the group consisting of Texas Red, bodipy and fluorescein.

13. The method of claim 9 wherein the first cytological marker is DNA and the second cytological marker is the p300 protein antigen.

14. The method of claim 9 wherein in the step of providing a prepared slide the first cytological marker is DNA and the second cytological marker is actin.

15. A method of assessing an individual's risk for bladder cancer, comprising:

providing a prepared slide having a population of cells affixed thereto, the prepared slide having been prepared by applying a portion of a cell sample provided by the individual to a slide then treating the slide with a first fluorescent label for labeling a first cytological marker and at least a second fluorescent label for labeling a second cytological marker;

irradiating the prepared slide with an amount of a first excitation wavelength of light effective in causing the first fluorescent label in the cells to emit fluorescent light having a first emission wavelength;

obtaining a first population parameter related to the number of cells in the population of cells having quantities of the first cytological marker which exceed a predetermined threshold quantity of the first cytological marker;

irradiating the prepared slide with a second excitation wavelength of light effective in causing the second fluorescent label to emit fluorescent light having a second emission wavelength;

obtaining a second population parameter related to the number of cells in the population of cells having quantities of the second cytological marker which exceed a predetermined threshold quantity of the second cytological marker;

comparing the first population parameter to a set of predetermined first parameter thresholds;

comparing the second population parameter to a set of predetermined second parameter thresholds; and assigning a predetermined risk for bladder cancer to the individual based on which first parameter thresholds and second parameter thresholds are exceeded.

16. The method of claim 15 wherein the step of obtaining a first population parameter is preceded by the step of using a neural net means to review selected cells identified as having quantities of the first cytological marker which exceed the predetermined threshold of the first cytological marker.

17. The method of claim 15 wherein the step of obtaining a second population parameter is preceded by the step of using a neural net means to review selected cells identified as having quantities of the second cytological marker which exceed the predetermined threshold of the second cytological marker.

18. The method of claim 15 wherein in the step of providing a prepared slide, the portion of the cell sample used in preparing the slide was a urine sample or bladder wash.

19. The method of claim 15 wherein in the step of providing a prepared slide the second cytological marker is selected from the group consisting of actin, EGFR and HER-2/neu protein.

20. The method of claim 15 wherein the step of providing a prepared slide the second fluorescent label is selected from the group consisting of an anti-HER-2/neu protein probe plus a fluorescent conjugate, an anti-EGFR probe plus a fluorescent conjugate, and DNase I plus a fluorescent conjugate.

21. The method of claim 20 wherein in the step of providing a prepared slide the fluorescent conjugate is selected from the group consisting of Texas Red, bodipy and fluorescein.

22. A method of assessing an individual's risk for prostate cancer, comprising:
    providing a prepared slide having a population of cells affixed thereto, the prepared slide having been prepared by applying a portion of a prostate cell sample obtained from the individual to a slide then treating the slide with a first fluorescent label for labeling cellular DNA and at least a second fluorescent label for labeling a second cytological marker;
    irradiating the prepared slide with an amount of a first excitation wavelength of light effective in causing the first fluorescent label in the cells to emit fluorescent light having a first emission wavelength;
    obtaining a first population parameter related to the number of cells in the population of cells having quantities of cellular DNA which exceed a predetermined threshold quantity of cellular DNA;
    irradiating the prepared slide with a second excitation wavelength of light effective in causing the second fluorescent label to emit fluorescent light having a second emission wavelength;
    obtaining a second population parameter related to the number of cells in the population of cells having quantities of the second cytological marker which exceed a predetermined threshold quantity of the second cytological marker;
    comparing the first population parameter to a set of predetermined first parameter thresholds;
    comparing the second population parameter to a set of predetermined second parameter thresholds; and
    assigning a predetermined risk for prostate cancer to the individual based on which first parameter thresholds and second -parameter thresholds are exceeded.

23. The method of claim 22 wherein the step of obtaining a first population parameter is preceded by the step of using a neural net means to review selected cells identified as having quantities of cellular DNA which exceed the predetermined threshold of cellular DNA.

24. The method of claim 22 wherein the step of obtaining a second population parameter is preceded by the step of using a neural net means to review selected cells identified as having quantities of the second cytological marker which exceed the predetermined threshold of the second cytological marker.

25. The method of claim 22 wherein in the step of providing a prepared slide the second cytological marker is selected from the group consisting of actin, EGFR and HER-2/neu protein.

26. The method of claim 22 wherein the step of providing a prepared slide the second fluorescent label is selected from the group consisting of an anti-HER-2/neu protein probe plus a fluorescent conjugate, an anti-EGFR probe plus a fluorescent conjugate, and DNase I plus a fluorescent conjugate.

27. The method of claim 26 wherein in the step of providing a prepared slide the fluorescent conjugate is selected from the group consisting of Texas Red, bodipy and fluorescein.

28. A method of assessing an individual's risk for prostate cancer, comprising:
    providing a prepared slide having a population of cells affixed thereto, the prepared slide having been prepared by applying a portion of a prostate cell sample obtained from the individual to a slide then treating the slide with a first fluorescent label for labeling a first cytological marker and a second fluorescent label for labeling a second cytological marker;
    irradiating the prepared slide with an amount of a first excitation wavelength of light effective in causing the first fluorescent label in the cell to emit fluorescent light having a first emission wavelength;
    using a microscope means to select first cell images;
    classifying the first cell image as positive or negative for a predetermined quantity of the first fluorescent label;
    using a neural net computing means to further classify a positive first cell image as a true-positive first cell image or as a false-positive first cell image;
    obtaining a first population parameter related to the number of true-positive first cell images;
    irradiating the prepared slide with a second excitation wavelength of light effective in causing the second fluorescent label to emit fluorescent light having a second emission wavelength;
    using the microscope means to select second cell images;
    classifying a second cell image as positive or negative for a predetermined quantity of the second fluorescent label;
    using a neural net computing means to further classify a positive second cell image as a true-positive second cell image or as a false-positive second cell image;
    obtaining a second population parameter related to the number of true-positive second cell images; comparing the first population parameter to a set of predetermined first parameter thresholds;
    comparing the second population parameter to a set of predetermined second parameter thresholds; and
    assigning a predetermined risk for prostate cancer to the individual based on which first parameter thresholds and second parameter thresholds are exceeded.

29. The method of claim 28 wherein in the step of providing a prepared slide the first cytological marker and the second cytological marker are selected from the group consisting of DNA, p300, actin, EGFR and HER-2/neu protein.

30. The method of claim 28 wherein in the step of providing a prepared slide the first fluorescent label and the second fluorescent label are selected from the group consisting of Hoechst 33258, M344 plus a fluorescent conjugate, an anti-HER-2/neu protein probe plus a fluorescent conjugate, an anti-EGFR probe plus a fluorescent conjugate, and DNase I plus a fluorescent conjugate.

31. The method of claim 30 wherein in the step of providing a prepared slide the fluorescent conjugate is selected from the group consisting of Texas Red, bodipy and fluorescein.

32. The method of claim 28 wherein the first cytological marker is DNA and the second cytological marker is the p300 protein antigen.

33. The method of claim 28 wherein in the step of providing a prepared slide the first cytological marker is DNA and the second cytological marker is actin.

34. A method of assessing an individual's risk for prostate cancer, comprising:

providing a prepared slide having a population of cells affixed thereto, the prepared slide having been prepared by applying a portion of a prostate cell sample obtained from the individual to a slide then treating the slide with a first fluorescent label for labeling a first cytological marker and at least a second fluorescent label for labeling a second cytological marker;

irradiating the prepared slide with an amount of a first excitation wavelength of light effective in causing the first fluorescent label in the cells to emit fluorescent light having a first emission wavelength;

obtaining a first population parameter related to the number of cells in the population of cells having quantities of the first cytological marker which exceed a predetermined threshold quantity of the first cytological marker;

irradiating the prepared slide with a second excitation wavelength of light effective in causing the second fluorescent label to emit fluorescent light having a second emission wavelength;

obtaining a second population parameter related to the number of cells in the population of cells having quantities of the second cytological marker which exceed a predetermined threshold quantity of the second cytological marker;

comparing the first population parameter to a set of predetermined first parameter thresholds;

comparing the second population parameter to a set of predetermined second parameter thresholds; and assigning a predetermined risk for prostate cancer to the individual based on which first parameter thresholds and second parameter thresholds are exceeded.

35. The method of claim 34 wherein the step of obtaining a first population parameter is preceded by the step of using a neural net means to review selected cells identified as having quantities of the first cytological marker which exceed the predetermined threshold of the first cytological marker.

36. The method of claim 34 wherein the step of obtaining a second population parameter is preceded by the step of using a neural net means to review selected cells identified as having quantities of the second cytological marker which exceed the predetermined threshold of the second cytological marker.

37. The method of claim 34 wherein in the step of providing a prepared slide the second cytological marker is selected from the group consisting of actin, EGFR and HER-2/neu protein.

38. The method of claim 34 wherein the step of providing a prepared slide the second fluorescent label is selected from the group consisting of an anti-HER-2/neu protein probe plus a fluorescent conjugate, an anti-EGFR probe plus a fluorescent conjugate, and DNase I plus a fluorescent conjugate.

39. The method of claim 38 wherein in the step of providing a prepared slide the flourescent conjugate is selected from the group consisting of Texas Red bodipy and fluorescein.

* * * * *

UNITED STATES PATENT AND TRADEMARK OFFICE
CERTIFICATE OF CORRECTION

PATENT NO. : 5,741,648
DATED : April 21, 1998
INVENTORS : George P. Hemstreet, III et al.      Page 1 of 5

It is certified that error appears in the above-identified patent and that said Letters Patent is hereby corrected as shown below:

Column 4, line 36, in equation, "IOL" should be -- IOD --.

Column 4, line 49, "with" should be -- With --.

Column 5, line 6, please delete first word -- is --.

Column 5, line 32, after "light" please delete -- is --.

Column 8, line 29, "back-ground" should be -- background --.

Column 8, line 48, after "differences" insert -- in --.

Column 8, line 50, "al though" should be -- although --.

Column 15, please delete Table III, insert new Table III (as shown on page 3 of Certificate of Correction).

Column 23, line 18, after "positive" insert a comma.

Column 24, line 63, after "slide" please insert a period.

Column 25, line 41, "pk" should be -- pK --.

Column 27, line 25, "superatant" should be -- supernatant --.

Column 28, line 8, "Scc" should be -- 5cc --.

UNITED STATES PATENT AND TRADEMARK OFFICE
CERTIFICATE OF CORRECTION

PATENT NO. : 5,741,648
DATED : April 21, 1998
INVENTORS : George P. Hemstreet, III et al.

It is certified that error appears in the above-identified patent and that said Letters Patent is hereby corrected as shown below:

Column 28, line 16, "0.22 Am" should be -- 0.22 $\mu$m --.

Column 28, line 23, "0.22 Am" should be -- 0.22 $\mu$m --.

Column 28, line 30, "600c" should be -- 60°c --.

Column 31, line 36, after "of the" delete -- of the --.

Column 34, please delete Table XII, insert new Table XII (as shown on page 4 of Certificate of Correction).

Column 34, line 47, "examples" should be -- example --.

Column 35, please delete Table XIV, insert new Table XIV (as shown on page 5 of Certificate of Correction).

Column 41, please delete Table XVI, insert new Table XVI (as shown on page 5 of Certificate of Correction).

Column 43, line 28, "ai" should be -- $a_i$ --.

UNITED STATES PATENT AND TRADEMARK OFFICE
CERTIFICATE OF CORRECTION

PATENT NO. : 5,741,648
DATED : April 21, 1998
INVENTORS : George P. Hemstreet, III et al.

It is certified that error appears in the above-identified patent and that said Letters Patent is hereby corrected as shown below:

TABLE III
Stain Sequence - F-Actin + DNA

| Event | Station | Time | Solution |
|---|---|---|---|
| 1 | 8 | 1.00 MIX | PAD |
| 2 | 17 | 1.00 MIX | ANTIBODY |
| 3 | 7 | 30.00 | INCUBATOR |
| 4 | 8 | 1.00 | PAD |
| 5 | 10 | 0.10 | 1X AUTO. BUFFER (BM-M30) |
| 6 | 11 | 0.50 | PAD |
| 7 | 10 | 0.10 | 1X AUTO. BUFFER (BM-M30) |
| 8 | 11 | 0.60 | PAD |
| 9 | 10 | 0.10 | HOECHST |
| 10 | 8 | 1.00 MIX | PAD |
| 11 | 6 | 2.00 | HOECHST |
| 12 | 12 | 0.30 | PAD |
| 13 | 6 | 0.50 | HOECHST |
| 14 | 11 | 0.30 | PAD |
| 15 | 6 | 0.50 | HOECHST |
| 16 | 9 | 0.30 | PAD |
| 17 | 6 | 0.50 | HOECHST |
| 18 | 8 | 0.30 | PAD |
| 19 | 6 | 2.00 | HOECHST |

The total processing time: 42.10 min.

UNITED STATES PATENT AND TRADEMARK OFFICE
CERTIFICATE OF CORRECTION

PATENT NO. : 5,741,648
DATED : April 21, 1998
INVENTORS : George P. Hemstreet, III et al.

It is certified that error appears in the above-identified patent and that said Letters Patent is hereby corrected as shown below:

TABLE XII
Comparison of sensitivities (percent of patients with disease having abnormal findings) for QFIA cytology and Papnicolaou cytology in bladder cancer detection.

| | QFIA | | Papanicolaou | |
|---|---|---|---|---|
| Tumor Grade | N | Sensitivity | N | Sensitivity |
| 1-2 | 74 | 81% | 86 | 52% |
| 3-4 | 52 | 100% | 54 | 96% |

UNITED STATES PATENT AND TRADEMARK OFFICE
CERTIFICATE OF CORRECTION

PATENT NO. : 5,741,648
DATED : April 21, 1998
INVENTORS : George P. Hemstreet, III et al.

It is certified that error appears in the above-identified patent and that said Letters Patent is hereby corrected as shown below:

TABLE XIV
Stratification of patients by various means establishes a
gradient of risk that is used to validate a test such as F-actin.

| | Patient Stratification Criteria | | | F-actin Content |
|---|---|---|---|---|
| Patient Group | Hematuria | QFIA Cytology | Prev. Blad. Cancer | Abnormal (%) |
| One | - - | Positive | - - | 46 (90) |
| Two | Yes | Intermediate | - - | 18 (75) |
| Three | Yes | Negative | Yes | 34 (66) |
| Four | Yes | Negative | No | 13 (36) |
| Five (Control) | No | Negative | No | 3 (7) |

TABLE XVI
Comparison of Cell Classifications by
Trained Neural Network Versus Human Expert

| Cell Type | Classification by Human Expert | Classification Using Neural Net | |
|---|---|---|---|
| | | Normal | Abnormal |
| Normal Squamous Cells | 2 | 2 | 0 |
| Normal Transitional Cells | 10 | 10 | 0 |
| Normal PMLs | 7 | 7 | 0 |
| Suspicious Transitional Cells | 6 | 0 | 6 |

Signed and Sealed this

Seventeenth Day of November, 1998

Attest:

BRUCE LEHMAN

Attesting Officer    Commissioner of Patents and Trademarks

UNITED STATES PATENT AND TRADEMARK OFFICE
CERTIFICATE OF CORRECTION

PATENT NO. : 5,741,648 Page 1 of 1
APPLICATION NO. : 08/605342
DATED : April 21, 1998
INVENTOR(S) : George P. Hemstreet, III et al.

It is certified that error appears in the above-identified patent and that said Letters Patent is hereby corrected as shown below:

On the Title Page Under the Heading "Related U.S. Application Data": Delete the date "Dec. 20, 1992" and insert -- Nov. 20, 1992 -- .

Signed and Sealed this

Twenty-first Day of August, 2007

JON W. DUDAS
*Director of the United States Patent and Trademark Office*